United States Patent [19]

Shishido et al.

[11] Patent Number: 5,090,259
[45] Date of Patent: Feb. 25, 1992

[54] PIPE-INSPECTING APPARATUS HAVING A SELF PROPELLED UNIT

[75] Inventors: Yoshio Shishido, Sagamihara; Hideyuki Adachi, Tokyo; Hiroki Hibino, Tokyo; Tsutomu Yamamoto, Tokyo; Hirofumi Miyanaga, Tokyo; Syuichi Takayama, Tokyo; Yasuhiro Ueda, Tokyo; Yoshisade Aoki, Tokyo; Seiji Yamaguchi, Tokyo, all of Japan

[73] Assignee: Olympus Optical Co., Ltd., Tokyo, Japan

[21] Appl. No.: 488,494

[22] Filed: Mar. 2, 1990

Related U.S. Application Data

[63] Continuation of Ser. No. 272,007, Nov. 14, 1988, abandoned.

[30] Foreign Application Priority Data

| Jan. 18, 1988 | [JP] | Japan | 63-7953 |
| Jan. 18, 1988 | [JP] | Japan | 63-7954 |
| Feb. 10, 1988 | [JP] | Japan | 63-27677 |
| Feb. 10, 1988 | [JP] | Japan | 63-27678 |
| Feb. 10, 1988 | [JP] | Japan | 63-27679 |
| Feb. 10, 1988 | [JP] | Japan | 63-27681 |
| Feb. 10, 1988 | [JP] | Japan | 63-29282 |
| Feb. 10, 1988 | [JP] | Japan | 6-29283 |
| Feb. 19, 1988 | [JP] | Japan | 63-35168 |
| Feb. 22, 1988 | [JP] | Japan | 63-39302 |
| Feb. 23, 1988 | [JP] | Japan | 63-40196 |
| Feb. 24, 1988 | [JP] | Japan | 63-41518 |
| Feb. 25, 1988 | [JP] | Japan | 63-40591 |
| Feb. 25, 1988 | [JP] | Japan | 63-40592 |
| Feb. 26, 1988 | [JP] | Japan | 63-43644 |

[51] Int. Cl.⁵ ............................................... G01M 19/00
[52] U.S. Cl. ............................................ 73/866.5; 73/623; 324/220; 356/241; 358/100
[58] Field of Search .............. 73/865.8, 866.5, 623; 358/100, 98; 324/220, 221; 356/241

[56] References Cited

U.S. PATENT DOCUMENTS

| 4,006,359 | 2/1977 | Sullins et al. | 73/623 X |
| 4,189,944 | 2/1980 | Day et al. | 73/623 |
| 4,485,668 | 12/1984 | Hudson et al. | 73/405 A |
| 4,646,787 | 3/1987 | Rush et al. | 83/866.5 X |
| 4,677,865 | 2/1987 | Lehmann | 73/866.5 |
| 4,747,317 | 5/1988 | Lera | 73/866.5 X |
| 4,770,105 | 9/1988 | Takegi et al. | 73/866.5 X |
| 4,793,326 | 12/1988 | Shishido | 356/241 X |
| 4,807,484 | 2/1987 | Guedecke | 73/866.5 X |
| 4,832,473 | 5/1989 | Ueda | 350/506 |
| 4,848,168 | 7/1989 | Negishi | 73/865.8 |
| 4,889,679 | 12/1989 | Snyder et al. | 324/220 X |

FOREIGN PATENT DOCUMENTS

| 51-15678 | 5/1976 | Japan . | |
| 193121 | 8/1988 | Japan | 358/98 |
| 185508 | 7/1989 | Japan . | |
| 204015 | 8/1989 | Japan | 358/98 |
| 280716 | 11/1989 | Japan . | |
| 429345 | 6/1975 | U.S.S.R. | 356/241 |

OTHER PUBLICATIONS

*Patent Abstracts of Japan*, vol. 13, No. 505, Abs. pub. date Nov. 14, 1989.

Primary Examiner—Tom Noland
Attorney, Agent, or Firm—Frishauf, Holtz, Goodman & Woodward

[57] ABSTRACT

A pipe-inspecting apparatus having a self-propelled unit. The self-propelled unit comprises an elastic tube which has forward and rear ends, and into which a fluid is supplied and from which the fluid is discharged, a restriction member mounted on the elastic tube, for restricting an axial expansion of the elastic tube, a bias member for biasing the elastic tube in the axial direction thereof, first and second holding members coupled to the ends of the elastic tube, respectively, for holding the ends of the elastic tube to the inner periphery of a pipe being inspected, while the fluid is being supplied into the holding members, and releasing the ends of the elastic tube from the inner periphery of the pipe, while the fluid is being discharged from the holding members. An observation device is coupled to the self-propelled unit. A display device is connected to the observation device, for displaying the image scanned by the observation device. A fluid control device is connected to the elastic tube, and to the first and second holding members.

56 Claims, 59 Drawing Sheets

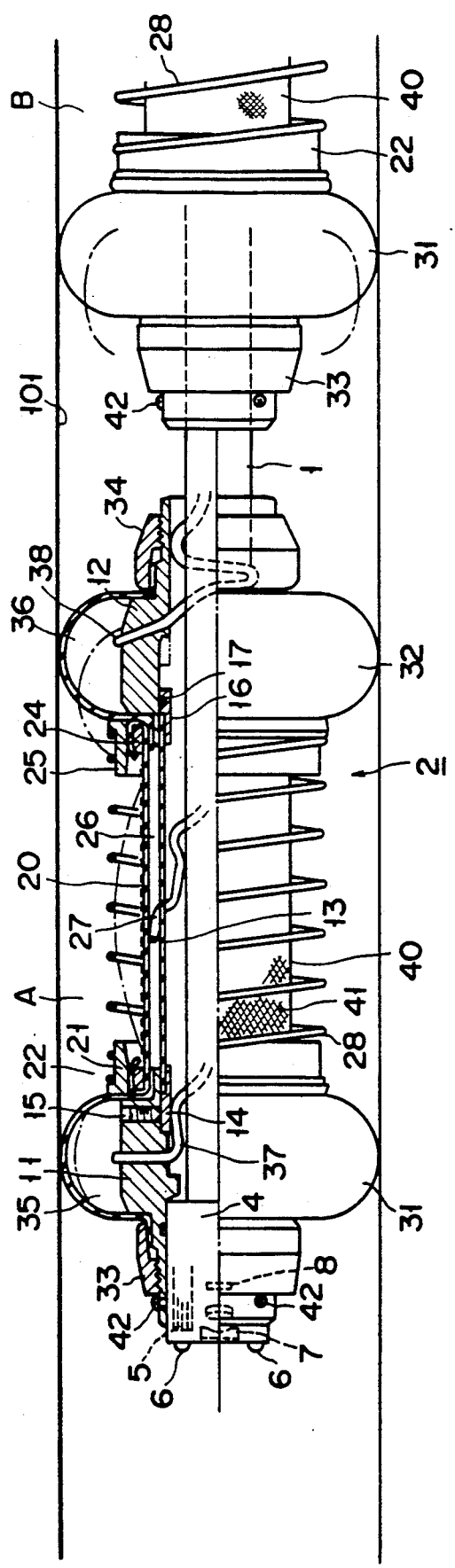
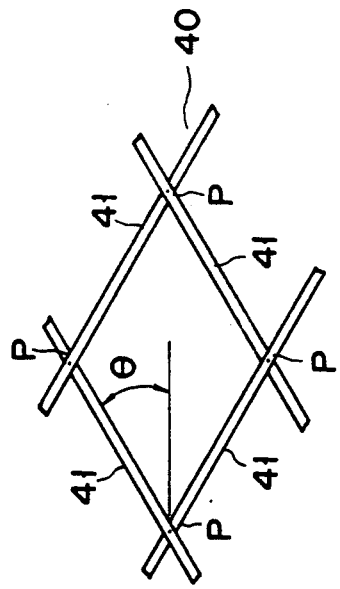
FIG. 1A
FIG. 1B

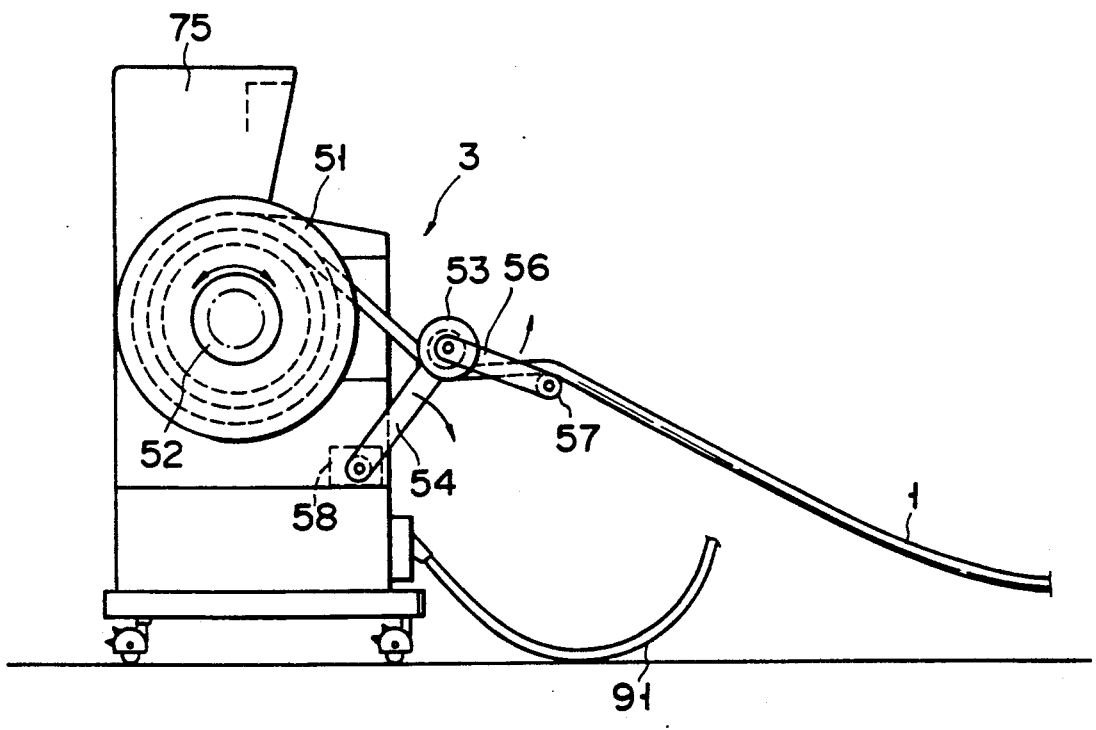
F I G. 3
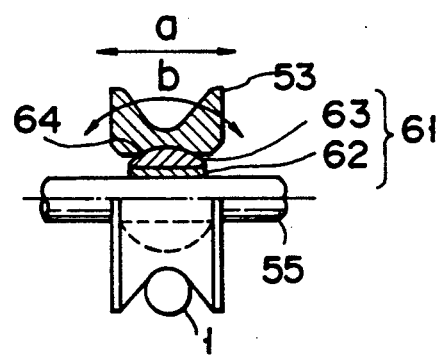
F I G. 4

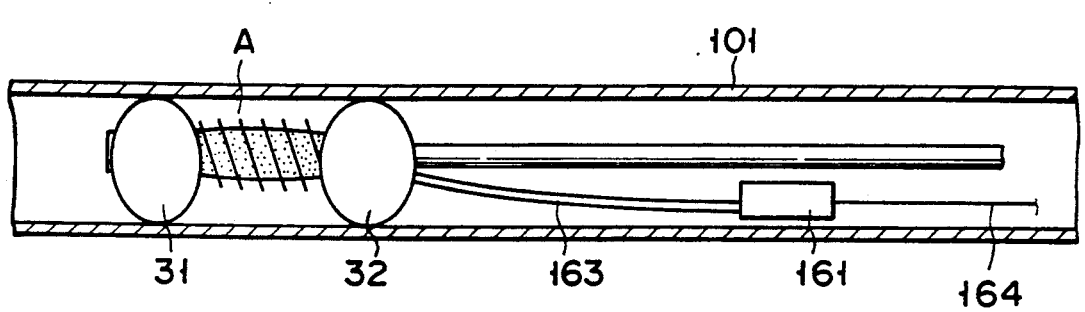
F I G. 15
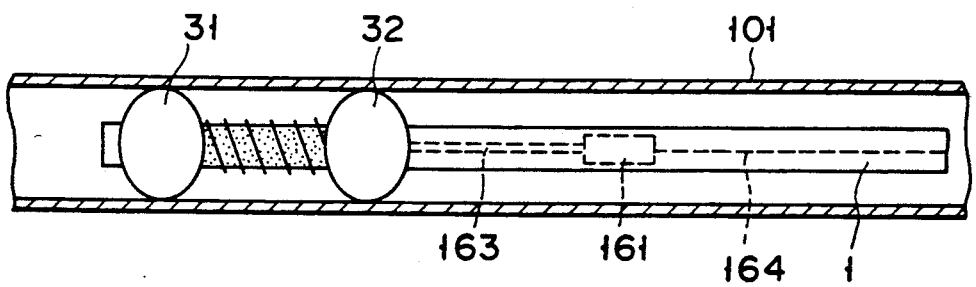
F I G. 16

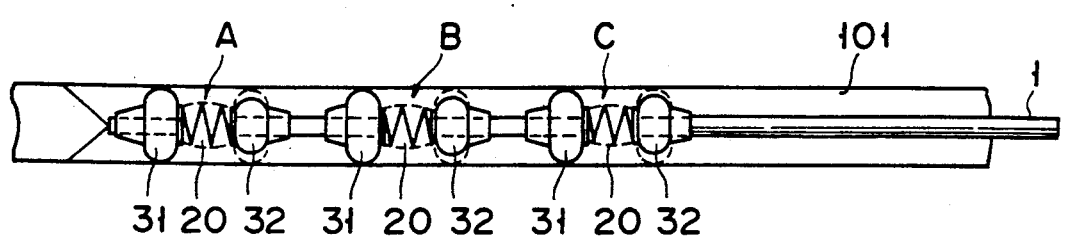
F I G. 23
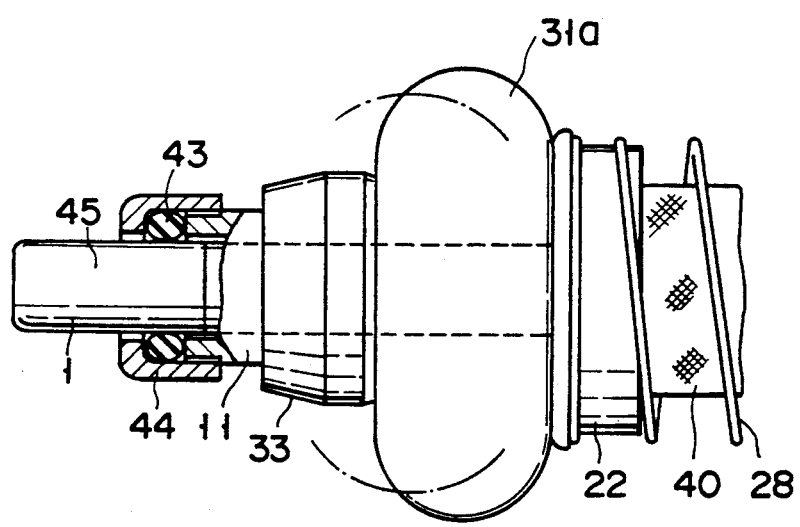
F I G. 24

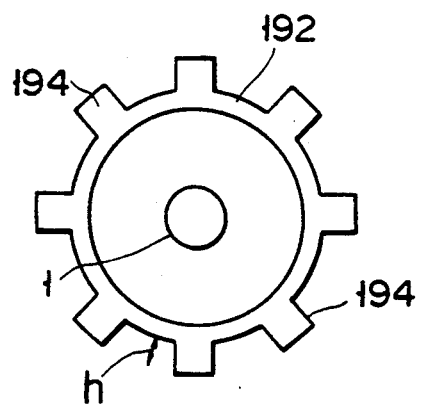
F I G. 28
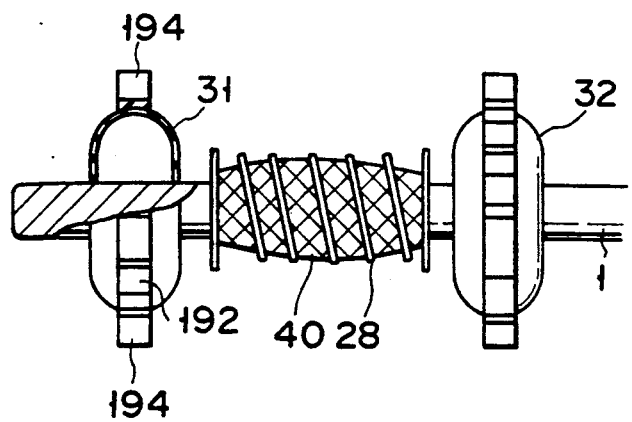
F I G. 29
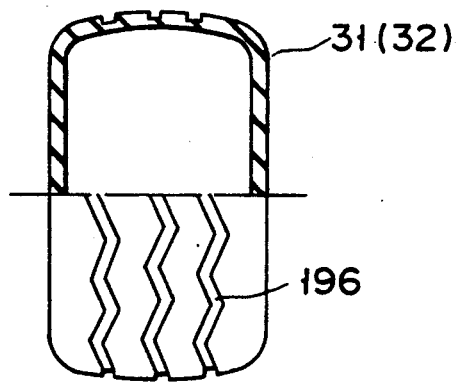
F I G. 30

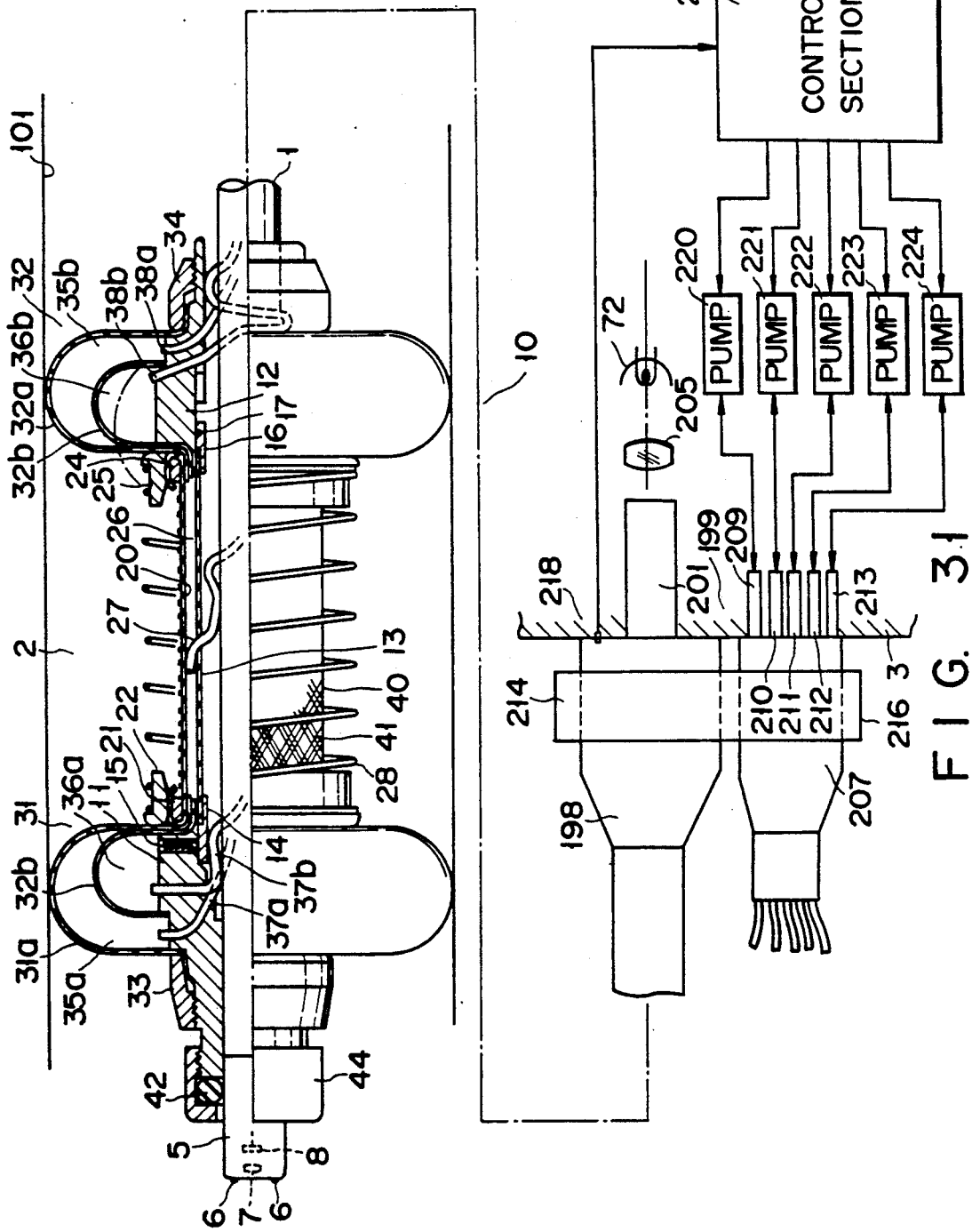
F I G. 31

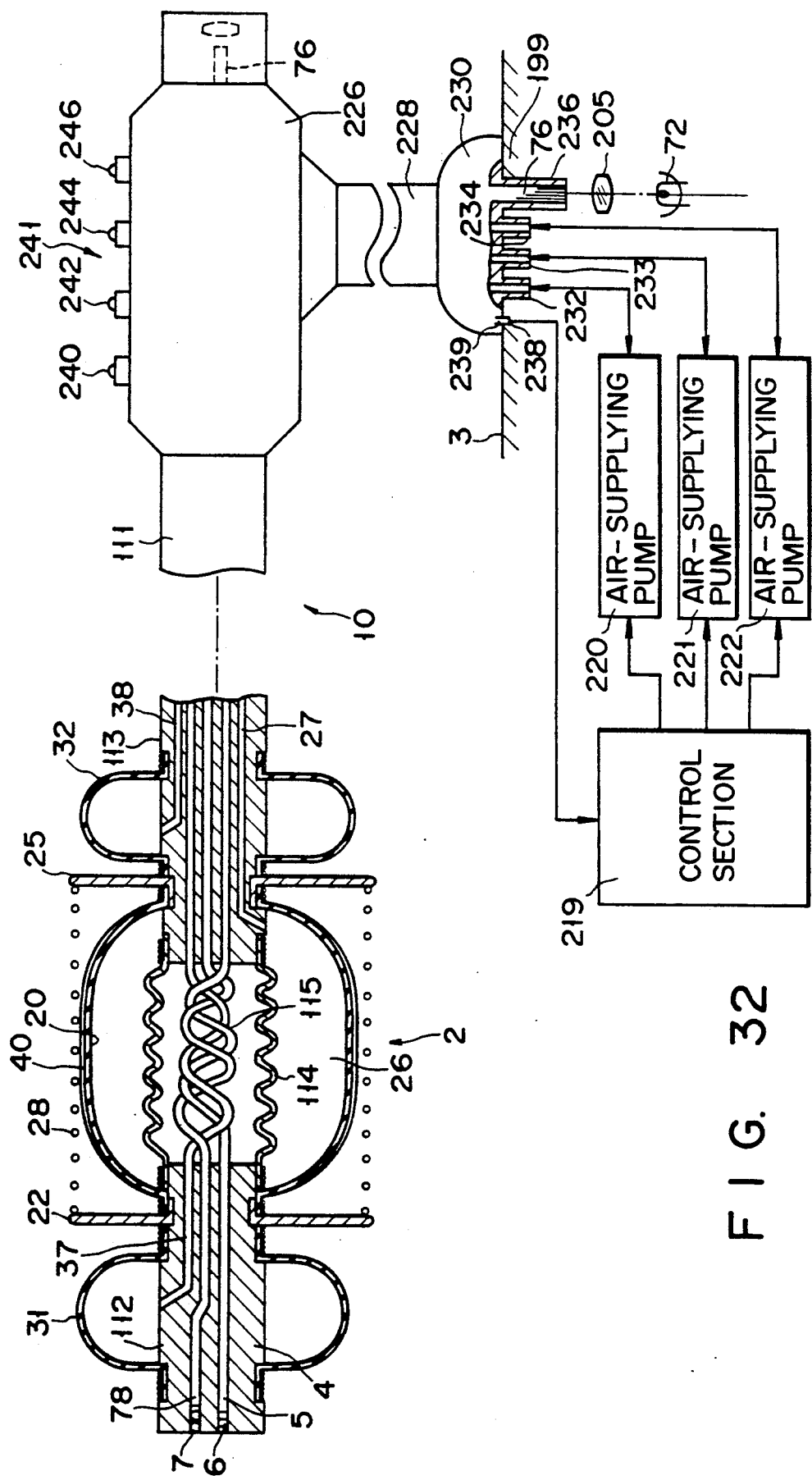
F I G. 32

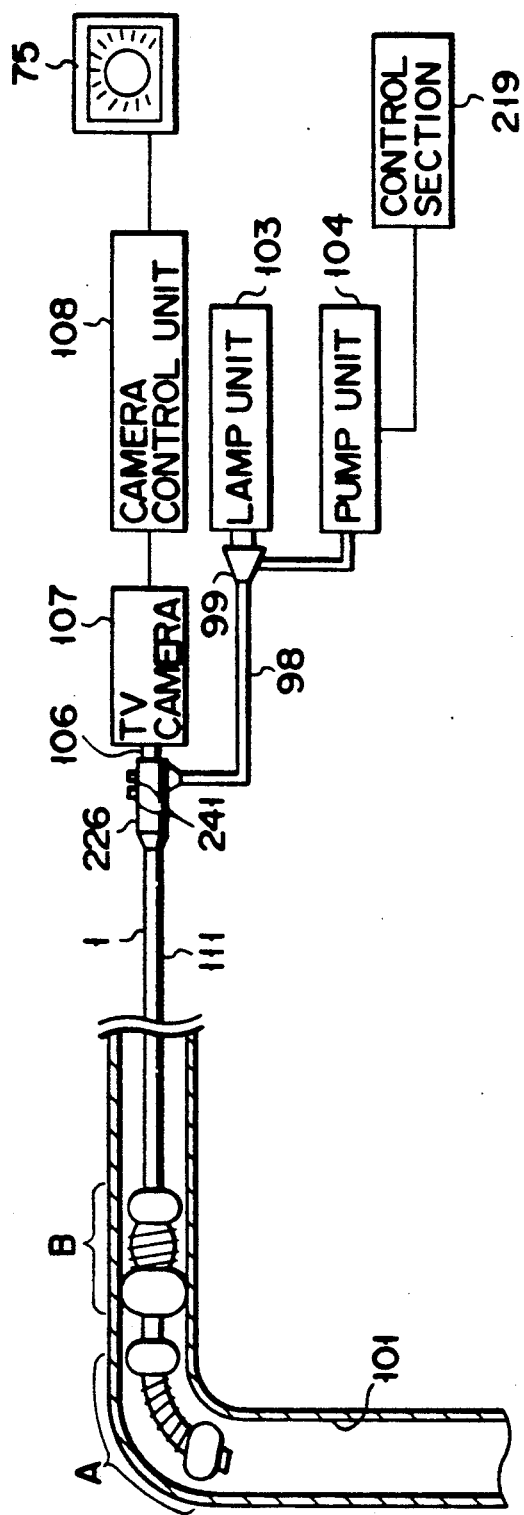
F I G. 34

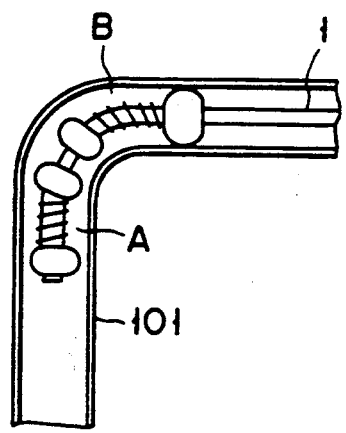 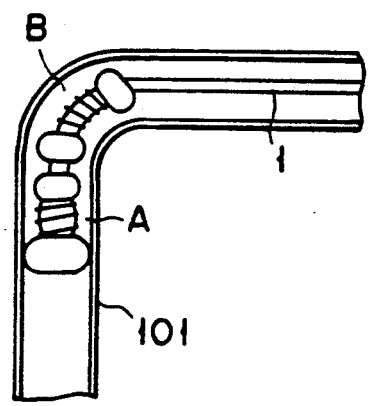
F I G. 35A　　F I G. 35B

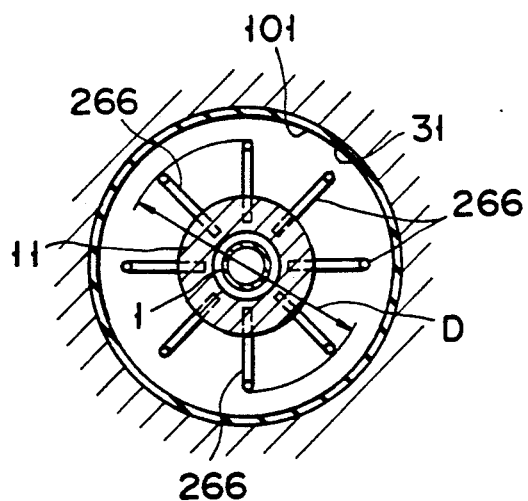
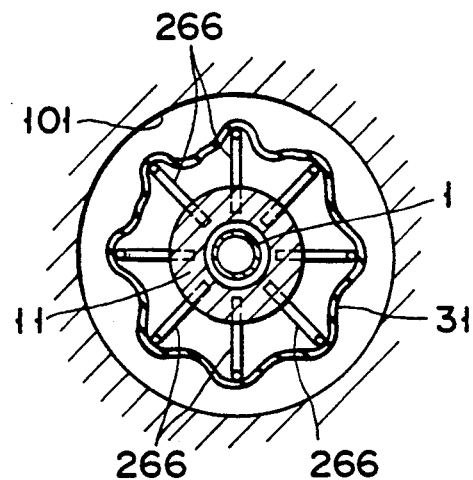
FIG. 49  FIG. 50
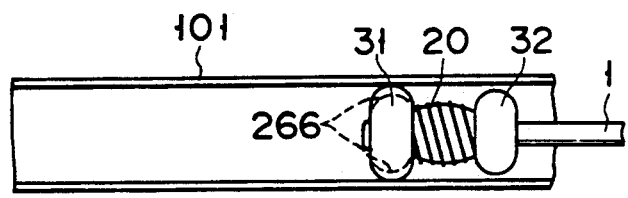
FIG. 51A
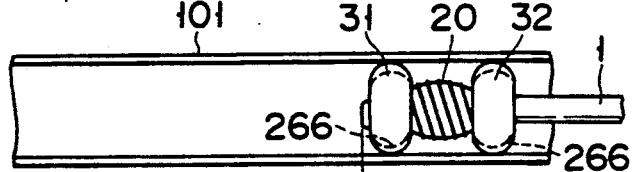
FIG. 51B
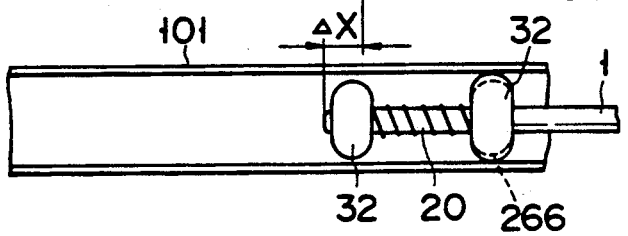
FIG. 51C

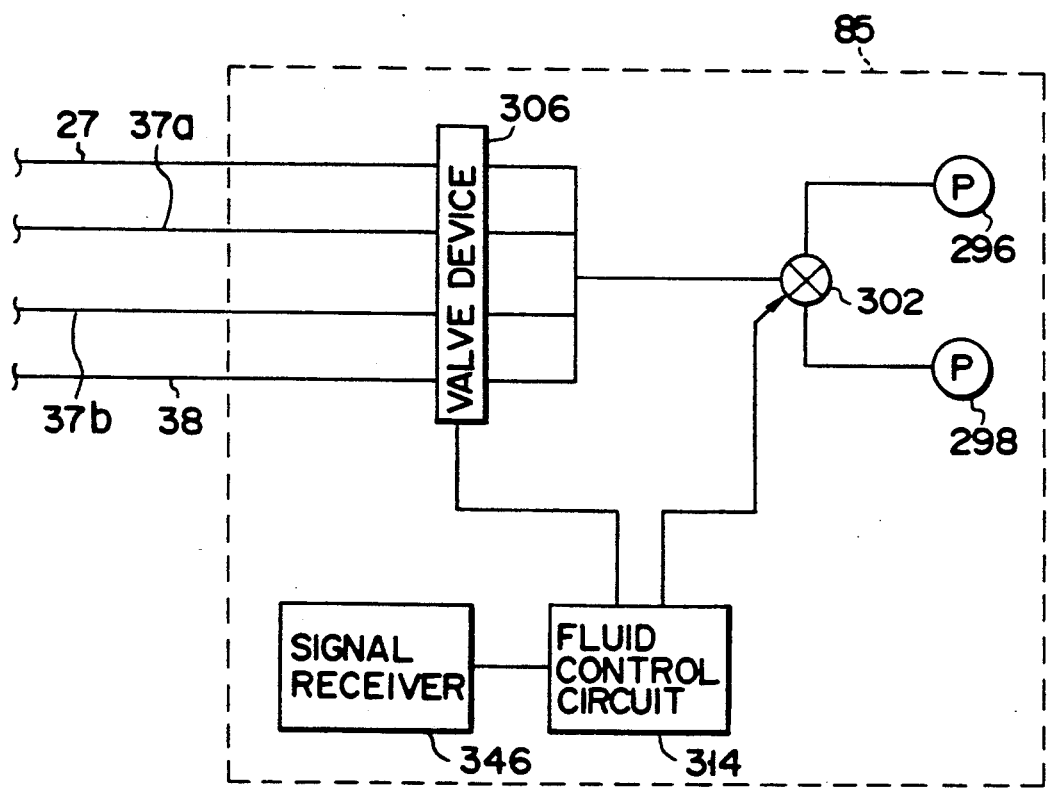
F I G. 63

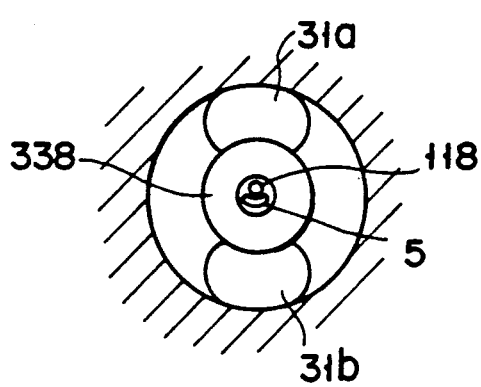
F I G. 65
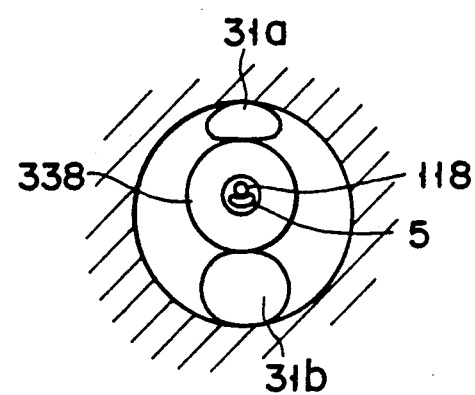
F I G. 66

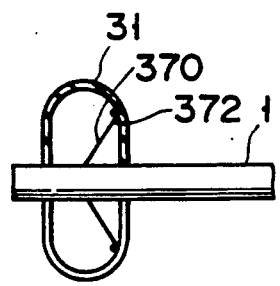
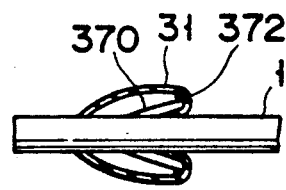
FIG. 75   FIG. 76
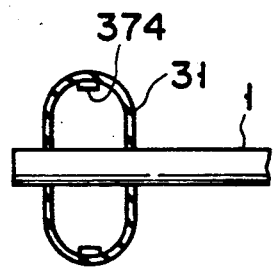
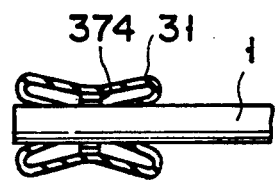
FIG. 77   FIG. 78

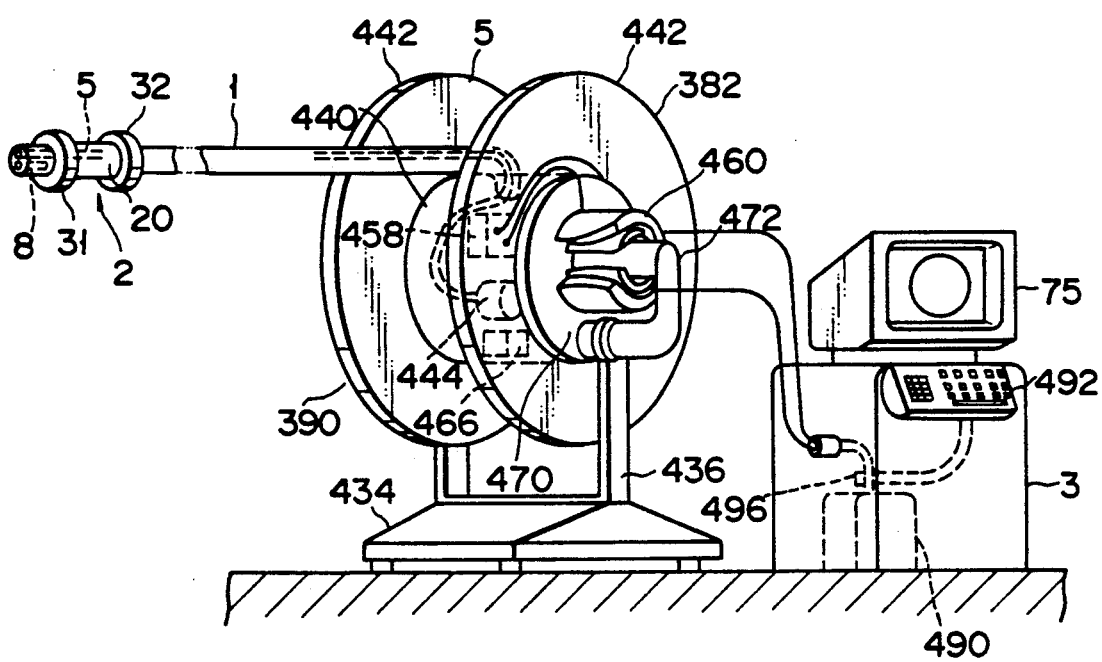
F I G. 87

PIPE-INSPECTING APPARATUS HAVING A SELF PROPELLED UNIT

This application is a continuation of application Ser. No. 07/272,007, filed Nov. 14, 1988 and now abandoned.

BACKGROUND OF THE INVENTION

1. Field of the Invention

The present invention relates to a pipe-inspecting apparatus having a self-propelled unit which can move within a pipe to inspect the interior of the pipe.

2. Description of the Related Art

Japanese Patent Publication No. 51-15678 discloses an endoscope comprising an insertion section whose middle portion is a self-propelled unit. The self-propelled unit comprises bellows made of elastic material, and two balloons coupled to the ends of the bellows. The self-propelled unit can move back and forth within a tubular member in the following way. First, the rear balloon is inflated until it pushes the inner periphery of the tubular member. As a result, the bellows is held in the tubular member. Then, pressurized air is supplied into the bellows, thus expanding the bellows forward in its axial direction. Thereafter, the front balloon is inflated until it pushes the inner periphery of the tubular member. Next, the rear balloon is deflated, and the bellows is also deflated. As a result, the self-propelled unit moves forward, pulling forward the rear end portion of the insertion section. As the balloons and the bellows are repeatedly inflated and deflated in this manner, the self-propelled unit moves forward within the tubular member, and the insertion section advances forward in the tubular member.

The self-propelled unit disclosed in Japanese Patent Publication No. 51-15678 cannot move the insertion section in a tubular member when the insertion section is relatively long and heavy. More precisely, the force of the expanding bellows is not strong enough to push the insertion section, and the force of the contracting bellows is insufficient to pull the insertion section.

SUMMARY OF THE INVENTION

The object of the present invention is to provide a a pipe-inspecting apparatus having a self-propelled unit which is powerful enough to move reliably within a pipe to inspect the interior of the pipe.

According to the present invention, there is provided a pipe-inspecting apparatus which comprises:

a self-propelled unit including:
  an elastic tube which has two ends, and into and from which a fluid is supplied and discharged;
  a restriction member mounted on the elastic tube, for restricting an axial expansion of the elastic tube;
  a bias member for biasing the elastic tube in the axial direction thereof;
  a first holding member coupled to the first end of the elastic tube, for holding the first end to the inner periphery of a pipe being inspected, while the fluid is being supplied into the first holding member, and releasing the first end from the inner periphery of the pipe, while the fluid is being discharged from the first holding member; and
  a second holding member coupled to the second end of the elastic tube, for holding the second end to the inner periphery of the pipe, while the fluid is being supplied into the second holding member, and releasing second end from the inner periphery of the tube, while the fluid is being discharged from the second holding member;

an observation device located within the self-propelled unit, for scanning the interior of the pipe;

a display device for displaying an image of the interior of the pipe which has been scanned by the observation device; and a fluid control device for supplying and discharging the fluid to and from the elastic tube and the first and second holding members.

When the fluid control device intermittently supplies the fluid to the elastic tube and the first and second holding members, and also intermittently discharge the fluid from the elastic tube and the first and second holding members, the self-propelled unit moves forward or backward in the pipe. Every time the fluid is supplied into the elastic tube, the tube expands in its axial direction. When the tube axially expands to a predetermined extent, the restriction member prevents the tube from further expanding in its axial direction. As a result, the tube starts expanding in its radial direction with contracting in the axial direction by the restriction member. When the fluid is discharged from the tube, the tube contracts in its radial direction with expanding in the axial direction by the bias member, thus generating a great pulling force and being durable. Hence, the self-propelled unit can move, both reliably and stably.

BRIEF DESCRIPTION OF THE DRAWINGS

FIG. 1A is a partially sectional view showing the self-propelled section incorporated in a pipe-inspecting apparatus according to a first embodiment of the present invention, said section including a self-propelled unit;

FIG. 1B is a diagram showing the elastic cylinder used in the self-propelled section shown in FIG. 1A;

FIG. 3 is a side view of that section of the apparatus which is placed outside a pipe to inspect;

FIG. 4 is a partially sectional view, showing a guide pulley and a guide shaft, both used in the self-propelled section;

FIG. 15 is a longitudinal, sectional view of the air-supplying pump incorporated in an eighth modification of the pipe-inspecting apparatus;

FIG. 16 is a side view showing the self-propelled device incorporated in a ninth modification of the pipe inspecting apparatus;

FIGS. 22A to 22C, and 23 are side views of the self-propelled unit, explaining how the unit moves within the pipe under inspection;

FIG. 24 is a partially sectional view showing the distal end portion of the self-propelled unit shown in FIGS. 22 and 23;

FIGS. 28 and 29 are a front view and a partially sectional side view, respectively, of the self-propelled section used in a fourth modification of the second embodiment;

FIG. 30 is a partially sectional view showing a modification of the balloons of the self-propelled unit shown in FIGS. 20 and 21;

FIG. 31 is a partially sectional side view schematically showing a pipe-inspecting apparatus according to a third embodiment of the invention;

FIG. 32 is a partially sectional side view of a modification of the third embodiment of the invention;

FIG. 34 is a side view of the pipe-inspecting apparatus according to this invention, explaining how the self-propelled unit of the apparatus moves within a bent portion of a pipe;

FIGS. 35A and 35B are side views showing the self-propelled unit of the invention, explaining how the unit moves within a bent portion of a pipe;

FIG. 49 is a cross-sectional view of the self-propelled unit, taken along line A-A in FIG. 48;

FIG. 50 is a cross-sectional view of the self-propelled unit, taken along line A—A in FIG. 48, and showing the balloon being deflated;

FIGS. 51A to 51C are side views of the self-propelled unit, showing the sequence of the movement of the unit within the pipe under inspection;

FIG. 63 is a block diagram showing the fluid-pressurizing device incorporated in the seventh embodiment;

FIGS. 65 and 66 are front views of the self-propelled unit used in the seventh embodiment;

FIGS. 75 and 76 are partially sectional side views showing the self-propelled unit incorporated in a fourth modification of the eighth embodiment;

FIGS. 77 and 78 are partially sectional side views showing the self-propelled unit incorporated in a fifth modification of the eighth embodiment;

FIG. 87 is a perspective view showing a pipe-inspection apparatus according to an eleventh embodiment of the invention;

DETAILED DESCRIPTION OF THE PREFERRED EMBODIMENTS

Figure 2:
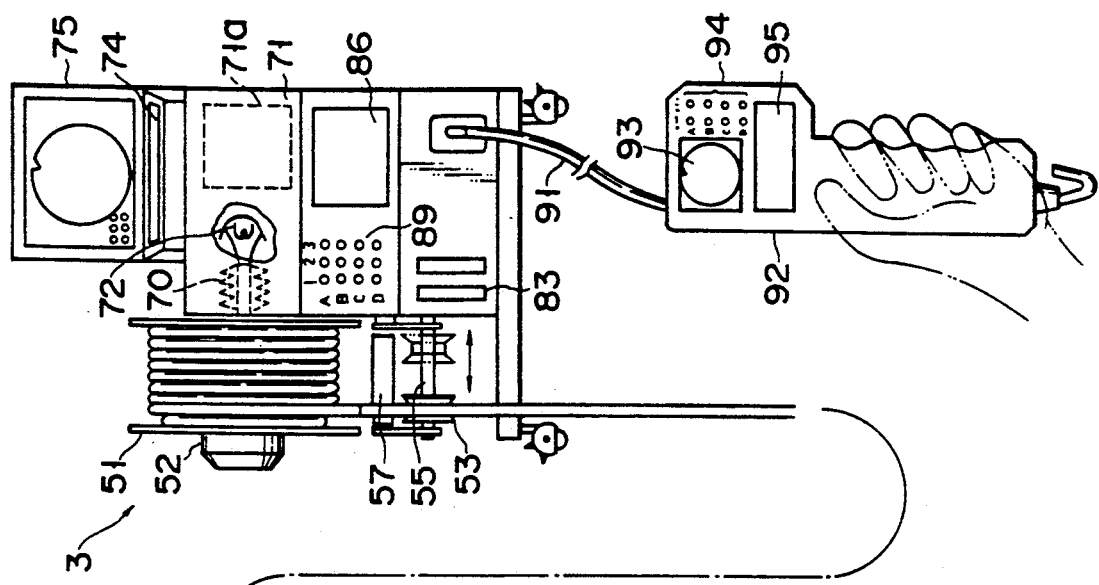
FIG. 2 is an overall view of the pipe-inspecting apparatus.
Figure 2:
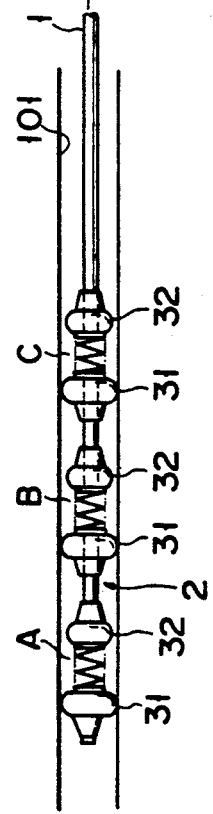
Figure 5:
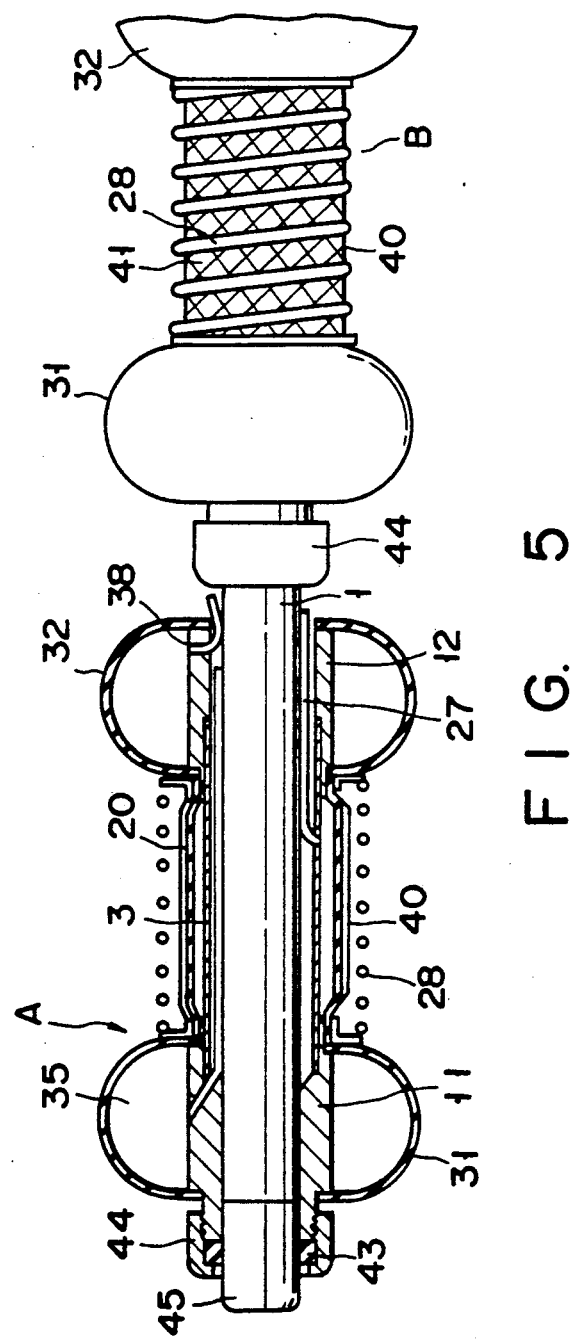
FIG. 5 is a partially sectional view showing a modification of the self-propelled unit.
Figure 6:
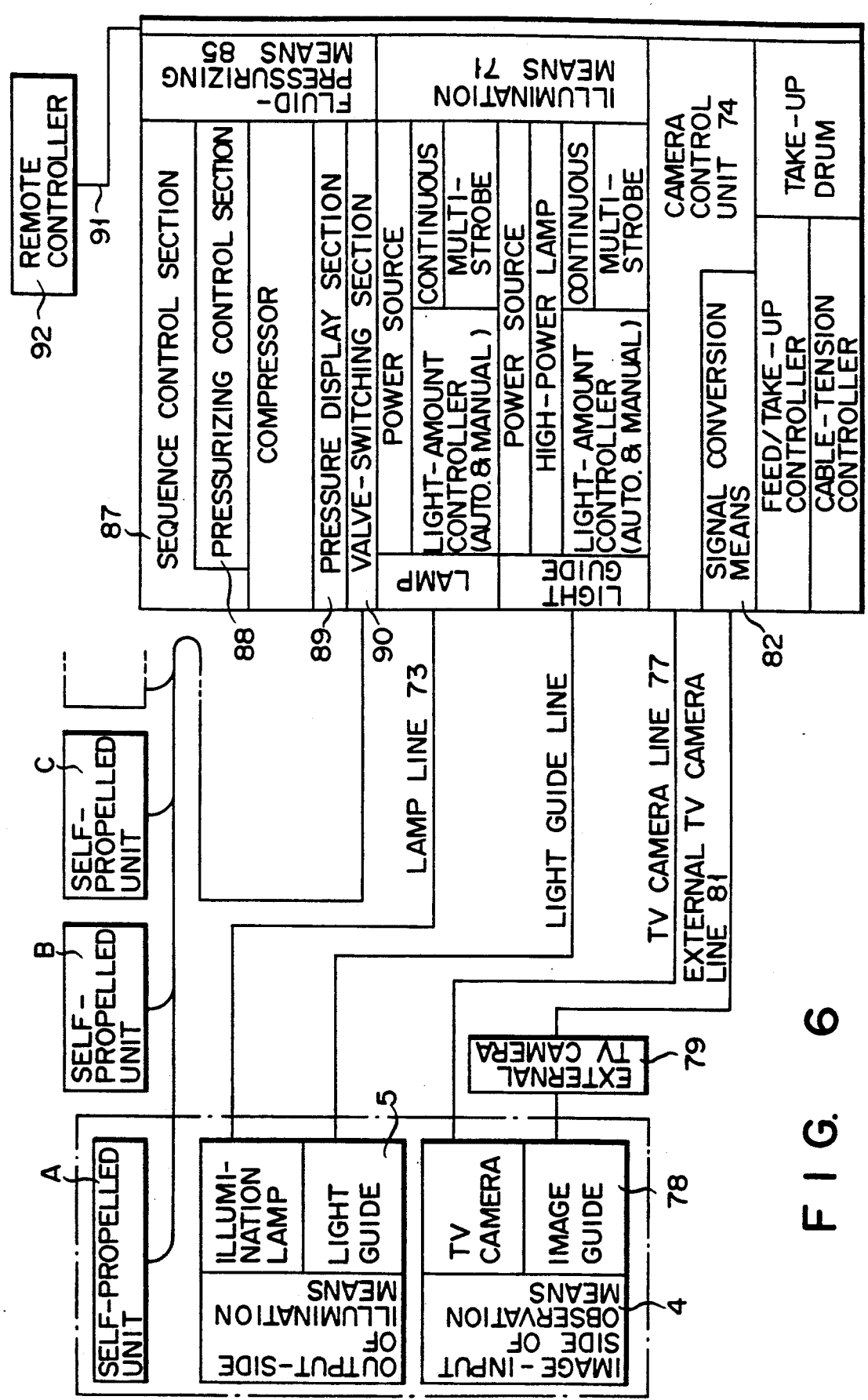
FIG. 6 is a block diagram illustrating the structure of the pipe-inspecting apparatus shown in FIG. 1.

FIG. 1 through FIG. 7 illustrate a first embodiment of the present invention, i.e., a pipe-inspecting apparatus having self-propelled units. Of these figures, FIG. 2 is an overall side view showing this apparatus, and FIG. 6 is a block diagram schematically illustrating the structure of the pipe-inspecting apparatus.

As is shown in FIG. 2, the pipe-inspecting apparatus comprises flexible cable 1, self-propelled section 2, and operation section 3. Section 2 includes self-propelled units A, B, and C—all connected to the distal end of flexible cable 1.

As can be understood from FIG. 1A, the distal end portion 4 of a bore scope is attached to the distal end of cable 1. The components of the bore scope, such as the illumination means, the observation means, and the channel (not shown), are arranged within distal end portion 4. The illumination means has light guide 5 and light-distributing lens 6. The light supplied from a light source (not shown) through light guide 5 is applied from the bore scope through lens 6. The observation means has objective lens 7 and solid-state image pickup element 8. Light guide 5 and a signal line connected at one end of image pickup element 8, and extend through cable 1 into operation section 3.

As is shown in detail in FIG. IA, each of self-propelled units A, B, and C, which are attached to the distal end of cable 1, comprises front body 11, rear body 12, inner tube 13, and connecting tubes 14 and 16. Front body 11 and rear body 12 are hollow cylinders. Inner tube 13 has some elasticity, and is made of material having a predetermined hardness. Alternatively, tube 13 can be a soft tube with a braid or a coil embedded in it. In this case, the braid may be made of stainless steel wires, and the coil is made of a long stainless-steel strip. Connecting ring 14 is attached to the distal end of inner tube 13. Both inner tube 13 and connecting ring 14 are fitted in front body 11. Connecting ring 14 is fixed in place by means of step screw 15 which is in screw engagement with a hole cut in front body 11. The other connecting ring 16 is attached to the distal end of inner tube 13. Both inner tube 13 and connecting ring 16 are fitted in rear body 12. O-ring 17 is mounted on connecting ring 16, and ring 16 can slide back and forth in rear body 12 in an airtight fashion.

Each self-propelled unit further comprises elastic tube 20 surrounding inner tube 13 and connected between front body 11 and rear body 12. Tube 20 can expand and contract. When it contracts as is shown in FIG. IA, it has the same diameter over its entire length. The front end portion of elastic tube 20 is mounted on the circumferential surface of the rear end portion of the front body 11, which has a diameter smaller than the other portion of the body 11. Fastening ring 21 is wrapped around the front end portion of tube 20, thus fastening the tube 20 to front body 11. The front end portion of tube 20 is wrapped around ring 21 and clamped between the outer circumferential surface of ring 21 and spring-seat ring 22. The rear end portion of elastic tube 20 is mounted on the circumferential surface of the front end portion of rear body 12, which has a diameter smaller than the other portion of the body 12. Fastening ring 24 is wrapped around the rear end portion of tube 20, thus fastening the tube 20 to rear body 12. The rear end portion of tube 20 is wrapped around ring 24 and clamped between the circumferential surface of ring 24 and spring-seat ring 25.

Since elastic tube 20 surrounds inner tube 13, and either tube is closed at both ends, hollow cylindrical air space 26 is provided. Air-supplying tube 27 is connected to this air space 26.

Compression coil spring 28 is interposed between spring-seat rings 22 and 25, thus biasing ring 22 forward and ring 25 rearward. Hence, in normal condition, front body 11 and rear body 12 are spaced apart from each other as is illustrated in FIG. 1A, and elastic tube 20 is in its axial expanded position and have almost the same diameter over its entire length.

Each self-propelled unit further comprises front balloon 31 and rear balloon 32. Either balloon is made of elastic material such as rubber. Balloons 31 and 32 are secured to front body 11 and rear body 12, respectively. More specifically, the rear end of front balloon 31 is fastened in airtight fashion to front body 11, along with tube 20, by means of fastening ring 21. Similarly, the front end of rear balloon 31 is fastened in airtight fashion to rear body 11, along with tube 20, by means of fastening ring 24. The front end of front balloon 31 is fastened airtightly to front body 11 by means of fastening ring 33. Similarly, the rear end of rear balloon 32 is fastened airtightly to rear body 12 by means of fastening ring 34. Hence, closed spaced 35 is provided between front balloon 31 and the outer periphery of front body 11, and closed space 36 is also provided between rear balloon 32 and the outer periphery of rear body 12. Air-supplying tubes 37 and 38 are connected to these closed spaces 35 and 35, respectively.

Restriction cylinder 40 surrounds elastic tube 20 of each self-propelled unit of self-propelled section 2. Cylinder 40 is made of elastic material and designed to restrict the axial inflation of elastic tube 20. The front and rear ends of restriction cylinder 40 are fastened to front and rear bodies 11 and 12, respectively, along with the ends of tube 20, by means of fastening rings 21 and 24. Cylinder 40 is a braided member made of filaments 41, each of which is a bundle of fibers. More precisely, filaments 41 are braided such that every four cross at points P, thus forming a parallelogram, as is illustrated in FIG. IB. That is, every four filaments 41 form a pantograph-linkage. Diagonally opposing points P, i.e., the left and right points P, are set apart in the axial direction of tube 20, and each filament 41 is inclined at an acute angle $\theta$ to the axis of tube 20. When the pantograph-linkage contacts in the axial direction of tube 20, it expends in the radial direction of tube 20. Conversely, when the pantograph-linkage expends in the axial direction of tube 20, it contracts in the radial direction of tube 20. Since each filament 41 is inclined at an acute angle 8 to the axis of tube 20, restriction cylinder restricts the axial expansion of tube 20 more greatly than the radial expansion thereof.

As can be understood from FIG. 1A, self-propelled units A, B, and C are loosely mounted on cable 1. Nonetheless, front body 11 of each self-propelled unit is fastened to the distal end portion 4 of the bore scope by a plurality of stop screws 42, whereas rear body 12 is loosely mounted on distal end portion 4. Alternatively, as is shown in FIG. 5, O-ring 43 can be mounted in the distal end portion 45, and fastening ring 44 can clamp and deforms 0-ring 43, thereby fastening O-ring 43 to the distal end portion 45 of cable 1.

As has been mentioned, front body 11 of each self-propelled unit is fastened to the distal end portion 4 of the bore scope. Instead, rear body 12 of each self-propelled unit can be fixed to distal end portion 4 by means of screws, while front body 11 is loosely mounted on distal end portion 4. In this case, first, rear balloon 32 is inflated, thus holding the rear end of the self-propelled unit in tubular member 101, then front balloon 31 is inflated, thereby holding the front end of the unit, next rear balloon 32 is deflated, thus releasing the rear end of the unit, and finally air supplied into tube 20, thus contracting tube 20 in its axial direction against the force of spring 28. As a result, the rear end of the unit is moved forward.

The proximal end portion of cable 1 is guided to operation section 3, and is taken up around drum 51 of section 3. As is shown in FIG. 2, drum 51 is coupled to motor 52 which can be stopped by operating a brake (not shown). Hence, drum 51 can be driven, thereby to feed cable 1 or takes it up. Guide pulley 53 guides cable 1 as cable 1 is fed from drum 51 or taken up around drum 51. Guide pulley 53 is rotatably and slidably mounted on guide shaft 55 which is supported by arms 54. Lever 56, which can rotate around the axis of guide shaft 55, is pivotally coupled to arms 54. Support roller 57, which supports cable 1 and prevents it from falling, is fastened to the free end of lever 56. This lever 56 pushes cable 1 upward when cable 1 is taken up around drum 51 or fed from drum 51. Cable 1 first passes, contacting the upper part of the circumferential surface of roller 57, then is guided by the lower part of the circumferential surface of guide pulley 53, and finally is taken up around drum 51. Angle detector 58, which is connected to arms 54, detects the rotated angle of the arms 54. Whenever cable 1 slackens, arms 54 rotates to straighten cable 1. More precisely, arms 54 rotate counterclockwise to exert a moderate tension on cable 1 while cable 1 is being taken up around drum 51, and rotate clockwise to exert a moderate tension while cable 1 is being fed from drum 51.

As is illustrated in FIG. 4, guide pulley 53 is coupled to guide shaft 55 by means of bearing assembly 61. Bearing assembly 61 consists of inner ring 62 slidably mounted on shaft 55, and outer ring 63 fixed on ring 62 and having curved outer circumferential surface. The curved circumferential surface of outer ring 63 contacts guide pulley 53. Hence, guide pulley 53 can move in either direction of arrow (a), and can incline in either direction of arrow (b). Therefore, as cable 1 is taken up around drum 51 or fed from drum 51, guide pulley 53 can slide on shaft 55 and rotate, thereby to guide cable 1 smoothly.

The proximal end of cable 1 is fastened in the casing of light-source device 71, and is opposed to lamp 72 of an illumination-light source device. That is, cable 1 is optically connected to the illumination-light source means. Radiation fins 70 are mounted on input end portion of cable 1, for radiating heat from cable 1. The illumination-light source means includes control section 71a for controlling lamp 72, thereby changing the amount of light to supply through cable 1 and also the timing of supplying light via cable 1. Control section 71a can be operated, either manually or automatically. Lamp 72 is an ordinary one, a multi-strobe lamp, or the like. A lamp may be provided to the distal end portion 4 of the bore scope, for illuminating objects to observe through the bore scope. If this is the case, two requirements must be satisfied. First, power-supplying lines (i.e., distal-end lamp lines 73) must be used, extending through cable 1. Second, the lamp must be connected to control section 71a by the power-supplying lines. Also in this case, control section 71a can be operated, either manually or automatically.

Image processor 74 (including a camera control unit, etc.) and TV monitor 75 are incorporated in operation section 3. A is shown in FIG. 6, image processor 74 is connected to solid-state image pickup device 8 by TV camera line 77 which extends through cable 1. Solid-state image pickup device 8 is located within the distal end portion 4 of the bore scope as is shown in FIG. 1A. Image processor 74 is designed to covert the image signals output by device 8 into video signals. Image guide 78 extends from distal end portion 4 to operation section 3 through cable 1. The proximal end of image guide 78 is connected to an external TV terminal. External TV terminal is located in the objective-lens section of the bore scope, and is connected to signal conversion means 82 by external camera line 81. Signal conversion means 82 is connected to image processor 74. Hence, when external TV camera 79 is attached to the external TV terminal, the image signals output by the external TV camera can be supplied to image processor 74 through external TV camera line 81 and signal conversion means 82, thereby to monitor the pictures taken by external TV camera 79. Although not shown in FIG. 6, video recording disk, recording means such as a VCR, and the like are also incorporated in operation section 3.

Fluid-pressurizing means 85 is incorporated in operation section 3. Means 85 includes a fluid-pressurizing pump, valve-switching section 90, sequence control section 87, pressurizing control section 88, pressure display section 89, and the like. Valve-switching section 90 is designed to supply air to air-supplying tube 27, air-supplying tube 37, or air-supplying tube 38. Pressure sensor 89 displays the pressures detected by the sensors provided in the various tubes. Valve-switching section 90 is, for example, a servo-valve.

Operation section 3 can be remote-controlled. More specifically remote controller 92 is connected to section 3 by remote cable 91. Remote controller 92 has monitor screen 93, buttons 94 for controlling self-propelled units A, B, and C, control panel 95, and the like.

The operation of the pipe-inspecting apparatus described above will now be explained. First, it will be described how the apparatus is operated to move self-propelled section 2 forward in a tubular member 101 which is to be inspected. Self-propelled units A, B, and C of section 2 operate in the same way. Therefore, the following description will relate mainly to the most forward unit A.

Self-propelled unit A moves forward as air is supplied into elastic tube 20 via air-supplying tube 27 into, and discharged from, front balloon 31 via air-supplying tube 37, and into rear balloon 32 via air-supplying tube 38, at specific times. The timing of supplying and discharging air into and from self-propelled units A, B, and C is shown in the following Table 1, wherein [1] means the supplying of air, and [0] means the discharging of air.

TABLE 1

| | | Action 1 | Action 2 | Action 3 | Action 4 |
|---|---|---|---|---|---|
| A | Balloon 31 | 11100 | 11100 | 11100 | 11100 |
| | Balloon 32 | 00111 | 00111 | 00111 | 00111 |
| | Tube 20 | 01110 | 01110 | 01110 | 01110 |
| B | Balloon 31 | 11100 | 11100 | 11100 | 11100 |
| | Balloon 32 | 00111 | 00111 | 00111 | 00111 |
| | Tube 20 | 01110 | 01110 | 01110 | 01110 |
| C | Balloon 31 | 11100 | 11100 | 11100 | 11100 |
| | Balloon 32 | 00111 | 00111 | 00111 | 00111 |
| | Tube 20 | 01110 | 01110 | 01110 | 01110 |

In the first step of action 1, front balloon 31 is inflated, while rear balloon 32 and elastic tube 20 are deflated. In other words, only front balloon 31 is inflated as is shown in FIG. 2. Balloon 31 contacts in the inner surface of tubular member 101, and is thus held in tubular member 101. At this time, rear balloon 32 is not inflated and spaced apart from the inner surface of tubular member 101, and elastic tube 20 extends over its own entire length since air is not supplied into it.

Figures 7A, 7B, 7C:
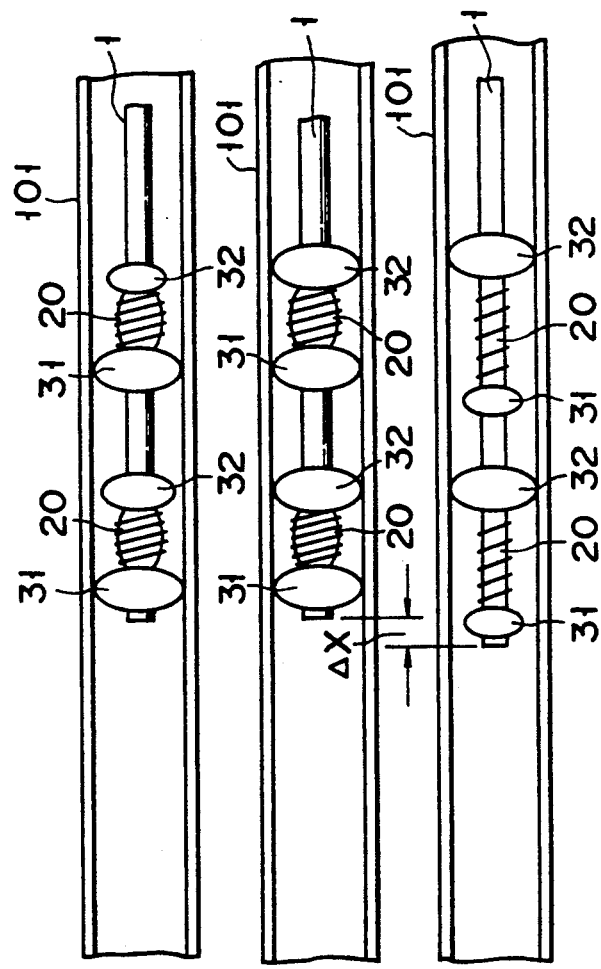
FIGS. 7A to 7C are side views of the self-propelled unit, explaining how the unit moves in the pipe under inspection.

In the second step of action 1, air is supplied into tube 20, and tube 20 intends to extends in its axial direction. However, restriction cylinder 40 prevents elastic tube 20 from expanding in its axial direction. Rather, tube 20 contracts in its axial direction in the following manner. As air is supplied into tube 20, tube 20 expands in its radial direction, whereby the pantograph-linkage formed of every four filaments 41 expands in the vertical direction (FIG. 1B), and contracts in the horizontal direction, i.e., the axial direction of elastic tube 20. As a result, elastic tube 20 pulls rear body 12 toward front body 11 as is shown in FIG. 7A. In other words, rear body 12 is moved forward to the position indicated by broken lines in FIG. 1A, sliding on the outer surface of inner tube 13. In the second step of action 1, front body 11 is held in position since front balloon 31 still inflated and fixed in position in tubular member 101.

In the third step of action 1, air is supplied into rear balloon 32. Hence, not only front balloon 31 and elastic tube 20, but also rear balloon 32 is inflated. Rear balloon 32 also contacts the inner surface of tubular member 101, as is shown in FIG. 7B.

In the fourth step of action 1, air is discharged from front balloon 31 and air space 26 of elastic tube 20. As a result, compression spring 28 straightens elastic tube 20, whereby front body 11 is moved forward to the position shown in FIG. 7C. As front body 11 moves forward, cable 1 and distal end portion 4 of the bore scope also move forward. Hence, self-propelled section 2 moves forward for distance Δx. Thus, action 1 is completed.

Therefore, action 2, action 3, and action 4, which are identical with action 1, are carried out, whereby self-propelled section 2 moves forward by distance Δx in each action. Since self-propelled units A, B, and C simultaneously perform actions 1, 2, 3, and 4, section 2 moves with a force three times greater than in the case where it has only one self-propelled unit.

To move self-propelled section 2 backward in the tubular member 101, it suffices to supply and discharge air into and from self-propelled units A, B, and C with the timing specified in the following table 2. As can be understood from Table 2, this timing is reverse to that shown in Table 1.

TABLE 2

| | | Action 1 | Action 2 | Action 3 | Action 4 |
|---|---|---|---|---|---|
| A | Balloon 31 | 00111 | 00111 | 00111 | 00111 |
| | Balloon 32 | 11100 | 11100 | 11100 | 11100 |
| | Tube 20 | 01110 | 01110 | 01110 | 01110 |
| B | Balloon 31 | 00111 | 00111 | 00111 | 00111 |
| | Balloon 32 | 11100 | 11100 | 11100 | 11100 |
| | Tube 20 | 01110 | 01110 | 01110 | 01110 |
| C | Balloon 31 | 00111 | 00111 | 00111 | 00111 |
| | Balloon 32 | 11100 | 11100 | 11100 | 11100 |
| | Tube 20 | 01110 | 01110 | 01110 | 01110 |

Figure 8:
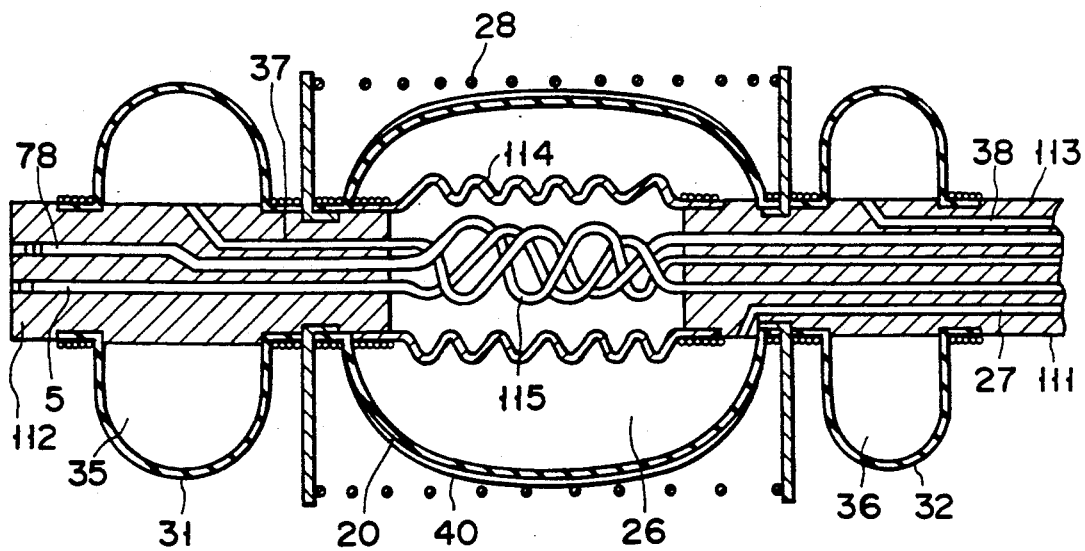
FIG. 8 is a longitudinal, sectional view of the self-propelled section incorporated in a first modification of the pipe-inspecting apparatus.

FIG. 8 shows a first modification of the first embodiment of the present invention. This modification is characterized in that a self-propelled unit is provided within the insertion section 111 of a bore scope. More specifically, insertion section 111 comprises distal-end member 112, and proximal-end portion 113 spaced apart from member 112, and bellows 114 connecting member 112 and portion 113. Elastic tube 20 surrounds bellows 114 and is coupled at one end to member 112, and at the other end to portion 113. Further, hollow restriction cylinder 40 surrounds tube 20 and is connected at one end to member 112, and at the other end to portion 113. Front balloon 31 is fastened to distal-end member 112, and rear balloon 32 is fastened to proximal-end portion 113. Air-supplying tube 27 extends into air space 26 of elastic tube 20. Air-supplying tubes 37 and 38 extend into the air space 35 of balloon 31 and the air space 36 of balloon 32, respectively. Air-supplying tubes 27, 37, and 38 pass through insertion section 111 and connected to operation section 3 (not shown in FIG. 8). When the self-propelled section of the modified pipe-inspecting apparatus is operated in the same way as the first embodiment, it moves forward or backward within a tubular member.

The first modification of the first embodiment also comprises image guide 78 for transmitting light from an observation means to an objective-lense section or the like incorporated in operation section 3. Light guide 5, air-supplying tube 37, and image guide 78 have a slack and meandering portion 115 each. The slack portions 115 of these tubes 5 and 37 and image guide 78 are located between distal-end member 112 and proximal-end portion 113. Due to these slack portion 115, no excessive tension is applied on tube 5 or 37, or no image guide 78 when bellows 114 is inflated and expands in its axial direction to move member 112 or portion 113 either forward or backward.

Figure 9:
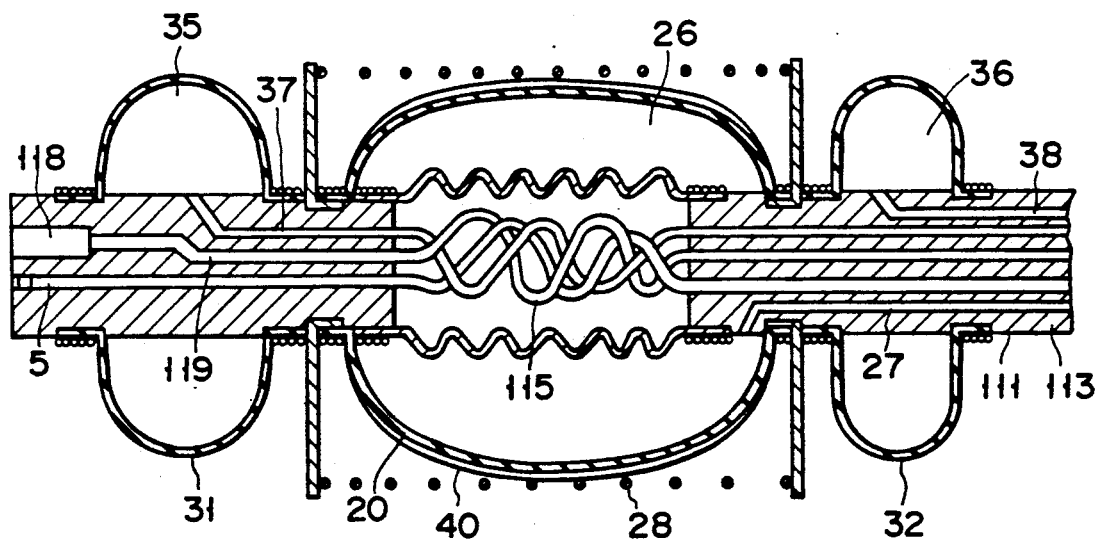
FIG. 9 is a longitudinal, sectional view of the self-propelled section incorporated in a second modification of the pipe-inspecting apparatus.

FIG. 9 shows a second modification of the first embodiment of the present invention. In the second modification, as in the first modification (FIG. 8), a self-propelled unit is provided within the insertion section 111 of a bore scope. This modification is characterized in that TV camera 118, which functions as an observation means, is located within the distal-end portion 112 of insertion section 111. Signal cord 119 is connected to TV camera 118. Cord 119 has a slack and meandering portion 115 which is located between distal-end member 112 and proximal-end portion 113.

Figure 10:
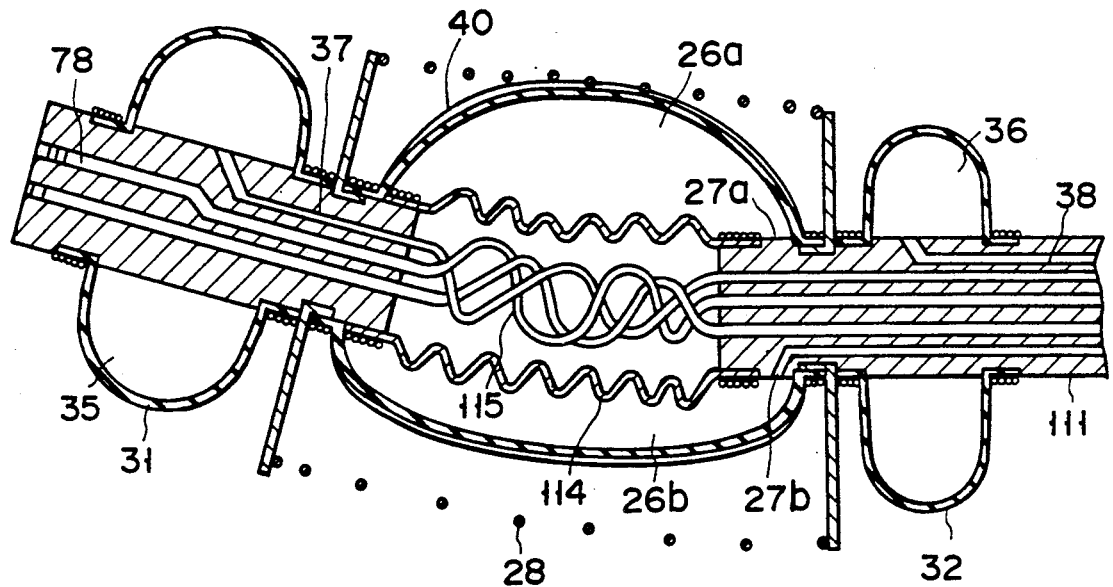
FIG. 10 is a longitudinal, sectional view of the self-propelled section incorporated in a third modification of the pipe-inspecting apparatus.

FIG. 10 shows a third modification of the first embodiment of the present invention. The second modification is identical to the first modification (FIG. 8), except, that air space 26 defined by elastic tube 20 is partitioned into two parts, i.e., upper chamber 26a and lower chamber 26b, and two air-supplying tubes 27a and 27b are connected to chambers 26a and 26b, respectively. (According the present invention, space 26 may be divided into three or more chambers.) Hence, when more air is supplied into upper chamber 26a than into lower chamber 26b, or air is supplied into chamber 26a only, the self-propelled unit is bent as is shown in FIG. 10. In order to move the self-propelled unit forward or backward in tubular member 101, it suffices to supply and discharge air into and from chambers 26a and 26b in the same amount.

With the third modification shown in FIG. 10, it is possible for only one of self-propelled units A, B and C, which is located within a bent portion of tubular member 101, to bend and hence smoothly pass through the bent portion of member 101.

Figure 11:
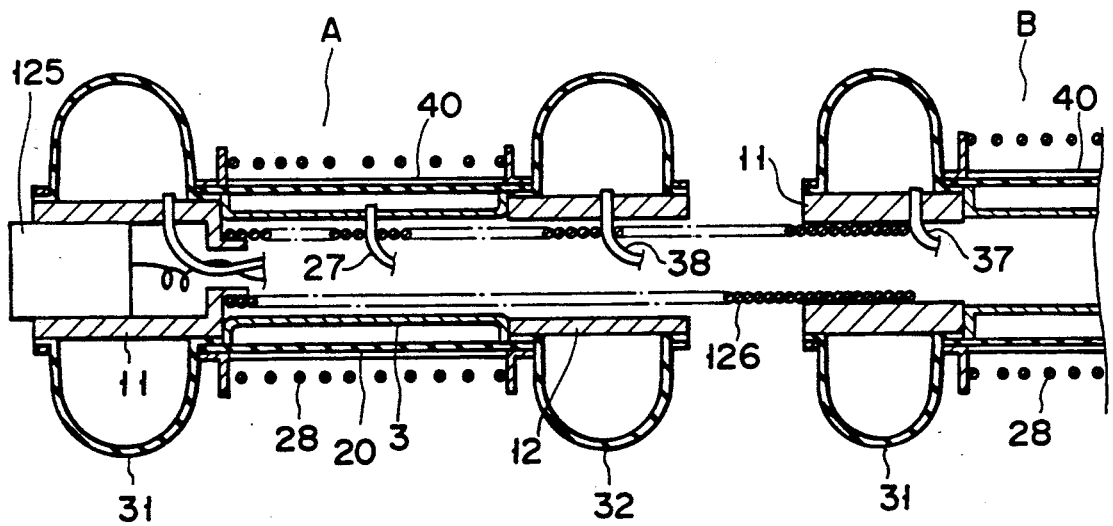
FIG. 11 is a longitudinal, sectional view of the self-propelled section used in a fourth modification of the pipe-inspecting apparatus.

FIG. 11 illustrates a fourth modification of the first embodiment of the invention. This modification is characterized in that TV camera 125, not a bore scope, is located within the most forward self-propelled unit A. (TV camera 125 includes an illumination device, a light guide, and the like.) Self-propelled unit A is coupled to self-propelled unit B by means of flexible shaft 126 which is a densely wound coil. The distal end of flexible shaft 126 is secured to front body 11 which supports front balloon 31. Therefore, front body 11, unit A does not bend downward despite of TV camera 125 which is considerably heavy.

Figure 12:
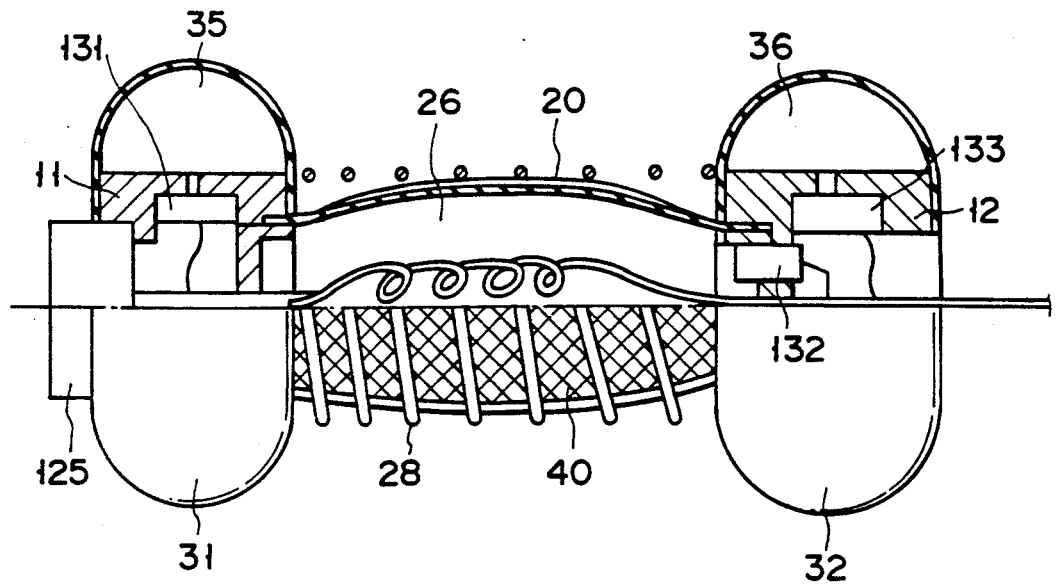
FIG. 12 is a partially sectional view of the self-propelled section incorporated in a fifth modification of the pipe-inspecting apparatus.

FIG. 12 shows a fifth modification of the first embodiment. The fifth modification is characterized in that pumps 131, 132, and 133 are arranged within self-propelled units A, B, and C, respectively. These pumps 131, 132, and 133 supplies air into the air space 26 of elastic tube 20, the closed spaces 35 defined by balloon 31, and the closed space 36 defined by balloon 32. Since pumps 131, 132, and 133 communicate directly with spaces 26, 35, and 36, respectively, air-supplying tubes 27, 28, and 29 are no longer necessary. Thus, no air-supplying tubes extend through cable 1, and cable 1 can be thinner than in the case of the first to fourth modifications.

Figure 13:
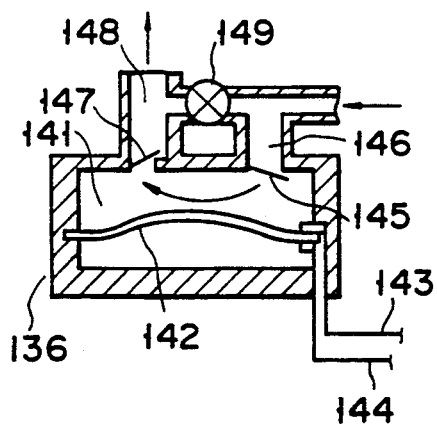
FIG. 13 is a partially sectional view of the air-supplying pump incorporated in a sixth modification of the pipe-inspecting apparatus.

FIG. 13 illustrates a sixth modification of the first embodiment of the invention. The sixth modification is identical to the fifth modification, except that pumps 131, 132, and 133 arranged within units A, B, and C, respectively, are bimorph pumps of the same structure. As is shown in FIG. 13, bimorph pump 136, for example, comprises pump chamber 141, bimorph membrane 142 partitioning chamber 141 into two sub-chambers, i.e., an upper chamber and a lower chamber, lead wires 143 and 144 connected to membrane 142. As a voltage is repeatedly applied on membrane 142 through lead wires 143 and 144, bimorph membrane 142 vibrates such that air flows into the upper sub-chamber through inlet port 146 and is then pumped from the upper sub-chamber through outlet port 148 into the air space 26 defined by elastic tube 20, the air space 35 defined by balloon 31, and the air space 36 defined by balloon 32. Solenoid valve 149 is located in the passage connecting inlet port 146 and outlet port 148. When solenoid valve 149 is opened, the air is discharged into the atmosphere from air spaces 26, 35, and 36.

Figure 14:
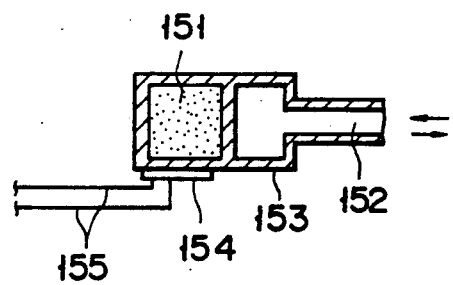
FIG. 14 is a longitudinal, sectional view of the air-supplying pump incorporated in a seventh modification of the pipe-inspecting apparatus.

FIG. 14 illustrates a seventh modification of the first embodiment of the invention. The sixth modification is identical to the fifth modification, except that pumps 131, 132, and 133 arranged within units A, B, and C, respectively, are pumps having a mass of hydrogen storage alloy. More specifically, as is shown in FIG. 14, each pump comprising case 153 having two chambers and outlet port 152 communicating with the first chamber, a mass of hydrogen storage alloy 151 packed within the second chamber, Peltier element 154 attached to the outer surface of the second chamber for heating the mass of alloy 151, and two lead wires 155 connected to Peltier element 154. When a voltage is applied to Peltier element 154 via lead wires 155, element 154 generates heat, thus heating the mass of hydrogen storage alloy 151. As a result, the mass of alloy 151 releases hydrogen gas. When Peltier element 154 is cooled, the mass of alloy 151 absorbs the hydrogen gas. Hence, element 154 functions as a pump for supplying hydrogen gas into air spaces 26, 35, and 36 and discharging the hydrogen gas therefrom.

FIG. 15 shows an eighth modification of the first embodiment of the invention. In the eighth modification, air-pressurizing pump 161 is located behind each self-propelled unit (only unit A shown in FIG. 15) and coupled to the self-propelled unit by means of air-supplying tube 163. Cable 164 is coupled to pump 161 for actuating pump 161. Since pump 161 is coupled to the self-propelled unit by tube 163, it moves forward as the self-propelled unit moves in a tubular member 101.

FIG. 16 illustrates a ninth modification of the first embodiment. In this modification, air-pressurizing pump 161 is incorporated in cable 1 (or the insertion section of a bore scope) and is connected to each self-propelled unit by air-supplying tube 163 which extends through cable 1. Cable 164 extends through cable 1 (or the insertion section of the bore scope) and coupled to pump 161 for actuating pump 161.

In the self-propelled section of the tube-inspecting apparatus according to the first embodiment of this invention, a suction pump can be used to discharge air forcedly from elastic tube 20 and balloons 31 and 32 each self-propelled unit immediately after tube 20 and balloons 31 and 32 have been inflated. If this is the case, every self-propelled unit can move forward or backward at high speed.

Still further, both balloons 31 and 32 of each self-propelled unit may be designed so as to function in the same way as restriction cylinder 40, in which case cylinder 40 can be dispensed with.

Figure 17:
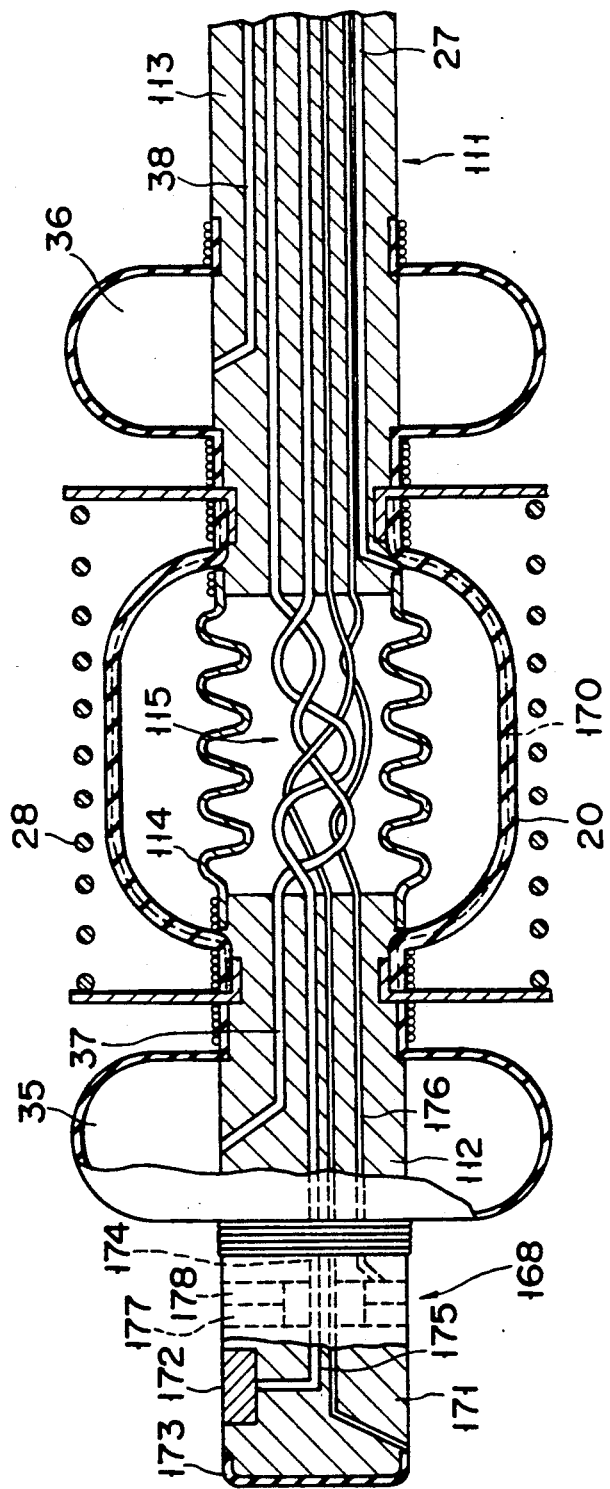
FIG. 17 is a longitudinal, sectional view of the self-propelled device incorporated in a tenth modification of the pipe-inspecting apparatus.
Figure 18:
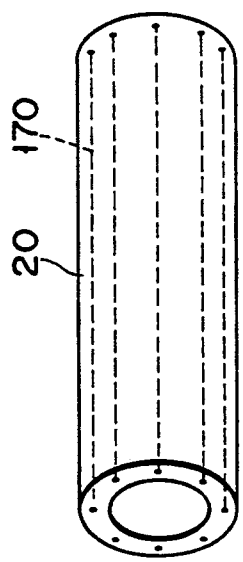
FIG. 18 is a perspective view of the elastic tube used in the self-propelled device shown in FIG. 17.

FIGS. 17 and 18 illustrate a tenth modification of the first embodiment of the present invention. As is shown in FIG. 17, ultrasonic-wave motor 168, which is generally a hollow cylinder, is attached to the distal end of distal-end member 112, and rotary member 171 is coupled to ultrasonic-wave motor 168. Eddy current probe 172 is embedded in the surface of rotary member 171; it is employed in place of an observation device such as a TV camera. Eddy current probe 172 can effectively detect cracks made in the inner surface of a tubular member 101. Pressure-sensitive cover 173 made of electro-conductive rubber is bonded to the distal end of rotary member 171. The higher the pressure applied to cover 173, the more the resistivity of cover 173 decreases. Hence, cover 173 is used as a sensor for sensing a contact between rotary member 171 and anything else. Eddy current probe 172, pressure-sensitive cover 173, and ultrasonic-wave motor 168 are connected to signal lines 174, 175, and 176, respectively. These signal lines 174, 175, and 176, and air-supplying tube 37 have slack portions 115, which are located between distal-end member 112 and proximal-end section 113. A bias means for moving probe 172 may be provided to distal-end member 112. The bias means moves probe 172 toward and from the inner surface of member 101, and also keeps probe 172 out of contact with member 101, thereby to increase the accuracy of detection.

As is shown in FIG. 17, ultrasonic-wave motor 168 comprises rotor 177 and stator 178. Rotor 177 can rotate, whereas stator section 178 is fixed in place. Rotary member 171 is fixed to rotor 177, whereas distal-end member 112 is fastened to stator 178. Thus, when ultrasonic-wave motor 168 is driven, that is, when rotor 177 rotates, rotary member 171 rotates, while distal-end member 112 does not. Signal line 176 connects motor 168 to the driver (not shown) incorporated in operation section 3. The driver supplies control signals to motor 168 through signal line 176, thereby driving motor 168. Also, signal lines 174 and 175 connect eddy current probe 172 and pressure-sensitive cover 173 to the signal-processing device (not shown) incorporated in operation section 3. This signal-processing device is connected to TV monitor 75.

Figure 19:
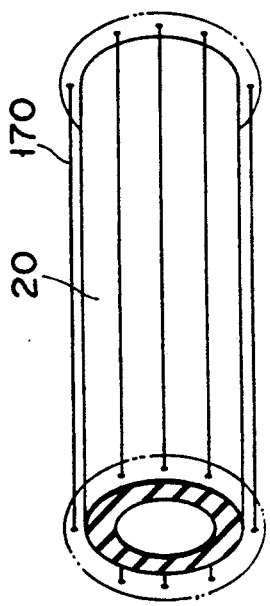
FIG. 19 is a perspective view showing a modification of the elastic tube.

The tenth modification (FIG. 17) is different from the other modifications of the first embodiment in respect of the structure of elastic tube 20. More specifically, as is shown in FIG. 18, several wires 170 are embedded in the wall of elastic tube 20 and extend parallel to one another. These wires 170, like restriction cylinder 40, restrict the axial expansion of tube 20 when tube 20 is inflated, while allowing tube 20 to expand in its radial direction. Wires 170 can be stretched parallel to one another, between the flanges fixed to the ends of tube 20, as is illustrated in FIG. 19. In this case, too, the same advantage is achieved as in the case of the arrangement shown in FIG. 18. Needless to say, wires 170 may be replaced by restriction cylinder 40 as in the other modifications described above.

It will now be explained how the pipe-inspecting apparatus of the tenth modification operates.

As self-propelled section 2 is inserted into a tubular member 101, the distal end of rotary member 171 may contact the inner surface of tubular member 101 or a projection, if any, protruding therefrom. In this case, pressure-sensitive cover 173 has its resistivity changed. The signal representing this change is detected and processed by the signal-processing device incorporated in operation section 3. As a result of this, TV monitor 75 displays the message showing the contact between the rotary member 171 and the inner wall of tubular member 101 or the projection, and also the impact rotary member 171 has received upon contacting the inner surface of member 101 or the projection.

To detect defects, if any, of tubular member 101, such as cracks, ultrasonic-wave motor 168 is driven, thus rotating rotary member 171 and hence rotating eddy current probe 172 through 360 (more around the axis of probe 172. Eddy current probe 172 can therefore scan all over the inner surface of member 101. The signal-processing device processes or analyzes the output signal of probe 172, whereby TV monitor 75 displays whether or not cracks are found in the inner surface of tubular member 101, how many cracks are found, and how large they are.

Owing to the use of eddy current probe 172, the tenth modification of the pipe-inspecting apparatus can detect cracks made in the inner surface of tubular member 101 which are too small for a TV camera to find out. Further, owing to pressure-sensitive cover 173 bonded to the distal end of rotary member 171, self-propelled section 2 can be safely guided deeper into tubular member 101 though the interior of tubular member 101 cannot be seen from outside, and no illumination devices are required to guide safely deep into tubular member 101.

Eddy current probe 172 can be replaced by an ultrasonic transducer for examining the inner surface of tubular member 101. Moreover, pressure-sensitive cover 173 can be replaced by a limit switch or a strain gauge to detect a contact between rotary member 171 and the inner wall of tubular member 101 or the projection protruding therefrom.

Now, the second embodiment of the present invention will be described, with reference to FIGS. 20 to 30. The components of the second embodiment, which are identical or similar to those used in the first embodiment, will be designated by the same numerals in FIGS. 20 to 30, and will now described in detail.

Figure 20:
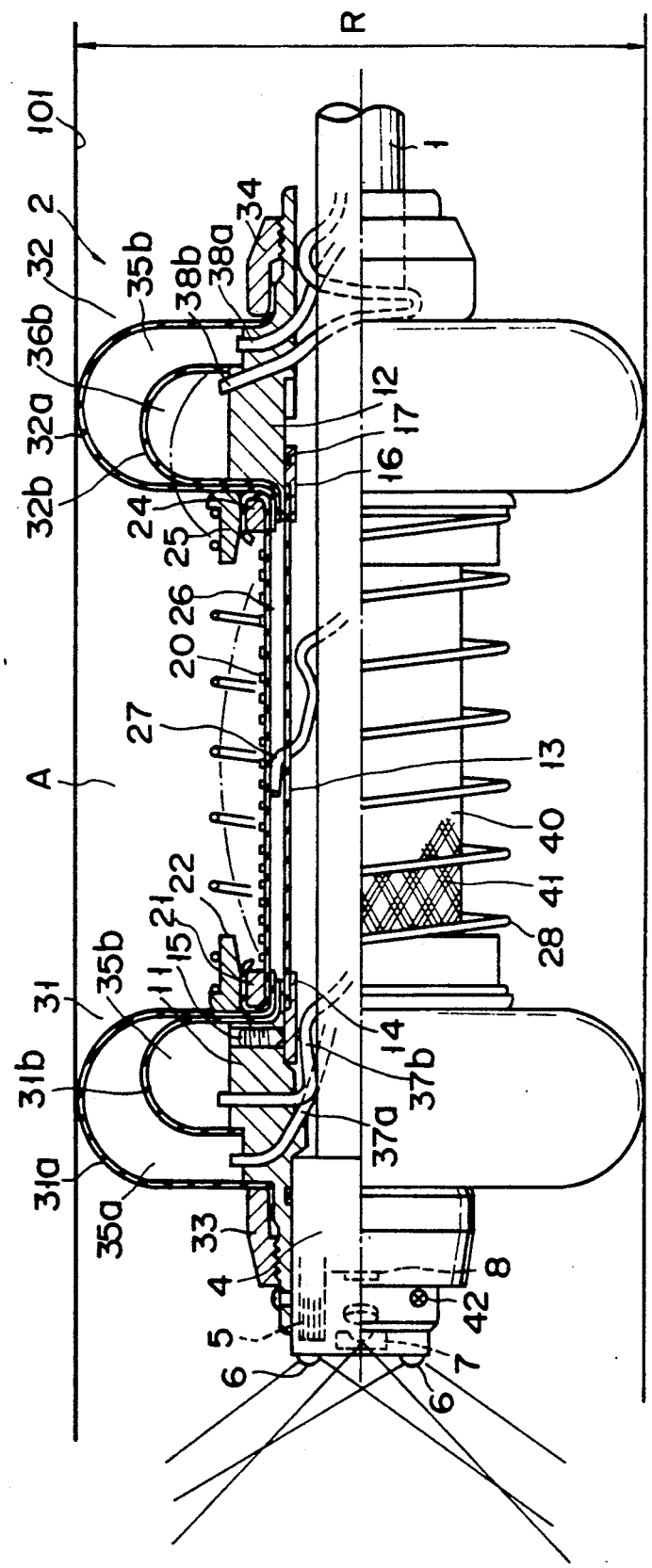
FIGS. 20 and 21 are partially sectional, side views showing the self-propelled unit incorporated in a pipe-inspecting apparatus according to a second embodiment of the invention.

The pipe-inspecting apparatus according to the second embodiment comprises self-propelled section 2 shown in FIG. 20. Front balloon 31 and rear balloon 32 are attached to the peripheries of front body 11 and rear body 12, respectively. Front balloon 31 consists of first balloon element 31a and second balloon element 31b located within first balloon element 31a. Similarly, rear balloon 31 consists of first balloon element 32a and second balloon element 32b located within first balloon element 32a. All balloon elements are made of elastic material such as rubber. Both elements of front balloon 31 are fastened airtightly, at one end, to front body 11 by means of fastening ring 21. Similarly, both elements of rear balloon 32 are fastened airtightly, at one end, to rear body 12 by means of fastening ring 24. First balloon elements 31a and 32b are fastened airtightly, at the other end, to front body 11 and rear body 12 by fastening rings 33 and 34 which are mounted, in screw engagement, on front body 11 and rear body 12, respectively. Second balloon elements 31b and 32b are coupled airtightly, at the other end, to front body 11 and rear body 12, respectively. Hence, two closed spaces 35a and 35b are defined by balloon elements 31a and 31b, that is, space 35a between elements 31a and 31b, and space 35b between element 31b and front body 11; and two closed spaces 36a and 36b are defined by balloon elements 32a and 32b, that is, space 36a between elements 32a and 32b, and space 36b between element 32b and rear body 12.

Air-supplying tubes 37a and 37b are connected to closed spaces 35a and 36b; and air-supplying tubes 38a and 38b are connected to closed spaces 36a and 36b. Therefore, balloon elements 31a, 31b, 32a, and 32b are inflated and deflated, independently of one another, as air is supplying into and discharged from them through these air-supplying tubes 37a, 37b, 38a, and 38b.

To move self-propelled section 2 back and forth in tubular member 101 having a relatively large inside diameter R (FIG. 20), large balloon elements 31a and 32a are used. More precisely, air is supplied into only balloon elements 31a and 32a via air-supplying tubes 37a and 38a, thus inflating balloon elements 31a and 32a so that these elements 31a and 32a contact the inner surface of tubular member 101, thereby holding section 2 in place within member 101. Balloon elements 31b and 32b may be either inflated or not inflated in this condition. They are inflated, as is illustrated in FIG. 20, when air is supplied into these elements 31b and 32b via air-supplying tubes 37b and 38b. They are collapsed when no air is supplied into them.

Figure 21:
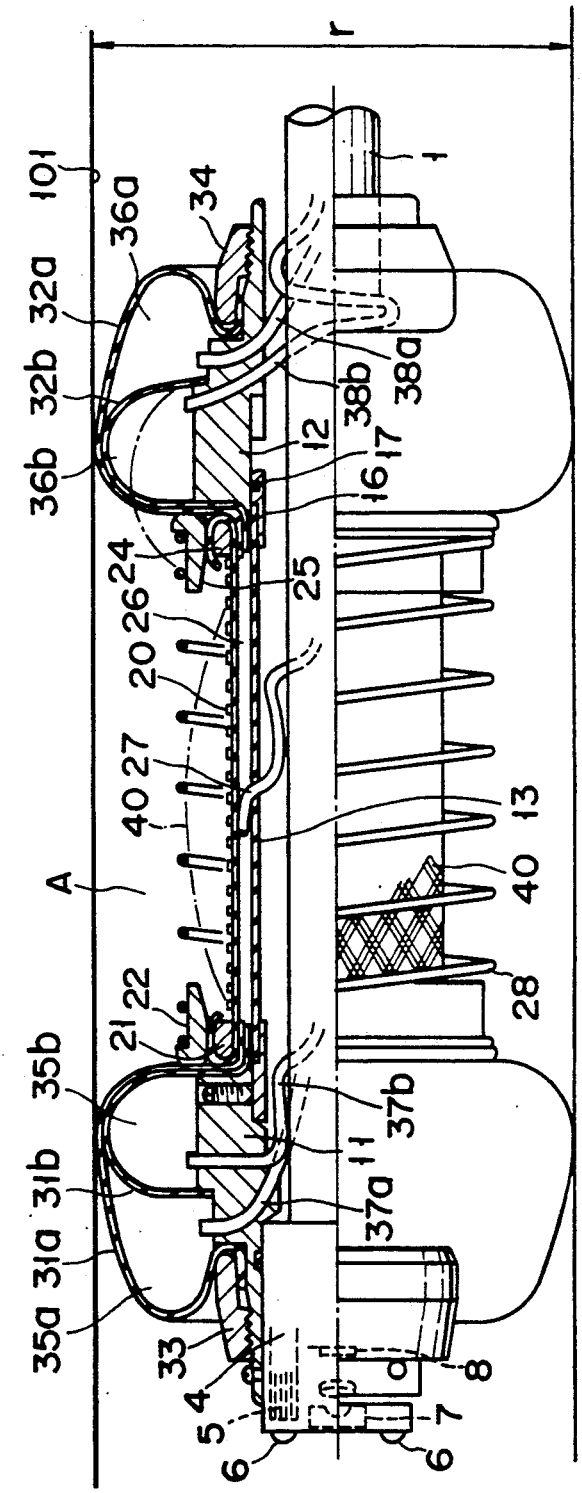
Figure 22A:
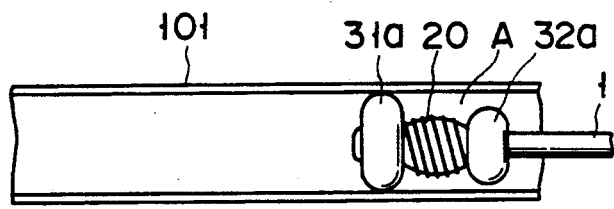
Figure 22B:
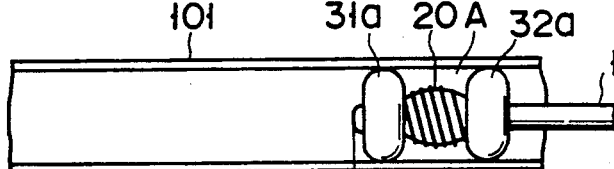
Figure 22C:
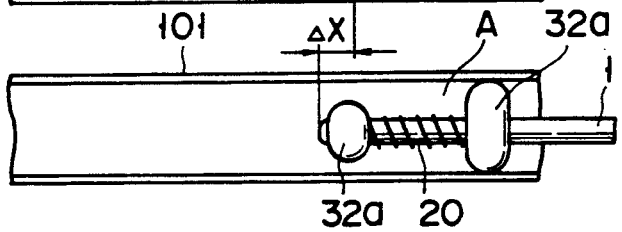

To move self-propelled section 2 back and forth in tubular member 101 having a relatively small inside diameter r (FIG. 21), small balloon elements 31b and 32b are used. More precisely, air is supplied into only balloon elements 31b and 32b via air-supplying tubes 37b and 38b, thus inflating balloon elements 31b and 32b so that these elements 31b and 32b push large balloon elements 31a and 32a onto the inner surface of tubular member 101, thereby holding section 2 in place within member 101. In this case, no air is supplied into balloon element 31a or balloon element 32a, and these elements 31a and 32b are deflated as is shown in FIG. 21.

In the second embodiment, balloons 31a and 32a or balloons 31b and 32b are used in accordance with the inside diameter of tubular member 101, thereby to move self-propelled section 2 forward or backward in tubular member 101 as is illustrated in FIGS. 22A to 22C, and 23.

As is shown in FIG. 20, self-propelled unit A of the second embodiment is slidably mounted on cable 1. The front body 11 of unit A is tightly mounted on the distal end portion 4 of a bore scope and fastened thereto by several screws 42. Alternatively, body 11 can be fixed to distal end portion 4 by means of O-ring 43 wrapped around it, as is illustrated in FIG. 24.

Figure 25:
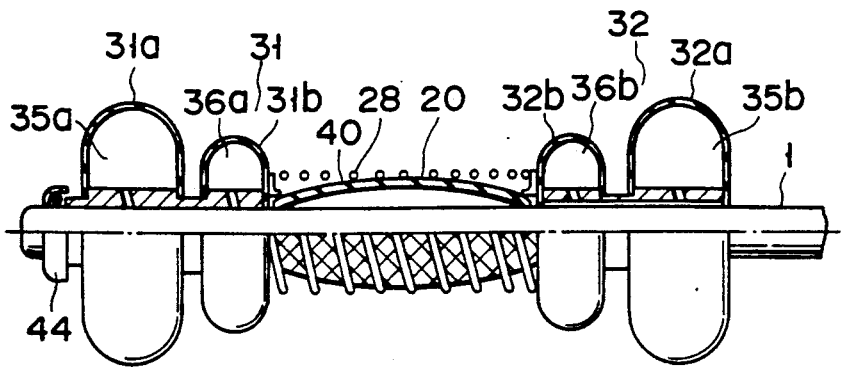
FIG. 25 is a partially sectional view of the self-propelled section incorporated in a first modification of the second embodiment of the invention.

FIG. 25 illustrates a first modification of the second embodiment of the present invention. This modification is characterized by the positions of balloons 31a, 31b, 32a, and 32b of each self-propelled unit. More specifically, balloons 31a and 31b are fastened to front body 11, with balloon 31b located behind balloon 31a; balloons 32a and 32b are fastened to rear body 12, with balloon 32b located in front of balloon 32a. In other words, balloons 31a and 31b, which have different diameters when inflated, are arranged side by side on front body 11, and balloons 32a and 32b, which have different diameters when inflated, are located side by side on rear body 12. Either large balloons 31a and 32b or small balloons 31b and 32b are used in accordance with the inside diameter of a tubular member, thereby to move self-propelled section 2 forward or backward in the tubular member.

Figure 26:
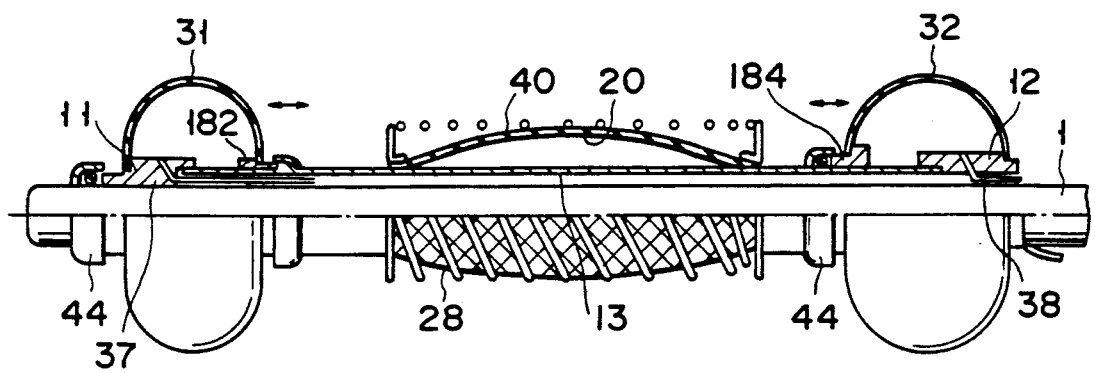
FIG. 26 is a partially sectional view of the self-propelled section incorporated in a second modification of the second embodiment.

FIG. 26 shows a second modification of the second embodiment. Each self-propelled unit of this modification has only two balloons 31 and 32. Balloon 31 is connected, at its front end, to front body 11, and at its rear end, to slider 182 slidably mounted on tube 1. Balloon 32 is connected, at its rear end, to rear body 11, and at its front end, to slider 184 slidably mounted on tube 1. When sliders 182 and 184 are slid on cable 1 toward each other, the diameter decreases which either balloon will have when inflated. Conversely, when sliders 182 and 184 are slid on cable 1 away from each other, the diameter increases which either balloon will have when inflated.

Figure 27:
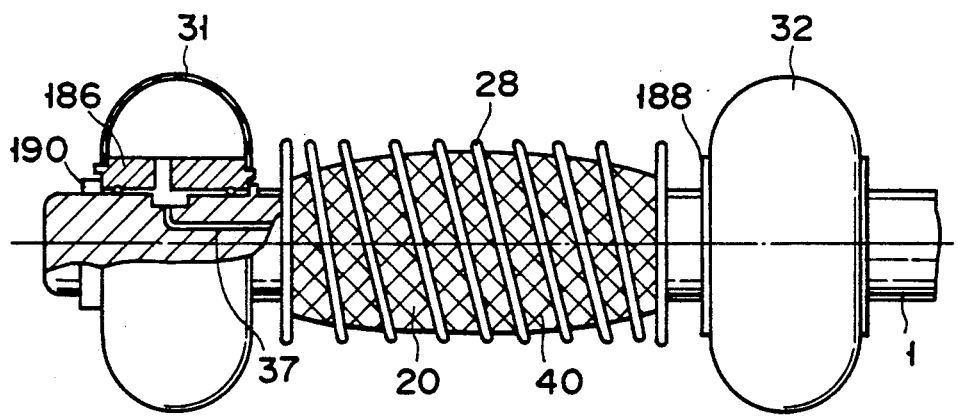
FIG. 27 is a partially sectional view of the self-propelled section incorporated in a third modification of the second embodiment.

FIG. 27 shows a third modification of the second embodiment. Each self-propelled unit of this modification has only two balloons 31 and 32. Balloons 31 and 32 are fastened to ring-shaped supports 186 and 188 which are fixed to front body 11 and rear body 12 by means of fastening rings 190. Supports 168 and 188 can be detached from front body 11 and rear body 12, by removing fastening rings 190 from bodies 11 and 12. Balloon 31 and support 186 form a balloon-support unit, and balloon 52 and support 188 form another balloon-support unit. Either balloon-support unit can be replaced with another unit having a balloon having a different diameter a little greater than the inside diameter of the tubular member in which self-propelled unit is to move forward or backward.

FIGS. 28 and 29 illustrate a fourth modification of the second embodiment of the invention. The fourth modification is characterized by the use of elastic rings 192, each having projections 194 arranged on its outer circumferential surface and spaced apart at regular intervals in the circumferential direction. Rings 194 are detachably mounted on front balloon 31 and rear balloon 32, respectively, so that balloons 31 and 32 can be held in place within a tubular member having a particular inside diameter. They can be replaced by another pair of elastic rings having projections of a different height h, so that balloons 31 and 32 can be held in place in a tubular member having a different inside diameter.

FIG. 30 shows another type of a balloon which can be used in the second embodiment of the invention. This balloon has annular grooves 196 cut in the outer circumferential surface. These grooves 196 provide a sufficient friction between the outer circumferential surface of the balloon and the inner surface of a tubular member when the balloon contacts the inner surface of the tubular member.

FIG. 31 illustrates a third embodiment of the present invention. More specifically, it shows bore scope 10.

Bore scope 10 has flexible cable 1, self-propelled section 2 coupled to the distal end of cable 1, and operation section 3 connected to the proximal end of cable 1.

Connector 198 is coupled to the proximal end of cable 1 and detachably connected to socket 199 of operation section 3. Guide tube 201, which contains the input-end portion of light guide 5, protrudes from socket 199. Lamp 72, which functions as a light source, is incorporated in operation section 3 and opposes the input end of light guide 5. Lens 205, also provided in section 3, collects the light emitted from lamp 72 and applies the light to light guide 5. Socket 199 has a contact (not shown). The signal line extending from solid-state image-pickup element 8 is connected to this contact, and hence to the image-processing section incorporated in operation section 3.

Air-supplying tubes 27, 37a, 37b, 38a, and 38b—connected at one end to self-propelled section 2—extend through cable 1 and are coupled to tube connector 207 detachably connected to the connector 199 of operation section 3. Air-supplying tubes 209, 210, 211, 212, and 213 protrude from connector 207 into operation section 3. These tubes 209, 210, 211, 212, and 213 communicate with air-supplying tubes 27, 37a, 37b, 38a, and 38b, respectively, as long as connector 207 remains attached to operation section 3.

Connectors 198 and 207 are fastened together by coupler 214, thus forming connector unit 216. Hence, both connectors 198 and 207 are simultaneously attached to, or detached from, the socket 199 of operation section 3. Connector unit 218 has detector 218 for detecting whether or not unit 218 has been attached to socket 199. This detector 218 is an optical one, a mechanical one, or of any other type. It generate a signal when unit 218 is attached to socket 199. This signal is supplied to control section 219 incorporated in operation section 3.

Air-supplying tubes 209, 210, 211, 212, and 213 are automatically coupled with air-supplying pumps 220, 221, 222, 223, and 224 which are provided within operation section 3. Pumps 220, 221, 222, 223, and 224 are independently driven by control section 219, to supply air into tubes 209 to 213, discharging air therefrom, and stop supplying or discharging air.

It will now be explained how self-propelled section 2 and bore scope 10 are operated. First, bore scope 10 is coupled to operation section 3. More precisely, connector unit 216 is pushed into socket 199, thereby simultaneously coupling both connectors 198 and 207 with socket 199. As soon as connectors 198 and 207 are connected to socket 199, detector 218 generates a signal. The signal is supplied to control section 219, rendering section 219 operative. Then, control section 219 can drive air-supplying pumps 220, 221, 222, 223, and 224, and self-propelled section 2 can move forward or backward in a tubular member 101.

FIG. 32 shows a first modification of the third embodiment of the invention. More correctly, this figure shows bore scope 10 which can move in a tubular member 101. Bore scope 10 comprises a flexible insertion section 111, operation unit 226, universal cord 228 extending from section 226, and self-propelled section 2 connected to the distal end of insertion section 111. External operation section 3 is connected to operation unit 226 of bore scope 10 by universal cord 228.

Air-supplying tubes 27, 37, and 38, which are connected to elastic tube 20, balloon 31, and balloon 32, respectively, extend through insertion section and also through universal cord 228, and are coupled to connector 230 attached to the proximal end of universal cord 228. More precisely, tubes 27, 37, and 38 are coupled to air-supplying tubes 232, 233, and 234 projecting from connector 230 into operation section 3. Guide tube 236 protrudes from connector 230 into operation section 3. The input end portion of light guide 5 is inserted in guide tube 236. The input end of light guide 5 opposes lamp 72 provided in operation section 3. Lens 205 is interposed between the input end of light guide 5 and lamp 72, for collecting the light emitted from lamp 72 and applying it to light guide 5. Connector 230 has contact 236 which is electrically connected to the contact 238 provided in socket 199 of operation section 3. Operation unit 226 has "forward" switch 240, engage switch 242, release switch 244, and "backward" switch 246. Each of these switches generates a signal whenever it is pushed. The signals generated by operating these switches are supplied from bore scope 10 to control section 219 incorporated in operation section 3 via contacts 238 and 239.

Air-supplying tubes 232, 233, and 234 are connected to air-supplying pumps 220, 221, and 222 which are incorporated in operation section 3. These pumps 220, 221, and 222 are driven independently of one another, by means of control section 219 also provided within operation section 3. They supply air into tubes 220, 221, and 222, discharging air therefrom, and stop supplying or discharging air.

Also in the modification shown in FIG. 32, connector 232 has tubes 232, 233, and 234 connected to air-supplying tubes 27, 37, and 38. Hence, air-supplying tubes 27, 37, and 38 are automatically coupled with air-supplying pumps 220, 221, and 222, respectively, when connector 232 is attached to socket 199 of operation section 3.

Figure 33:
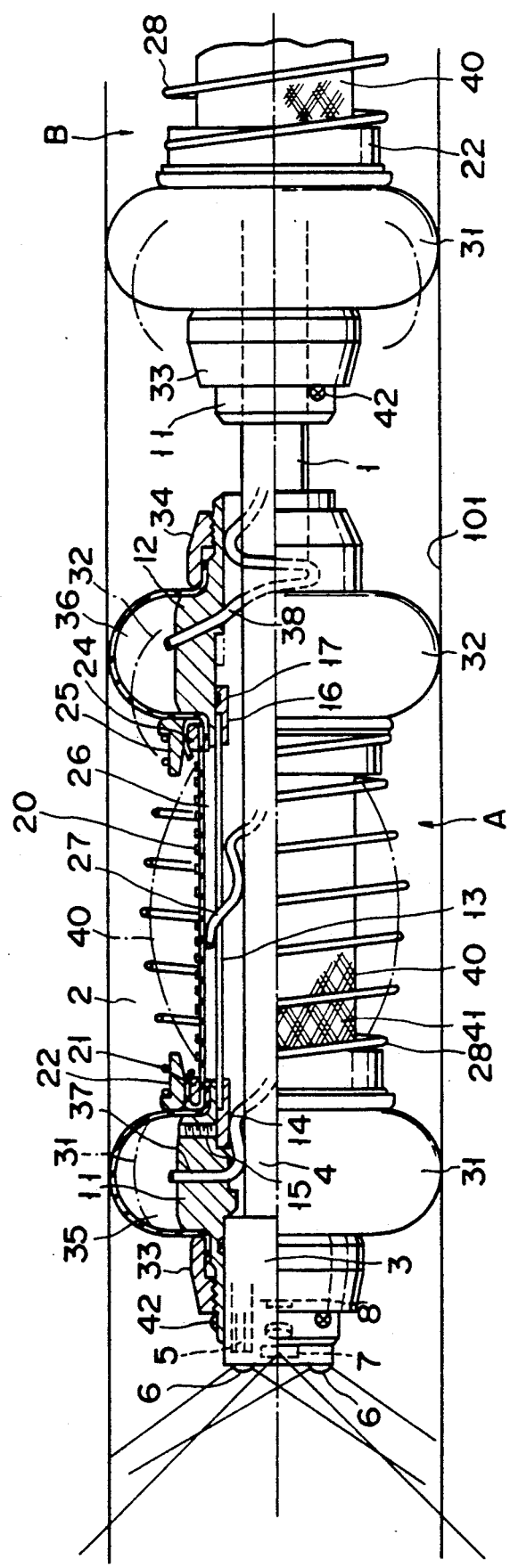
FIG. 33 is a partially sectional side view of the self-propelled unit used in another modification of the third embodiment, said unit having a compression spring.

Now, with reference to FIG. 33, a modification of compression coil spring 28 will be described. As is shown in FIG. 33, spring 28 is shaped like a barrel, having thin end portions and a thick middle portion. The front and rear ends of spring 28 are fitted in spring-seat rings 22 and 25, respectively. Since its middle portion has a large inside diameter, compression coil spring 28 allows elastic tube 20 to inflate in the radial direction and thus contract in the axial direction.

With reference to FIG. 34 and FIGS. 35A and 35B, it will be explained how self-propelled section A shown in FIG. 33 passes through a bent portion of tubular member 101.

When tubular member 101 has a bent portion, such as an elbow, as is shown in FIG. 34, this fact is confirmed by the operator by seeing the interior of member 101 through the bore scope. Then, the operator pushes switch 241 of operation unit 226, thus causing control section 219 to drive air-supplying pumps 220, 221, and 222 such that the tube 20 and balloons 31 and 32 of each self-propelled unit are repeatedly inflated and deflated at the times specified in the following Table 3, thereby to move self-propelled unit forward in tubular member 101:

TABLE 3

|   |           | Action 1 | Action 2 | Action 3 | Action 4 |
|---|-----------|----------|----------|----------|----------|
| A | Balloon 31 | 11100    | 11100    | 00000    | 11100    |
|   | Balloon 32 | 00111    | 00111    | 00000    | 00111    |
|   | Tube 20    | 01110    | 01110    | 00000    | 01110    |
| B | Balloon 31 | 11100    | 11100    | 11100    | 00000    |
|   | Balloon 32 | 00111    | 00111    | 00111    | 00000    |
|   | Tube 20    | 01110    | 01110    | 01110    | 00000    |
| C | Balloon 31 | 11100    | 11100    | 11100    | 11100    |

TABLE 3-continued

|  | Action 1 | Action 2 | Action 3 | Action 4 |
|---|---|---|---|---|
| Balloon 32 | 00111 | 00111 | 00111 | 00111 |
| Tube 20 | 01110 | 01110 | 01110 | 01110 |

When self-propelled unit A reaches the bent portion, pumps 220, 221, and 222 driven to perform action 3. As a result, tube 20, balloon 31, and balloon 32 are all deflated. Therefore, unit A can bend to the same extent as said portion of tubular member 101. When self-propelled unit B reaches the bent portion of member 101, then tube 20, balloon 31, and balloon 32 are all deflated in action 4. Similarly, when self-propelled unit C reaches the bent portion, then tube 20, balloon 31, and balloon 32 are all deflated in action 5 (not specified in Table 3). Hence, units B and C can bend to the same extent as the bent portion of member 101. To move self-propelled units A, B, and C backward in tubular member 101 which is bent, it suffices to supply and discharge air into and from self-propelled units A, B, and C with the timing specified in the following table 2. As can be understood from Table 4, this timing is reversed to that shown in Table 3.

TABLE 4

|  |  | Action 1 | Action 2 | Action 3 | Action 4 |
|---|---|---|---|---|---|
| A | Balloon 31 | 00111 | 00111 | 00000 | 00111 |
|   | Balloon 32 | 11100 | 11100 | 00000 | 11100 |
|   | Tube 20 | 01110 | 01110 | 00000 | 01110 |
| B | Balloon 31 | 00111 | 00111 | 00111 | 00000 |
|   | Balloon 32 | 11100 | 11100 | 11100 | 00000 |
|   | Tube 20 | 01110 | 01110 | 01110 | 00000 |
| C | Balloon 31 | 00111 | 00111 | 00111 | 00111 |
|   | Balloon 32 | 11100 | 11100 | 11100 | 11100 |
|   | Tube 20 | 01110 | 01110 | 01110 | 01110 |

FIG. 36 through FIG. 40 show a modification of the cable-guiding device incorporated in a pipe-inspecting apparatus according to the present invention.

Figure 36:
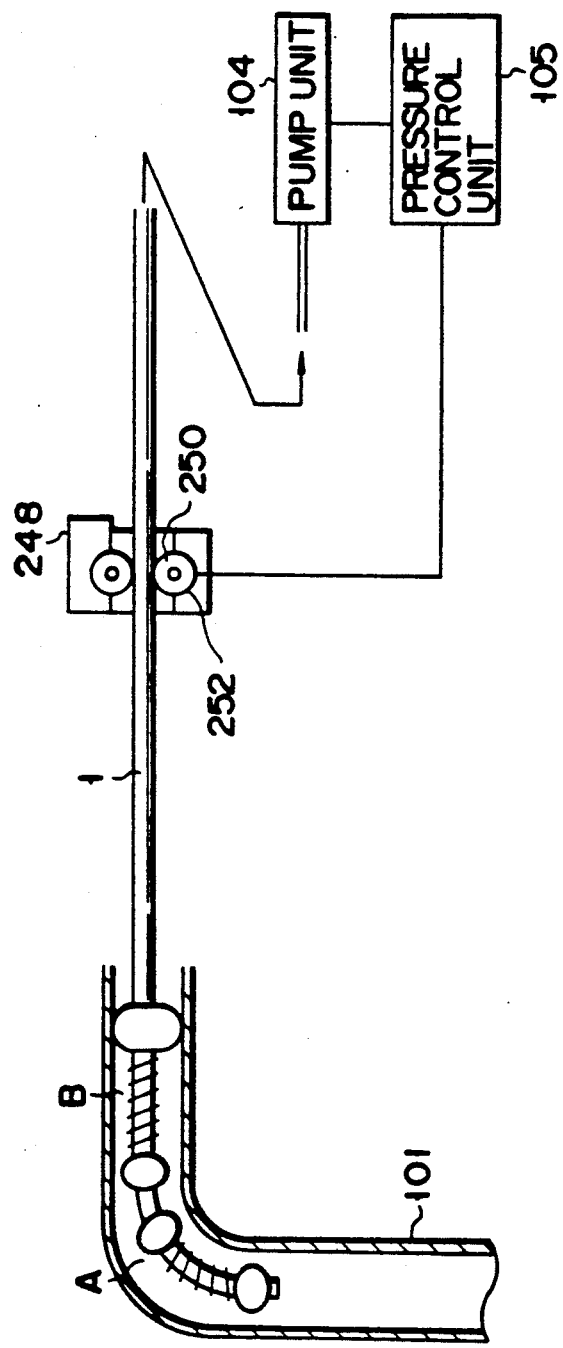
FIG. 36 schematically shows a modification of the cable-guiding device incorporated in a pipe-inspecting apparatus according to this invention.
Figures 37, 38, 39:
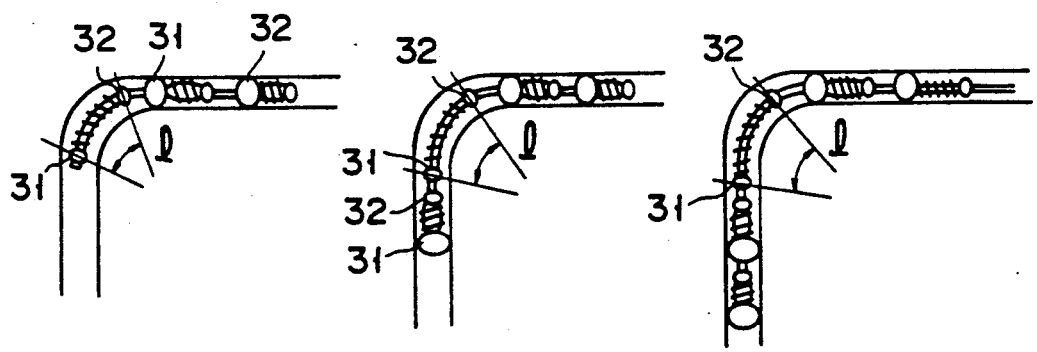
FIGS. 37 to 39 are side views of the cable-guiding device, explaining how the self-propelled unit of the cable-guiding device moves in a bent portion of a pipe.

As is illustrated in FIG. 36, the cable-guiding device has detector 248 for detecting the distance cable 1 has been pushed forward in a tubular member 101 or the distance cable 1 has been pulled back in member 101. When it is determined, from the distance detected by this detector 248, that any of self-propelled units A, B, and C has reached the bent portion of tubular member 101, the balloons of this unit are deflated. As a result of this, the unit can smoothly pass through the bent portion. Detector 248 comprises a pair of rollers 250 and potentiometer 252. Rollers 250 clamp cable 1, and therefore rotate as cable 1 passes through the gap between them. Potentiometer 252 detects the rotation of one of rollers 250, thereby measuring the distance cable 1 has moved forward or backward. FIGS. 37, 38, and 39 illustrate how self-propelled units A, B, and C pass through the bent portion of tubular member 101. As is evident from these figures, in the bent portion of member 101, elastic tube 20 is bent and elongated, and balloons 31 and 32 are deflated.

Figure 40:
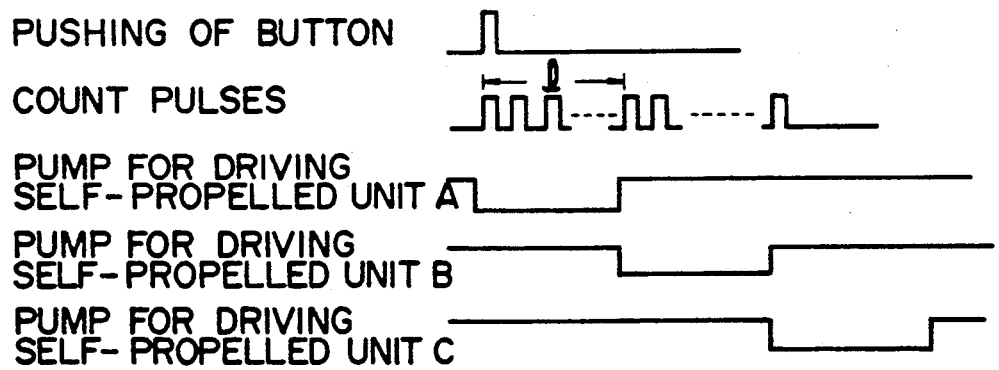
FIG. 40 is a timing chart showing the signals for driving the cable-guiding device shown in FIG. 36.

FIG. 40 is a timing chart showing the signals for driving the cable-guiding device. When it is determined that self-propelled unit A has reached the bent portion of member 101, the operator pushes a button provided on operation section 3 (not shown). Then, the pumps (not shown) connected to balloons 31 and 32 of unit A by air-supplying tubes (not shown, either) are driven, thus discharging air from balloons 31 and 32 of unit A, whereby these balloons are deflated. When self-propelled units B and C sequentially reach the bent portion of tubular member 101, the operator pushes the button, whereby the balloons of units B and C are deflated in the same way as balloons 31 and 32 of self-propelled unit A.

Figure 41:
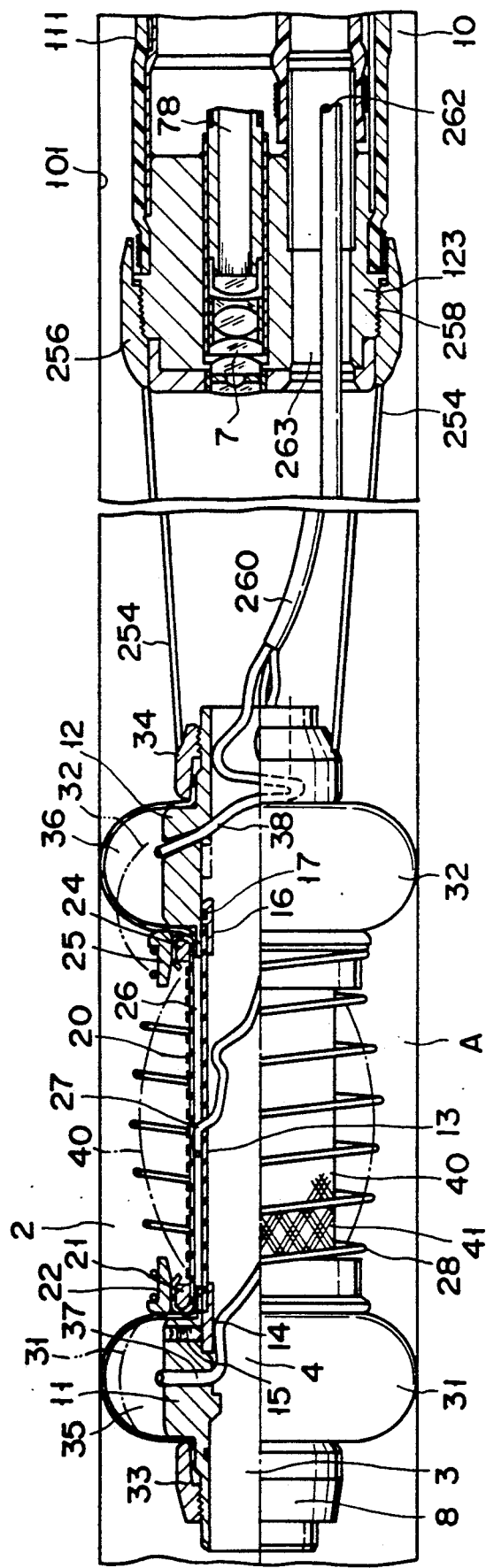
FIG. 41 is a partially sectional, side view showing the self-propelled unit incorporated in a pipe-inspecting apparatus according to a fourth embodiment of the present invention.

A fourth embodiment of the present invention will now be described with reference to FIG. 41. The self-propelled section 2 of this embodiment has ring 34 mounted on its rear end. Two wires 254 are connected to ring 34 at the forward end. The rear end of either wire is connected to hood 256 mounted on the distal end either portion 4 of bore scope 10. Thus, wires 254 couple self-propelled section 2 and bore scope 10. The wires are long enough to provide bore scope 10 with a sufficiently large view field. The threaded portion 258 of bore scope 10, on which hood 256 is mounted, can be used to hold an optical adapter such as a prism.

Air-supplying tubes 27, 37, and 38 are connected to self-propelled section 2 at the forward end. Their rear end portions are bundled together and inserted in one sheath tube 260 which extends through the channel 262 of bore scope 10 and is coupled to an air-supplying device (not shown) at the proximal end of bore scope 10.

To insert bore scope 10 into a tubular member 101, self-propelled section 2 is operated in the same way as in the first to third embodiments. To move bore scope 10 backward in tubular member 101, it suffices to pull bore scope 10 backward. In this case, self-propelled section 2 can move backward if operated with the timing specified in Table 2. Wires 254 can be thick and rigid, so that bore scope 10 is pushed backward as self-propelled section 2 moves backward.

Instead of two wired 254, three or more wires can be used to connect self-propelled section 2 and bore scope 10. The more wires, the more stably bore scope 10 can be moved forward and backward as self-propelled section 2 moves back and forth in tubular member 101. Further, the rear end portion of section 2 can be coated with substance having a high reflectivity. If coated with such substance, the rear end portion of section 2 reflects the illumination light applied from the distal end of bore scope 10, thereby illuminating anything in the view field of bore scope 10, particularly the inner surface of the tubular member 101.

Figure 42:
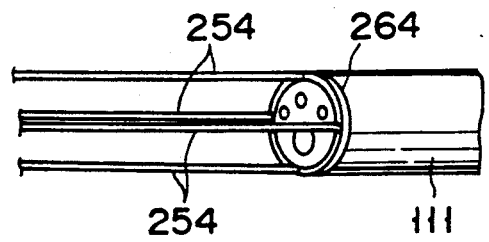
FIGS. 42 and 43 are a perspective view and a front view, respectively, of a wire-holder used in a first modification of the fourth embodiment.
Figure 43:
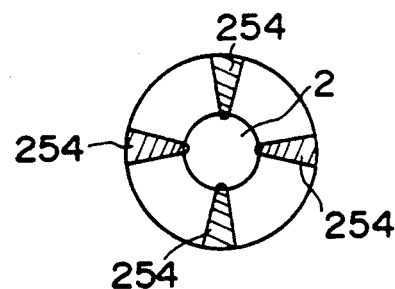

FIGS. 42 and 43 show a first modification of the fourth embodiment of this invention. This modification has no hoods on the distal end of the insertion section 111 of bore scope 10. Ring 264 is directly mounted on the distal end of insertion section 111, and wires 254 are coupled to this ring 264. Wires 254 extend parallel to one another, in the axial direction of bore scope 10. Therefore, wires 254 appear in the view field of bore scope 10 in such a manner as is illustrated in FIG. 43. They inevitably hide portions of an object in the view field, though these portions are small.

Figure 44:
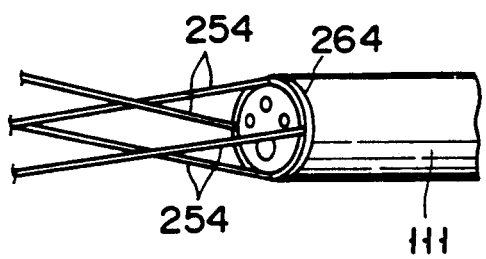
FIGS. 44 and 45 are a perspective view and a front view, respectively, of a wire-holder used in a second modification of the fourth embodiment.
Figure 45:
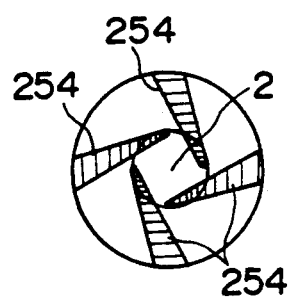

FIGS. 44 and 45 illustrates a second modification of the fourth embodiment. The second modification is identical to the first, except that wires 254 are inclined to the axis of bore scope 10, and appear in the view field of bore scope 10 as is illustrated in FIG. 45. Although some portions of an object in the view field cannot be seen, they can be seen as self-propelled section 2 pulls forward of pushes back bore scope 10 in tubular member 101. After all, the object can be seen in its entirety.

Figure 46:
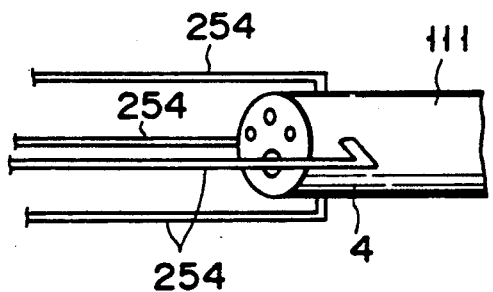
FIGS. 46 and 47 are a perspective view and a front view, respectively, of a wire-holder used in a third modification of the fourth embodiment.
Figure 47:
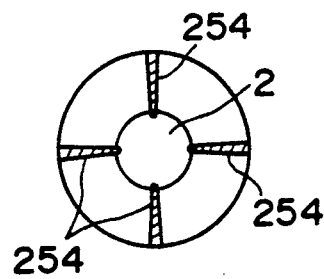

FIGS. 46 and 47 show a third modification of the fourth embodiment of the invention. In this modification, wires 254 extend first radially from the circumferential surface of bore scope 10, then are bent by 90°, and finally extend parallel to the axis of the bore scope 10. Hence, wires 254 look in the view field of bore scope 10, such way as is illustrated in FIG. 47. Wires 254 do not hide any portions of an object in the view field.

The rear end portion of sheath tube 260 can be fitted in inlet port 263 of channel 262 of bore scope 10, tube 260 can be used as means for connecting self-propelled section 2 and bore scope 10. In this case, wires 254 can be dispensed with, or less wires are sufficient.

Air-supplying pumps, which are driven by electrical signals, can be incorporated in self-propelled section 2. When such pumps are provided within section 2, it suffices to connect the pumps to operation section 3; air-supplying tubes 27, 37, 38 need not extend between self-propelled section 2 and bore scope 10, and does not hide an object from bore scope 10.

When bore scope 10 is one having no channels 262, air-supplying tubes 27, 37, and 38 can be fastened to wires 254 and guided along the circumferential surface of insertion section 111 of bore scope 10.

The self-propelled section 2 of the fourth embodiment has only one self-propelled unit. Nonetheless, section 2 can have two ore more self-propelled units which are coaxially connected to each other.

A fifth embodiment of the invention will be described with reference to FIGS. 48 to 51C. As is shown in FIGS. 49 and 50, support wires 266, which are bent in the form of letter U, are provided within each of balloons 31 and 32. The support wires 266 in front balloon 31 are spaced apart from each other, around front body 11, each with its both ends fitted in groove 11a cut in front body 11. Similarly, the support wires 266 in front balloon 32 are spaced apart from each other, around rear body 12, each with its both ends fitted in groove 12a cut in front body 12. The circle defined by the tops of U-shaped wires 266 has diameter D which is smaller than the inside diameter R of tubular member 101.

As front balloon 31 is deflated as is shown in FIG. 51C, the distal end portion 4 of cable 1, which is located in front of rear balloon 32, bends downward due to its own weight. However, support wires 266 function as stoppers, preventing portion 4 from bending down further. Since distal end portion 4 does not bend down in excess, the view field of the observation means provided in portion 3 does not move downward too much. For the same reason, the distal end portion 4 of cable 1 does not bend upward in excess as front balloon 31 is inflated. Therefore, the distal end portion of the bore scope is prevented from moving up and down in excess while the self-propelled section is moving forward or backward in tubular member 101. Hence, the view field of the bore scope does not move too much.

In addition, since support wires 266 are also provided in rear balloon 32, balloon 32 does not bend down too much by its own weight when it is deflated. Hence, the view field of the bore scope does not move upward when balloon 32 is deflated as is shown in FIG. 51A.

Figure 48:
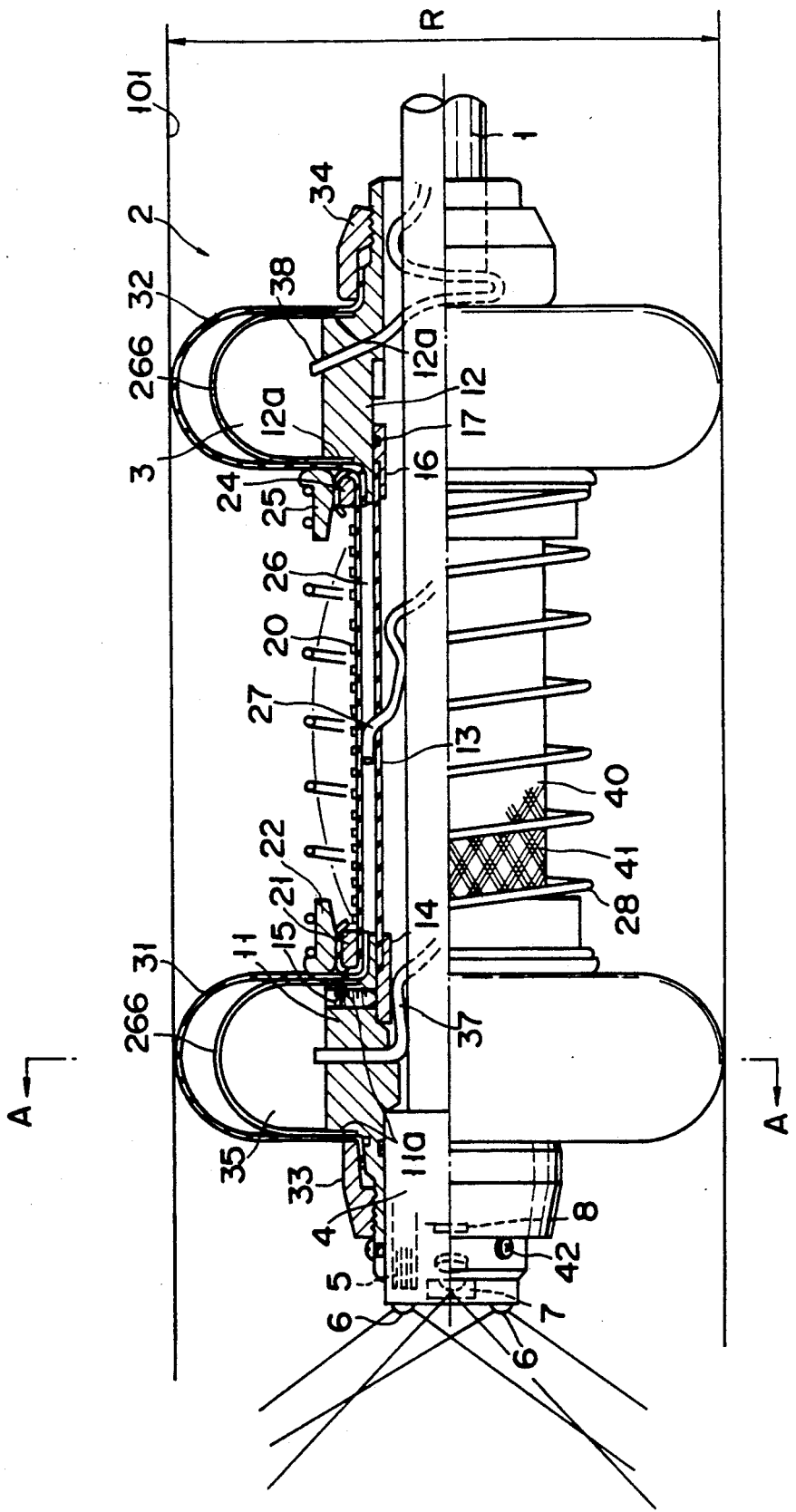
FIG. 48 is a partially sectional side view showing the self-propelled unit incorporated in a pipe-inspecting apparatus according to a fifth embodiment of the invention.
Figure 52:
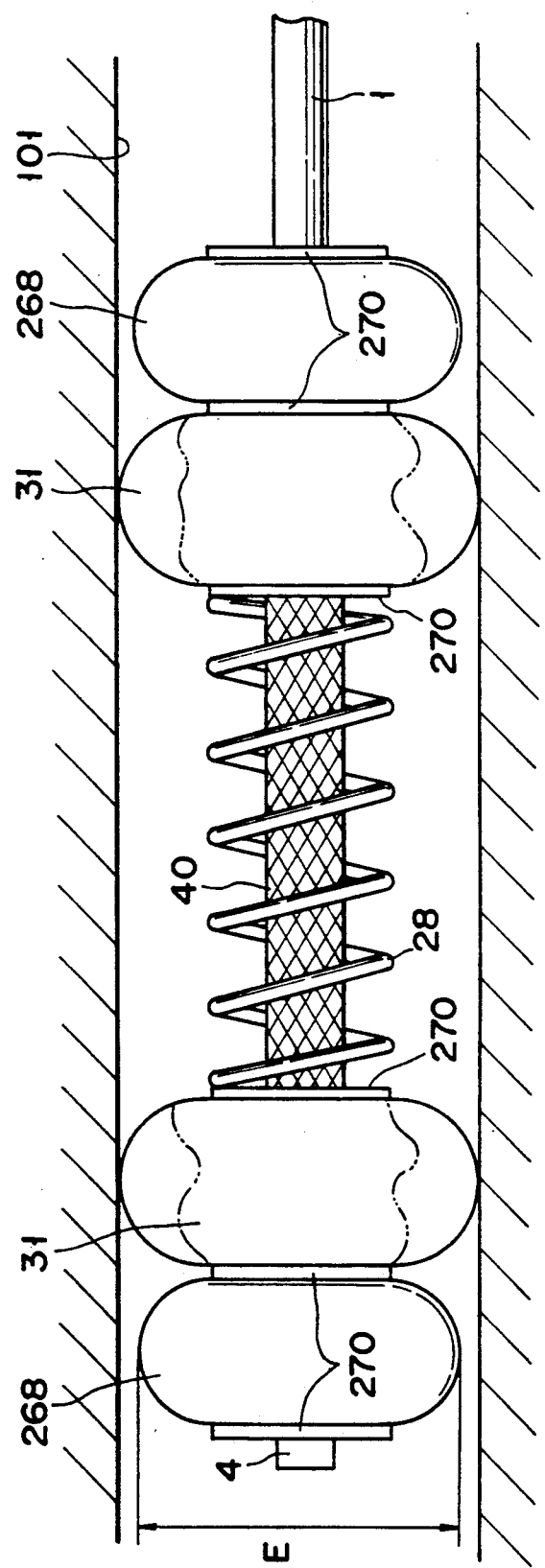
FIG. 52 is a side view showing the self-propelled unit incorporated in a first modification of the fifth embodiment of the invention.

FIG. 52 illustrates a first modification of the fifth embodiment of the present invention. This modification has support balloons 268 which perform the same function as support wires 266 used in the fifth embodiment (FIGS. 48 to 50). The first support balloon is mounted on distal end portion 4, held by washers 270, and located in front of balloon 31. The second support balloon is mounted on cable 1, held by washers 270, and located behind rear balloon 32. As long as the self-propelled section remains in tubular member 101, both support balloons 268 are inflated and have a diameter E. Front balloon 31 and rear balloon 32 are repeatedly inflated to have a diameter larger than the diameter E and deflated to have a diameter smaller than the diameter E. Therefore, support balloons 268 achieve the same advantage as support wires 266 do in the pipe-inspecting apparatus shown in FIG. 48.

Figure 53:
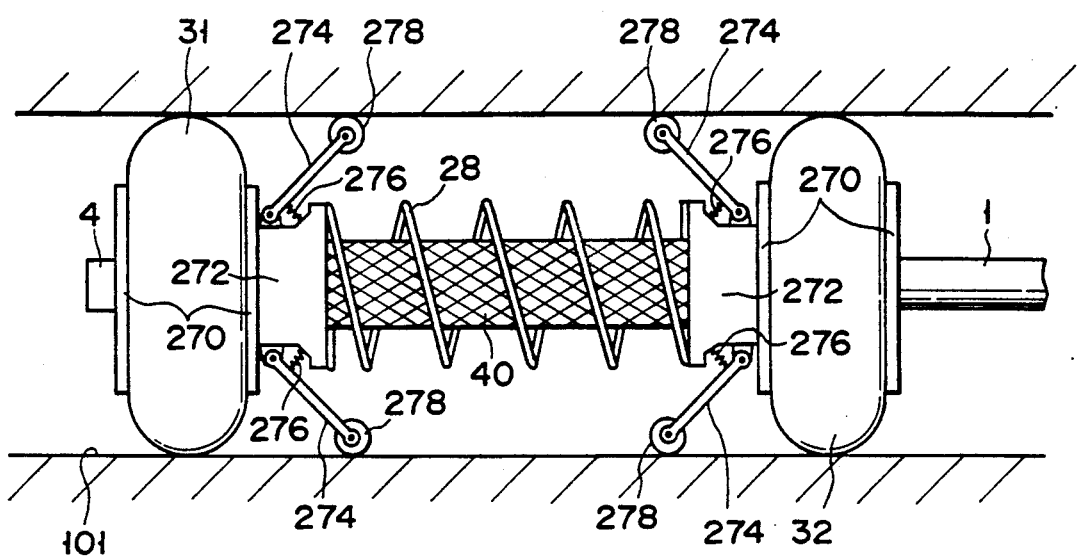
FIG. 53 is a side view showing the self-propelled unit incorporated in a second modification of the fifth embodiment of the invention.

FIG. 53 shows a second modification of the fifth embodiment of the invention. This modification has two supports which perform the same function as support wires 266 do in the apparatus shown in FIG. 48. These supports are connected to the rear of front balloon 31 and the front of rear balloon 32, respectively. Either support comprises hollow cylinder 272 mounted on cylinder 40, at least three levers 274 rotatably connected at one end to cylinder 272, compression coil springs 276 biasing levers 274 toward the inner surface of tubular member 101, and rollers 278 attached to the distal ends of levers 274. Cylinders 272 oppose each other and hold compression coil spring 28 between them. The two supports, which are connected to balloons 31 and 32, respectively, achieve the same advantage support wires 266 do in the apparatus shown in FIG. 48.

Figure 54:
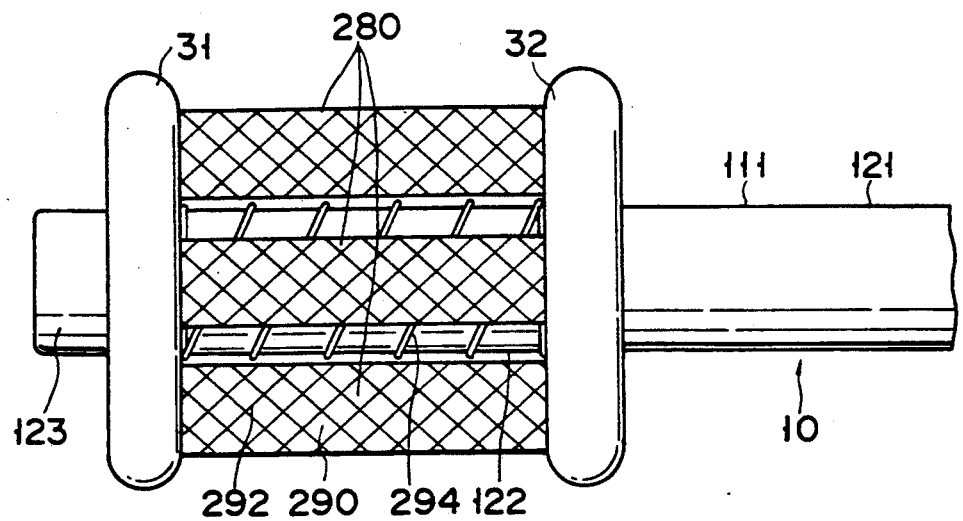
FIGS. 54 and 55 are a side view and a partially sectional side view, respectively, of the self-propelled unit used in a pipe-inspecting apparatus according to a sixth embodiment of the present invention.

Now, a sixth embodiment of the present invention will be described. As is shown in FIG. 54, the insertion section 111 of bore scope 10 comprises flexible section 121, bending section 122 coupled to the distal end of flexible section 121, and distal end section 123 connected to the distal end of bending section 122. Insertion section 111 contains an image guide, a light guide, a channel, and the like. Front balloon 31, rear balloon 32, and four actuators 280 are attached to the circumferential surface of bending section 122. Bore scope 10 is designed to move by itself in tubular member 101. Bending section 122 can be bent such that distal end section 123 is turned upward, downward, leftward, and rightward.

Figure 55:
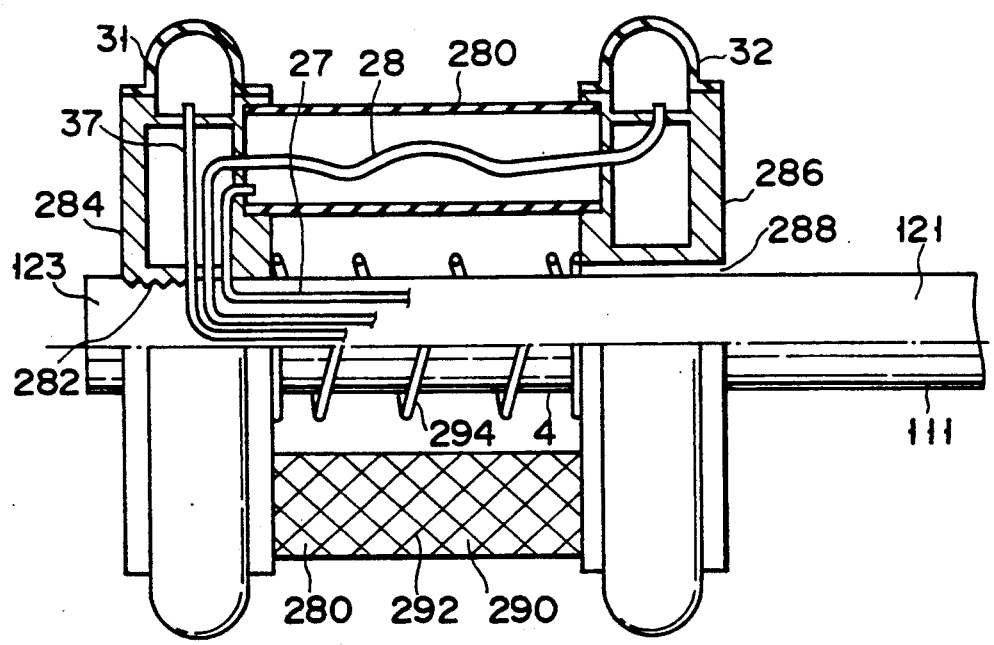

With reference to FIG. 55, balloons 31 and 32 and actuators 280 will be described, and also their positional relationship will be explained. Distal end section 123 has threaded portion 283. Hollow annular body 284 is fixed in screw engagement with threaded portion 283. Front balloon 31, which is made of elastic material such as rubber, is attached to the outer circumferential surface of fastening ring 284. Hollow annular body 286 is mounted on flexible section 121 of insertion section 111. It is located behind and spaced apart from annular body 284. This annular body 286 has hole 288 having a diameter slightly larger than that of flexible section 121, and can therefore slide in the axial direction of flexible section 121. Rear balloon 31, which is made of elastic material such as rubber, is attached to the outer circumferential surface of fastening ring 286. Both balloons 31 and 32 can be inflated and deflated, as a fluid is supplied into them and discharged from them.

Actuators 280 have the same structure. Each actuator 280 comprises tube 290 made of synthetic rubber and mesh tube 292 covering tube 290. Each actuator 280 is fastened to annular body 284 at one end, and to annular body 286 at the other end. Four actuators 280 therefore extend between balloons 31 and 32. They are spaced apart from one another in the circumferential direction of bending section 122. Coil spring 294 is wound about bending section 122, and interposed between annular bodies 284 and 286.

Air supply/discharge tubes 37 and 38 are connected, at one end, to balloons 31 and 32, respectively. Further, four air supply/discharge tubes 27 are connected, at one end, to four actuators 280, respectively. These tubes 27, 37, and 38 extend from balloons 31 and 32 and actuators 280 through the interior of annular body 284, distal end section 123, and insertion section 111, and extend from the proximal end of bore scope 10. Tubes 27, 37, and 38 are connected to air supply/discharge controller 85, which will be later described in detail.

Figure 56:
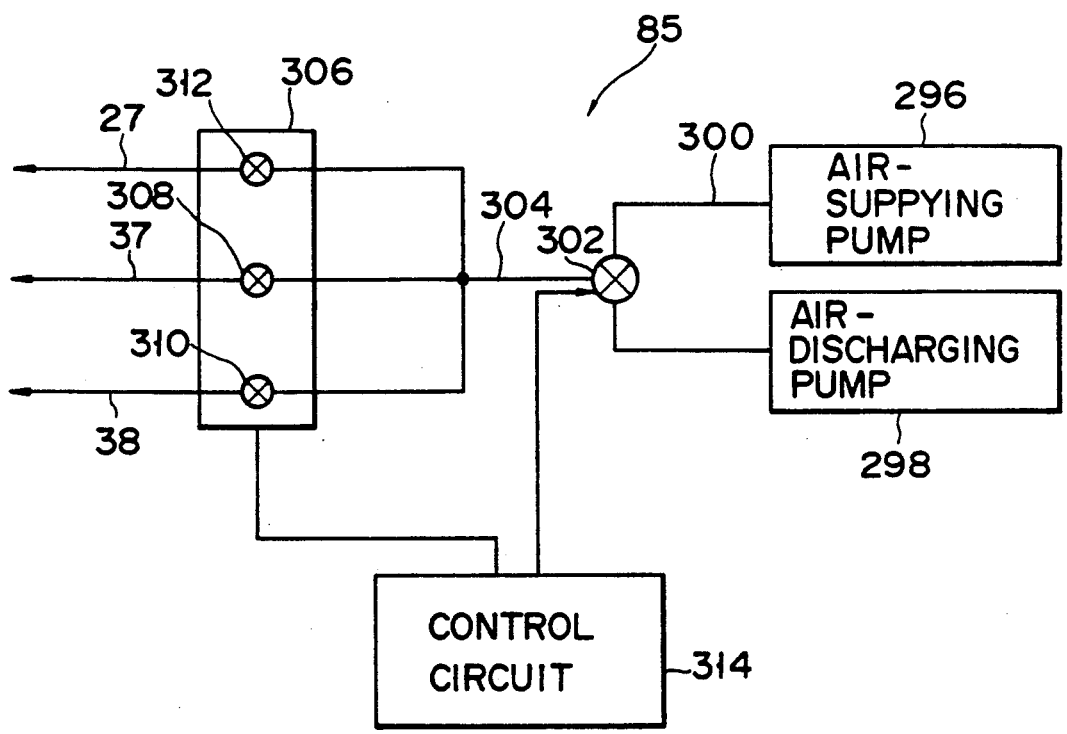
FIG. 56 is a block diagram showing the fluid-pressurizing device incorporated in the sixth embodiment.

As is shown in FIG. 56, air supply/discharge controller 85 comprises air-supplying pump 296 and air-discharging pump 298. Both pumps 296 and 298 are connected by pipes 300 to switching valve 302. Switching valve 302 is connected by pipe 304 to valve device 306. Device 306 has three valves 308, 310, and 312. First valve 308 is connected to air supply/discharge tube 37 which is coupled to front balloon 31. Second valve 310 is connected to air supply/discharge tube 38 which is coupled to rear balloon 32. Third valve 312 is connected to air supply/discharge tubes 27 which are coupled to actuators 280. Control circuit 313 is connected to switching valve 302 and also to valve device 306, for controlling valves 302, 308, 310, and 312 in the following way.

Switching valve 302 connects pipe 304 to air-supplying pump 296 or air-discharging pump 298 in accordance with the control signal supplied from control circuit 314. When valve 302 connects pipe 304 to air-supplying pump 296, pump 296 is connected to valve device 306 by pipes 300 and 304. When valve 302 connected pipe 304 to air-discharging pump 298, pump 298 is coupled to valve device 306 by pins 300 and 304. Valves 308, 310, and 312 connect pipe 304 to air-discharge tubes 37, 38, and 27, respectively, when they open in response to the control signals supplied from control circuit 314. Hence, valves 308, 310, and 312 can connect balloon 31, balloon 32, and actuators 280 to either air-supplying pump 296 or air-discharging pump 298.

The operation of the pipe-inspecting apparatus shown in FIGS. 54 to 56, i.e., the sixth embodiment of the invention, will now be explained, with reference to FIGS. 57A to 57D.

Figure 57A:
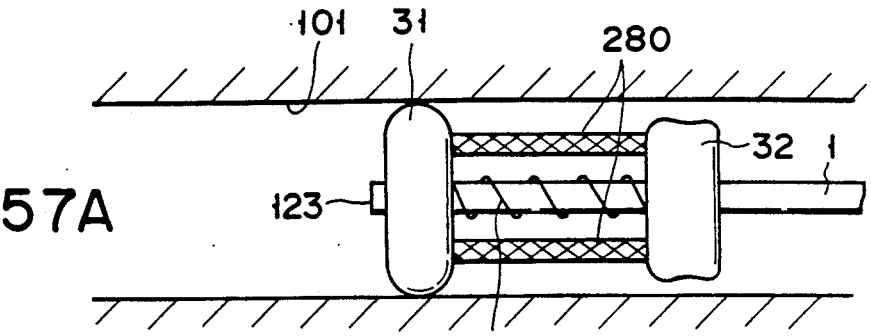
FIGS. 57A to 57D are side views of the self-propelled unit, showing the sequence of movement of the unit in the pipe under inspection.
Figure 57B:
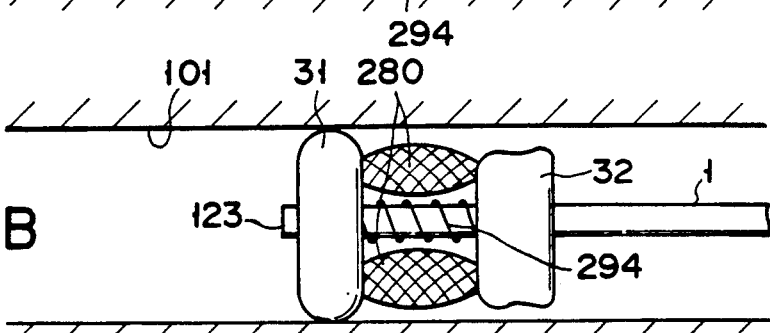
Figure 57C:
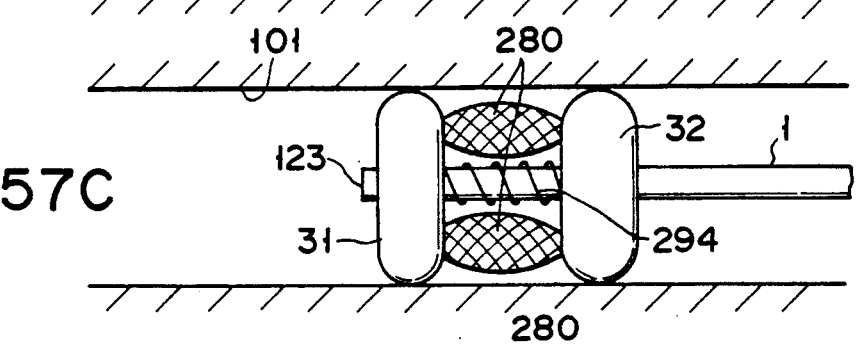

After bore scope 10 has been inserted into tubular member 101, switching valve 302 is operated such that valve device 306 is connected to air-supplying pump 296. Then, first valve 308 of device 306 is opened, whereby pump 296 supplies air into front balloon 31. As a result, balloon 31 is inflated until it contacts the inner surface of tubular member 101 as is shown in FIG. 57A. Bore scope 10 is thereby held in tubular member 101. First valve 308 is closed, and third valve 312 of device 306 is opened. Air-supplying pump 296 therefore supplies air into actuators 280. All actuators 280 simultaneously expand in their radial direction and contract in their axial direction, as is illustrated in FIG. 57B. Annular body 286 therefore moves toward distal end section 123. In other words, annular body 286, to which rear balloon 32 is attached, slides on insertion section 111 forward against the force of coil spring 294. In this condition, third valve 312 is closed, and second valve 310 is opened. Now connected to rear balloon 32 by valve 312 and air supply/discharge tube 38, pump 296 supplies air into rear balloon 32. Rear balloon 32 is inflated until it contacts the inner surface of tubular member 101, as is illustrated in FIG. 57C. Balloons 31 and 32, both contacting the inner surface of tubular member 101 hold bore scope 10 firmly in member 101. Then, second valve 310 of valve device 306 is closed.

Figure 57D:
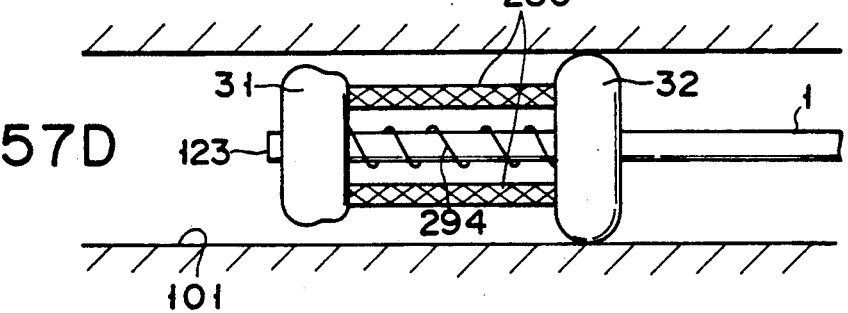

Thereafter, switching valve 302 is operated such that device 306 is disconnected from air-discharging pump 296 and connected to air-discharging pump 298. Further, first valve 308 and third valve 312 are opened, whereby pump 298 discharges air from front balloon 31 and all actuators 280. As a result of this, front balloon 31 is deflated, leaving the inner surface of tubular member 101, and actuators 280 contract in their radial direction and extend in their axial direction, allowing coil spring 294 expands to its original length, as is illustrated in FIG. 57D. Hence, annular body 284, which is fixed to distal end section 123 and to which front balloon 31 is attached, moves away from slidable annular body 286, that is, deeper into tubular member 101. Bore scope 10, which is fastened to annular body 284 is moved forward in tubular member 101. When bore scope 10 has been moved forward a predetermined distance, control circuit 314 controls switching valve 302 and valve device 306 such that air is supplied into front balloon 31, thus inflating balloon 31 again, as is shown in FIG. 57A. Then, air is discharged from rear balloon 32, and is supplied into actuators 280.

Switching valve 302 and valve device 306 are operated repeatedly by control circuit 314 is the way described above, whereby bore scope 10 moves in tubular member 101.

Figure 58:
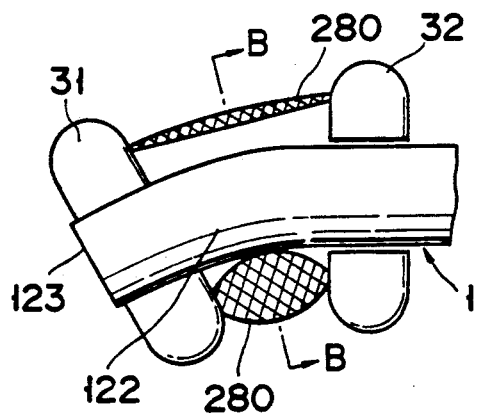
FIG. 58 is a side view showing a modification of the self-propelled unit used in the sixth embodiment.
Figure 59:
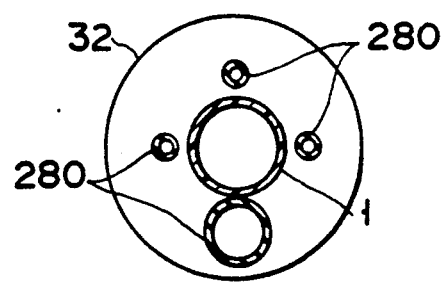
FIGS. 59 is a cross-sectional view of the self-propelled unit, taken along line B—B in FIG. 58.

In the sixth embodiment, four actuators 280 mounted on the circumferential surface of bore scope 10 are simultaneously inflated and deflated. Instead, they can be inflated and deflated independently of one another, by providing four valves in valve device 306, connecting these valves to actuators 280, and selectively opening these valves. In this case, bending section 122 can be bent upward, downward, leftward or rightward. More specifically, when air-supplying pump 296 supplies air into only actuator, this actuator expands in its radial direction and contracts in its axial direction as is illustrated in FIGS. 58 and 59. Those portions of annular bodies 284 and 286 which are connected this actuator are, therefore, pulled toward each other, whereas those portions of annular bodies 284 and 286 are pulled away from each other. As a result, bending section 122 is bent in the direction shown in FIG. 58. When air is supplied into any other actuator, bending section 122 is bent in another direction.

Figure 60:
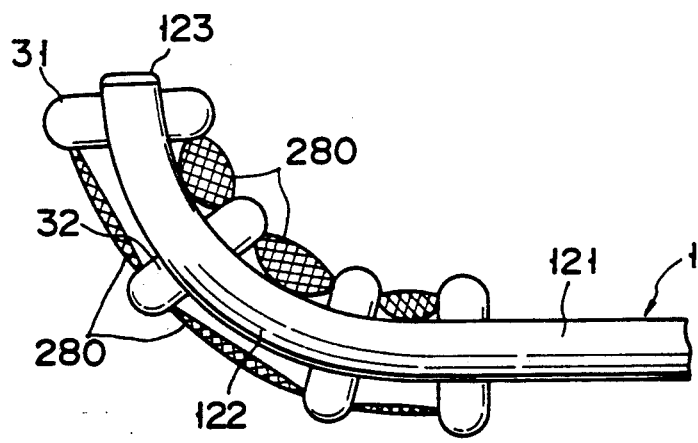
FIG. 60 is a side view of another modification of the self-expelled unit incorporated in the sixth, embodiment.

Moreover, as is illustrated in FIG. 60, two or more groups of actuators 280 can be mounted on bending section 122, arranged in the axial direction thereof. In this case, section 122 can be bent at an angle greater than in the case where only one group of actuator 280 is mounted on bending section 122, allowing bore scope 10 to move smoothly through a greatly bent portion of tubular member 101.

Now, a seventh embodiment of the present invention will be described, with reference to FIG. 61 through FIG. 66.

Figure 62:
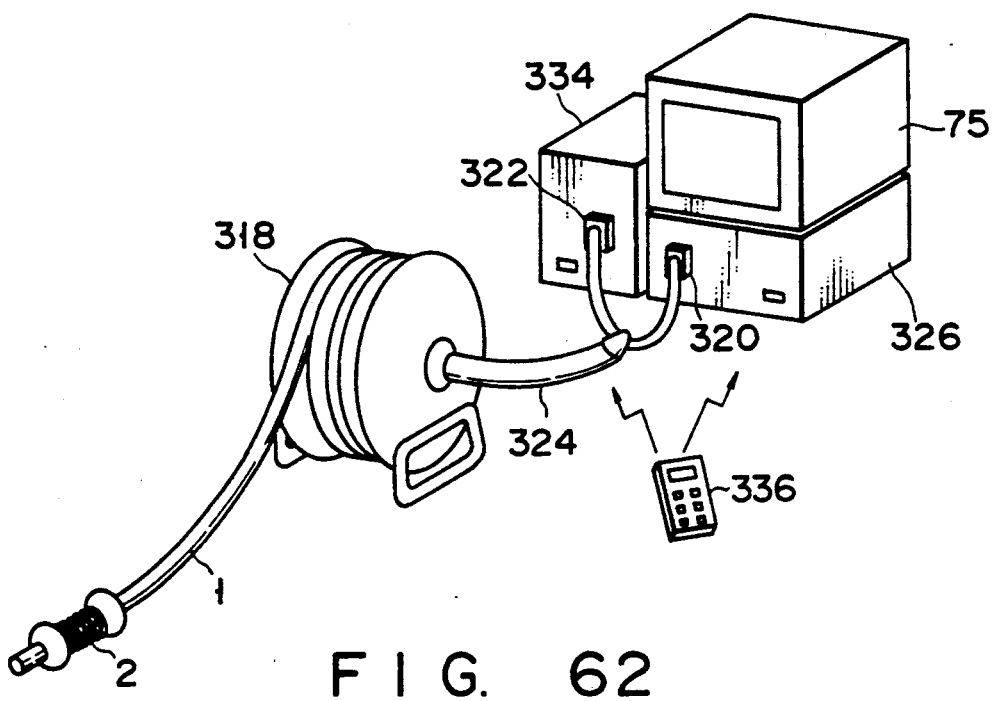
FIG. 62 is an overall perspective view of the seventh embodiment of the invention.

As is shown in FIG. 62, the pipe-inspecting apparatus according to the seventh embodiment of the invention comprises cable 1, self-propelled section 2 coupled to the distal end of cable 1, drum 318 for taking up cable 1, universal cord 324 coupled to the proximal end of cable 1 and extending from drum 318, video processor 326 connected to cord 324 by connector 320, monitor TV 75 connected to video processor 326, fluid control unit 85 coupled to cord 324 by connector 322, and remote controller 336 for controlling monitor TV and fluid control unit 85. Self-propelled section 2 can move in a tubular member, for guiding cable 1 through the tubular member. Video processor 326 has image signal processing circuit and a light source. Fluid control unit 85 has fluid control circuit 314, air-supplying pump 296, and air-discharging pump 298.

Self-propelled section 2 comprises actuator 20, which is a rubber tube, front balloon 31 attached to the forward end of actuator 20, and rear balloon 32 attached to the rear end of actuator 20.

Actuator 20 is covered with a sleeve made of net. When air is supplied into actuator 20, the sleeve allows actuator 20 to expand in the radial direction, restricting the axial expansion of actuator 20. Hence, when actuator 20 is inflated with air, it expands in its radial direction and contracts in is axial direction. The pull, which actuator exerts when it contracts in its axial direction, is great. A pair of tubular caps 338 and 340 are fastened to the ends of actuator 20, respectively. Cable 1 passes through actuator 20 and also through caps 388 and 340, and is fastened to cap 338. Air-supplying tube 27 extends via cable 1 and coupled to actuator 20, to supply air into actuator 20 and discharge air therefrom.

Figure 61:
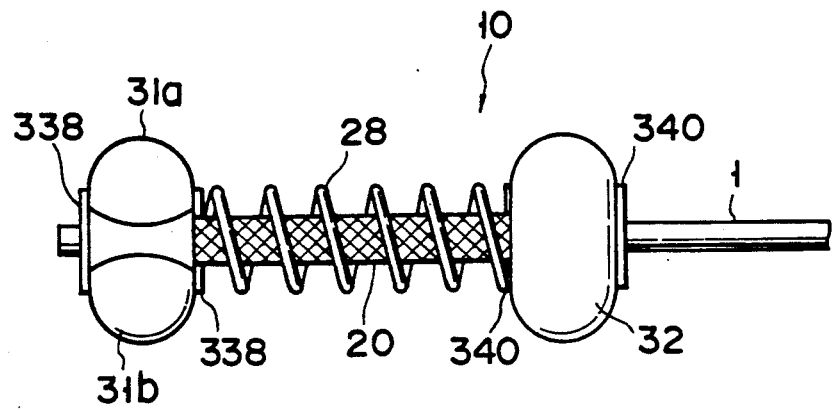
FIG. 61 is a side view showing the self-propelled unit incorporated in a pipe-inspecting apparatus according to a seventh embodiment of the invention.

As is shown in FIG. 61, front balloon 31 consists of two balloons, i.e., upper balloon 31a and lower balloon 31b. These balloons 31a and 31b are mounted on front cap 338. Rear balloon 32 is mounted on the entire circumferential surface of rear cap 340. Air-supplying tubes 37a and 37b extend through cable 1 and are connected to balloons 31a and 31b, respectively, to supply air into balloons 31a and 31b and discharge air from them. Coil spring 28 is wound around actuator 20, and is, hence, interposed between caps 338 and 340.

TV camera 118 is incorporated in the distal end portion of cable 1. The signal cable 119 extends through cable 1 and universal cord 324 and is connected to video processor 326 by means of connector 320.

Light guide fiber 5 also extends through cable 1 from connector 320 to the distal end of cable 1, to supply illumination light to the distal end of cable 1. Air-supplying tubes 27, 37a, 37b, and 38, which extend through cable 1 and are connected to actuator 20, balloon 31a, balloon 31b, and rear balloon 32, are connected to fluid control unit 85 by means of connector 322.

Video processor 326 has a video signal processing circuit and a light source. Video processor 326 processes video signals supplied from TV camera 118 via cable 119, thereby to form a still image of the interior of a tubular member, when remote controller 336 is operated.

As is shown in FIG. 63, fluid control circuit 314 provided in fluid control unit 85 controls switching valve 302 for connecting control valve 306 to air-supplying pump 296 or air-discharging pump 298, and also controls control valve 306 for opening and closing air-supplying tubes 27, 37a, 37b, and 38. Signal receiver 346 is incorporated in fluid control unit 85 to supply control signals from remote controller 336 to fluid control circuit 314. Hence, circuit 314 can be operated in accordance with these control signals.

Figure 64:
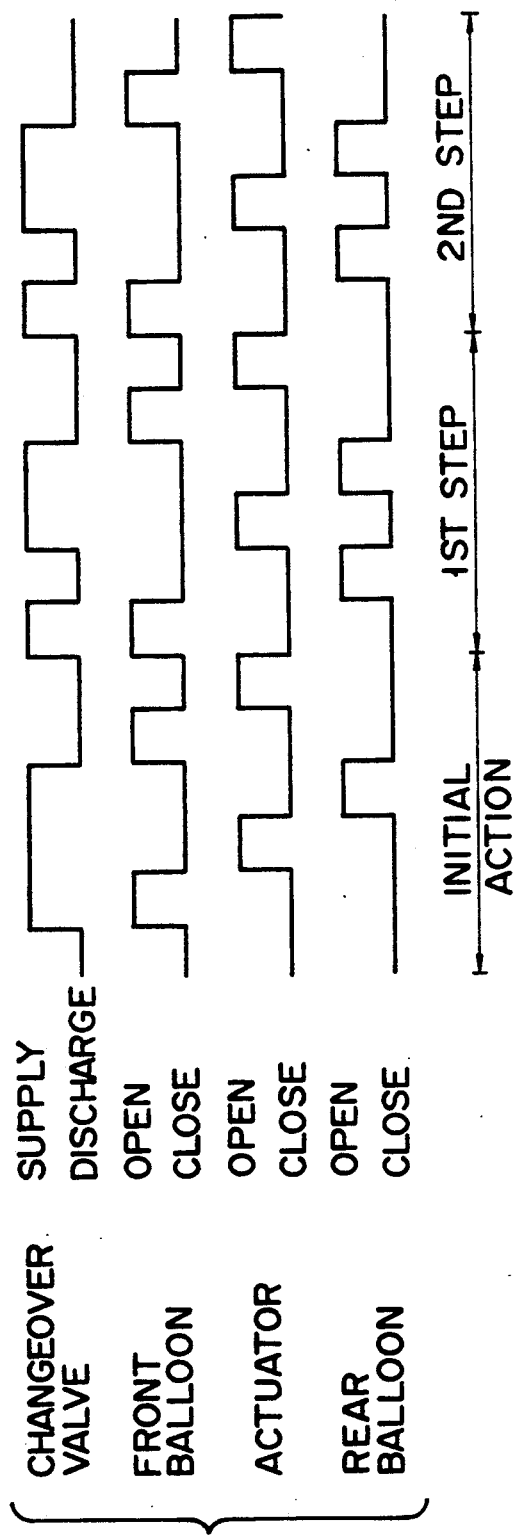
FIG. 64 is a timing chart showing the signals for driving the self-propelled unit shown in FIG. 61.

The operation of the pipe-inspecting apparatus according to the seventh embodiment of the invention will now be expanded with reference to the timing chart shown in FIG. 64.

First, the distal end portion of cable 1 is inserted into a tubular member which is to be inspected. At this time, actuator 20 and balloons 31a, 31b, and 32 are deflated. Then, remote controller 336 is operated to cause self-propelled section 2 to move forward in the tubular member. Remote controller 336 generates and transmits control signals. Signal receiver 346 receives these signals. In accordance with the signals, fluid control circuit 314 controls switching valve 302 and control valve 306, in such a manner as is illustrated in FIG. 64.

First, switching valve 302 connects control valve 306 to air-supplying pump 296, and causes control valve 206 to open air-supplying tubes 37a and 37b. As a result, air is supplied from pump 296 into balloons 31a and 31b. Balloons 31a and 31b are inflated, thus contacting the inner surface of the tubular member. Hence, self-propelled section 2 is held within the tubular member. Next, control valve 306 opens air-supplying tube 27, whereby air is supplied from pump 296 into actuator 20, thus expanding actuator 20 in the radial direction. Actuator 20 contracts in its axial direction, against the force of coil spring 28 wound around it. As a result of this, self-propelled section 2 moves forward in the tubular member, pulling cable 1 farther into the tubular member. Thereafter, control valve 306 opens air-supplying tube 38, thereby supplying air from pump 296 into rear balloon 32. Balloon 32 expands until it contacts the inner surface of the tubular member. Inflated balloon 32 holds self-propelled section 2 steadfast in the tubular member. Then, fluid control circuit 314 causes switching valve 302 to disconnect control valve 306 from air-supplying pump 296 and connect valve 306 to air-discharging valve 298. Simultaneously, circuit 314 causes control valve 306 to close air-supplying tube 38. As a result, pump 298 discharges air from actuator 20 and balloons 31a and 31b. Actuator 20 and balloons 31a and 31b are deflated forthwith. Coil spring 28 makes actuator 20 extend forward, regaining its original length. Finally, circuit 314 makes control vale 306 opens air-supplying tube 28, whereby pump 298 discharges air from rear balloon 32, thus deflating the same.

The sequence of the above-mentioned steps, i.e., the step of supplying air into balloons 31a and 31b, the step of supplying air into actuator 20, the step of supplying air into rear balloon 32, the step of discharging air from balloons 31a and 31b and also from actuator 20, and the step of discharging air from rear balloon 32, is repeated, whereby self-propelled section 2 continues to move forward in the tubular member.

To cause self-propelled section 2 to move backward in the tubular member, it suffices to inflate and deflate balloons 31a and 31b, on the one hand, and rear balloon 32, on the other, in the order opposite to that described above.

The view field of TV camera 118, which is incorporated in the distal end of cable 1, can be shifted up and down, by supplying air into balloons 31a and 31b in controlled amounts. More specifically, when air is pumped into upper and lower balloons 31a and 31b in the same amount, the view field takes a central position as is illustrated in FIG. 65. When more air is pumped into lower balloon 31b than into upper balloon 31a, the view field moves upward, as is shown in FIG. 66.

Front balloon 31 and consists of three or four small balloons, instead of two. When balloon 31 is comprised of three small balloons, the view field of TV camera 118 can be moved in three directions. When balloon 31 consists of four small balloons, the view field of TV camera 118 can be moved in four directions. Moreover, rear balloon 31, not the front one, can consist of a plurality of small balloons, in which case, too, the view field of the TV camera 118 can be moved in various directions. Further, both front balloon 31 and rear balloon 32 can be comprised of a plurality of small balloons. In this case, when any front small balloon is inflated while the diametrically opposite, rear small balloon is deflated, or vice versa, the view field of TV camera 118 can be more shifted.

Figure 67:
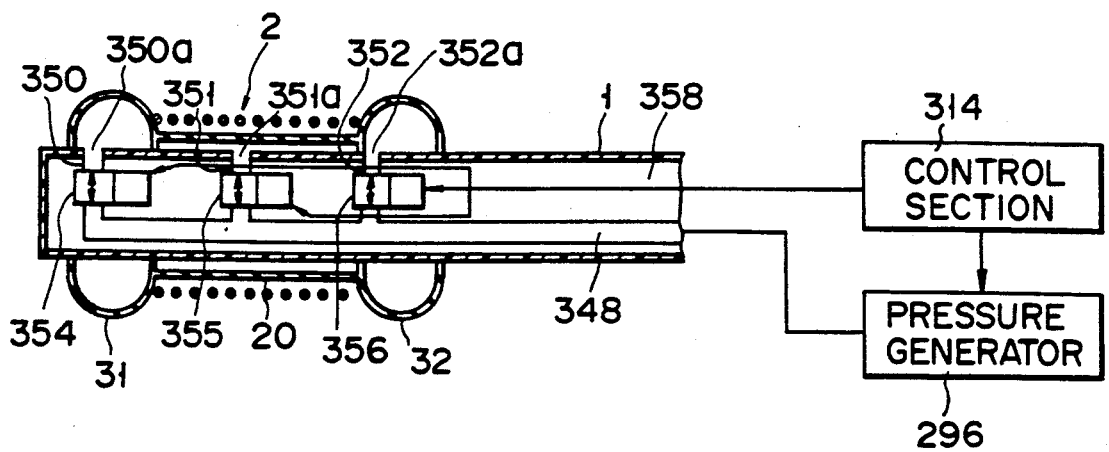
FIGS. 67 and 68 are a longitudinal sectional view and a side view, respectively, of the self-propelled unit incorporated in a pipe-inspecting apparatus according to an eighth embodiment of the present invention.
Figure 68:
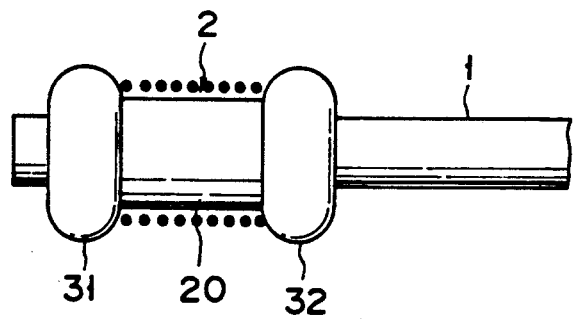

Now, an eighth embodiment of the present invention will be described, with reference to FIGS. 67 and 68. FIG. 67 is a sectional view showing this embodiment, and FIG. 68 shows the outer view thereof.

As is illustrated in FIG. 67, the pipe-inspecting apparatus according to the eighth embodiment comprises cable 1. Air-supplying tube 348 extends throughout cable 1. The proximal end of cable 1 is coupled to pressure generator 296 such as fluid-pressurizing pump. The distal end of cable 1 is forked into three branch tubes 350, 351, and 352. Branch tubes 350, 351, and 352 are connected to port 350a of front balloon 31, port 351a of actuator 20, and 352a of rear balloon 32. Balloons 31 and 32 are actuator 20 are mounted on the outer circumferential surface of cable 1, with actuator 20 interposed between balloons 31 and 31. Hence, the pressurized fluid can be supplied from pressure generator 296 into front balloon 31 via branch tube 350a, into actuator 20 via branch tube 351a, and into rear balloon 32 via branch tube 352a. Small two-way solenoid valves 354, 355, and 356 are incorporated in branch tubes 350a, 351a, and 352a, respectively. Solenoid valves 354, 355, and 356 are connected to control section 314 by means of signal lines 358 extending through cable 1. Therefore, when control section 314, which is located outside cable 1, is operated, solenoid valves are opened or closed, thereby to inflate or deflate actuator 20 and balloons 31 and 32, such that self-propelled section 2 moves in a tubular member, either forward or backward.

It will now be explained how the eighth embodiment is operated. First, self-propelled section 2 is inserted into a tubular member to inspect the interior of this member. Next, control section 314 is operated to move self-propelled section 2 deeper in the tubular member. More specifically, section 314 opens two-way solenoid valve 354. The pressurized fluid is supplied from pressure generator 296 into front balloon 31. Balloon 31 is inflated and contacts the inner surface of the tubular member. The distal end of self-propelled section 2 is, therefore, held in the tubular member. Then, control section 314 opens two-way valve 355, whereby the pressurized fluid is supplied from pressure generator 296 into actuator 20. Actuator 20 expands in its radial direction and contracts in its axial direction, thus pulling cable 1 forward. Next, control section 314 opens two-way valve 356, and the pressurized fluid is supplied from pressure generator 296 into rear balloon 32. Balloon 32 is inflated and contacts the inner surface of the tubular member, thus holding the rear end of self-propelled section 2 in the tubular member. Then, front balloon 31 is deflated, thus releasing the front end of section 2 from the inner surface of the tubular member. At the same time, the pressurized fluid is discharged from actuator 20, whereby actuator 20 contracts in its radial direction and expands in its axial direction, moving front balloon 31 forward. Then, front balloon 31 is inflated again, and rear balloon 32 is deflated.

The sequence of the above-mentioned steps, i.e., the step of inflating front balloon 31, the step of deflating rear balloon 32, the step of inflating actuator 20, the step of inflating rear balloon 32, the step of deflating front balloon 31, and the step of deflating actuator 20, is repeated, whereby self-propelled section 2 further moves forward in the tubular member.

To make self-propelled section 2 to move backward in the tubular member, it suffices to inflate and deflate balloons 31 and 32 in the order opposite to that described above.

With the eighth embodiment it is possible to drive self-propelled section 2 by using only one air-supplying tube 348 extending through cable 1 and connecting section 2 to pressure generator 396. Since only one tube extends through cable 1, cable 1 is thinner than in the case whereby two or more air-supplying tubes necessarily extend through cable 1.

Figure 69:
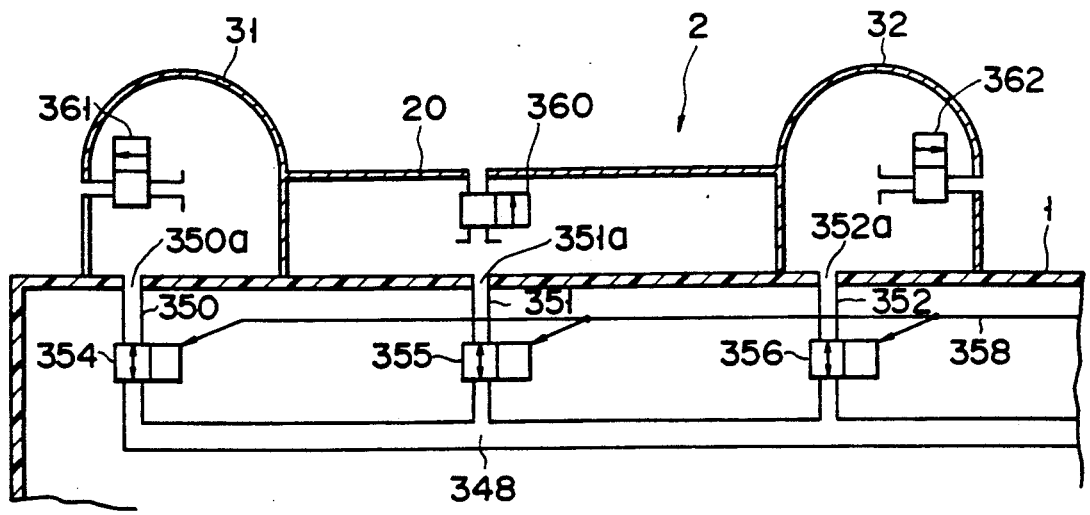
FIG. 69 is a longitudinal sectional view showing part of the self-propelled unit used in a first modification of the eighth embodiment.

FIG. 69 illustrates a first modification of the eighth embodiment of the invention. In this modification, leakage valves 360, 361, 362 are provided within actuator 20, front balloon 31, and rear balloon 32, respectively. These are safety valves for preventing an excessive inflation of actuator 20 and balloons 31 and 32 and, hence, a rupture of thereof.

Figure 70:
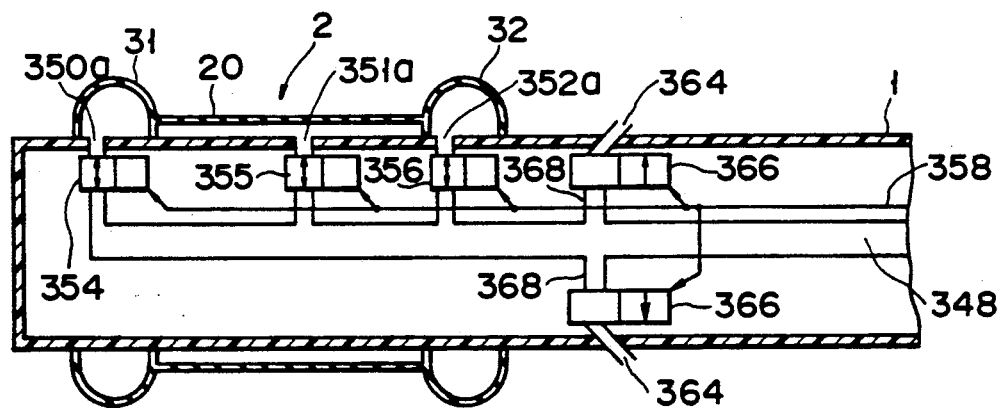
FIG. 70 is a longitudinal sectional view showing part of the self-propelled unit used in a second modification of the eighth embodiment.

FIG. 70 shows a second modification of the eighth embodiment. A plurality of jet nozzles 364 are connected to the outer circumferential surface of cable 1, right behind rear balloon 32. These nozzles 364 incline and project backward from cable 1, and are connected to two-way solenoid valves 366, which in turn are coupled to air-supplying tube 348 by branch tubes 368. When the pressurized fluid is ejected through nozzles 364, cable 1 is moved forward. Since the reaction of the fluid being applied from nozzles 364 is great, cable 1 is pushed forwards at high speed.

Figure 71:
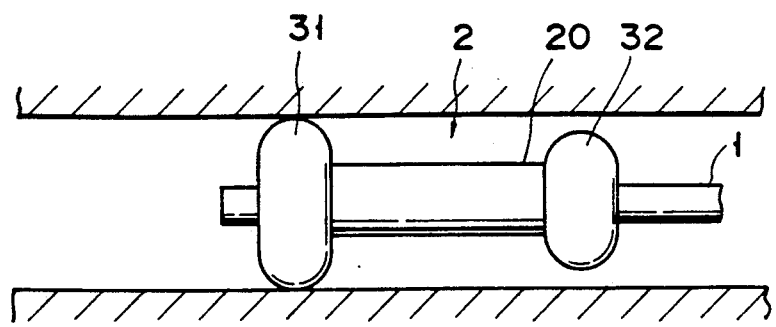
FIGS. 71 to 74 are side views of the self-propelled unit incorporated in a third modification of the eighth embodiment, illustrating the sequence of the movement of the unit in the pipe under inspection.
Figure 72:
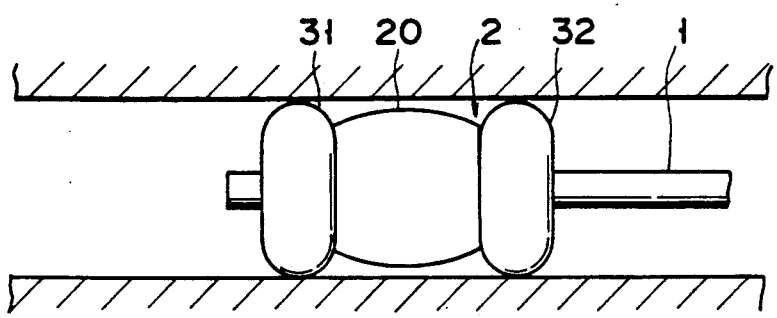
Figure 73:
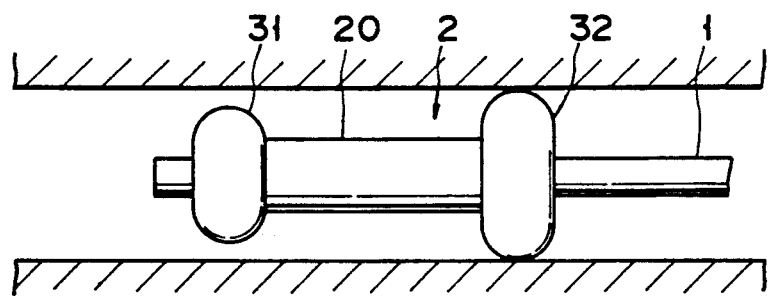
Figure 74:
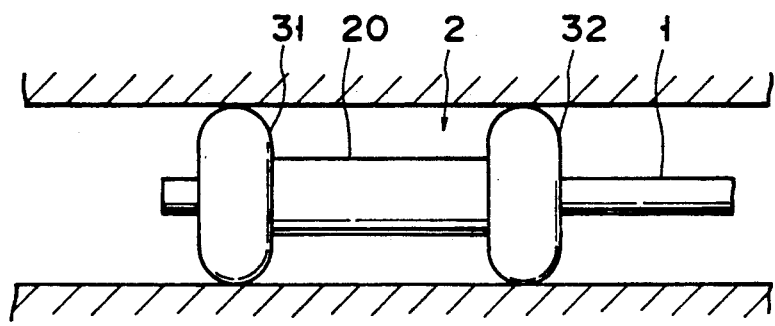

FIGS. 71 to 74 show a third modification of the eighth embodiment. The third modification is characterized in that the fluid, being discharged from area balloon 32 as this balloon 32 is deflated, changing its size from the one shown in FIG. 74 to the one shown in FIG. 71, is supplied into front balloon 31 to inflate balloon 31. This reuse of the pressurized fluid helps to inflate balloon 31 at high speed, and ultimately serves to raise the speed of inserting cable 1 deeper into a tubular member.

FIGS. 75 and 76 illustrate a fourth modification of the eighth embodiment of the present invention. As is shown in FIG. 76, either balloon is designed to collapses onto the circumferential surface of cable 1 when the pressurized fluid is discharged from the balloon. More specifically, either balloon contains wires 370 which are rotatably connected to cable 1 and biased by elastic members 372 (e.g., rubber strings) to rotate rearward. When the pressurized fluid is discharged from the balloon, wires 370 are rotated rearward due to the bias of elastic members 372. As a result, the deflated balloon collapses onto the circumferential surface of cable 1, as is illustrated in FIG. 76.

Since both balloons 31 an 32 collapse onto the circumferential surface of cable 1 whenever they are deflated, it is easy to pull cable 1 out of a tubular member.

FIGS. 77 and 78 show a fifth modification of the eighth embodiment. The fifth modification is identical to the fourth modification (FIGS. 75 and 76), except that ring-shaped member 374 is bonded to the inner surface of either balloon. Member 374 biases the balloon to collapse. Therefore, when the pressurized fluid if discharged from the balloon, the balloon collapses due to the bias of ring-shaped member 374.

A pipe-inspecting apparatus according to a ninth embodiment of the invention will now be described reference to FIG. 79 through FIG. 82.

Figure 79:
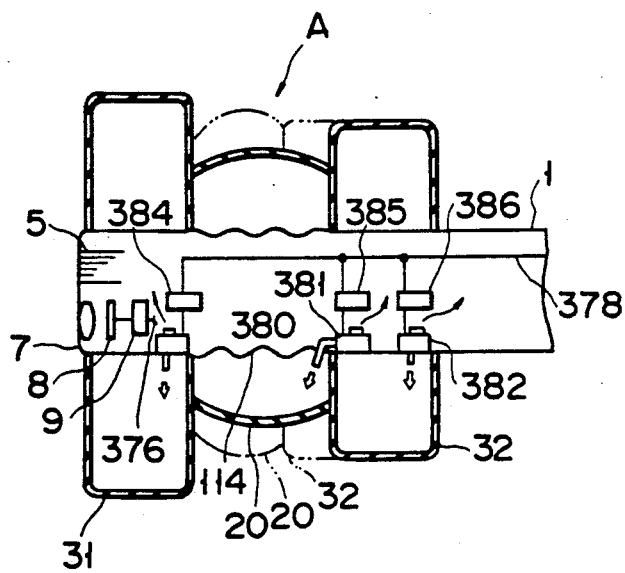
FIG. 79 is a longitudinal sectional view showing the self-propelled unit incorporated in a pipe-inspecting apparatus according to a ninth embodiment of the present invention.

As is shown in FIG. 79, the pipe-inspecting apparatus according to the ninth embodiment has cable 1 which can be inserted into a tubular member which is to be inspected. The distal end portion of cable 1 contains an illumination means such as light guide fiber 5, solid-state image pickup element (CCD) 8, an observation means including objective lens 7. Image pickup element 8 is connected to transmitter circuit 9 which is also incorporated in the distal end portion of cable 1. Signal line 376 extends through cable 1, and is connected at one end to circuit 9 at one end, and at the other end to a video processor located outside cable 1. A TV monitor is connected to the video processor. The video processor converts the electrical signals, which element 8 has generated, into video signals. The video signals are input to the TV monitor, and the TV monitor displays the image of the interior of the tubular member.

Figure 80:
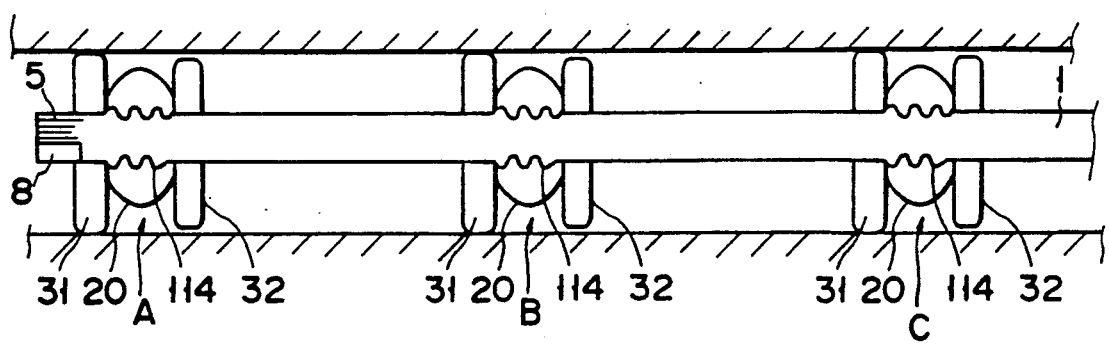
FIG. 80 is a side view showing the self-propelled section of the ninth embodiment.

FIG. 80 is an outer view of the pipe-inspecting apparatus according to the ninth embodiment. As is illustrated in FIG. 80, three self-propelled units A, B, and C are mounted on the distal end portion of cable 1. Each self-propelled unit comprises bellows 114, actuator 20 made of an elastic tube loosely mounted on bellows 114, and two balloons 31 and 32 coupled to the ends of actuator 20.

One signal line 378 extends throughout cable 1. The distal end of this line 378 is connected to drive circuits 384, 385, and 386, which are provided within the distal end portion of cable 1 for any one of self-propelled units A, B, and C. These drive circuits 384, 385, and 386 are connected to pumps 380, 381, and 382 for supplying and discharging air into and from balloon 31, actuator 20, and balloon 32, respectively. Pumps 380, 381, and 382 are bimorph pumps each having two ports. The two ports of pump 380 communicates with front balloon 31 and the interior of cable 1, respectively. The two ports of pump 381 communicate with actuator 20 and the interior or cable 1, respectively. The two ports of pump 382 communicates with rear balloon 32 and the interior of cable 1, respectively. Pumps 380, 381, and 382 can be solenoid pumps or motor-driven pumps, instead of bimorph pumps.

Figure 81:
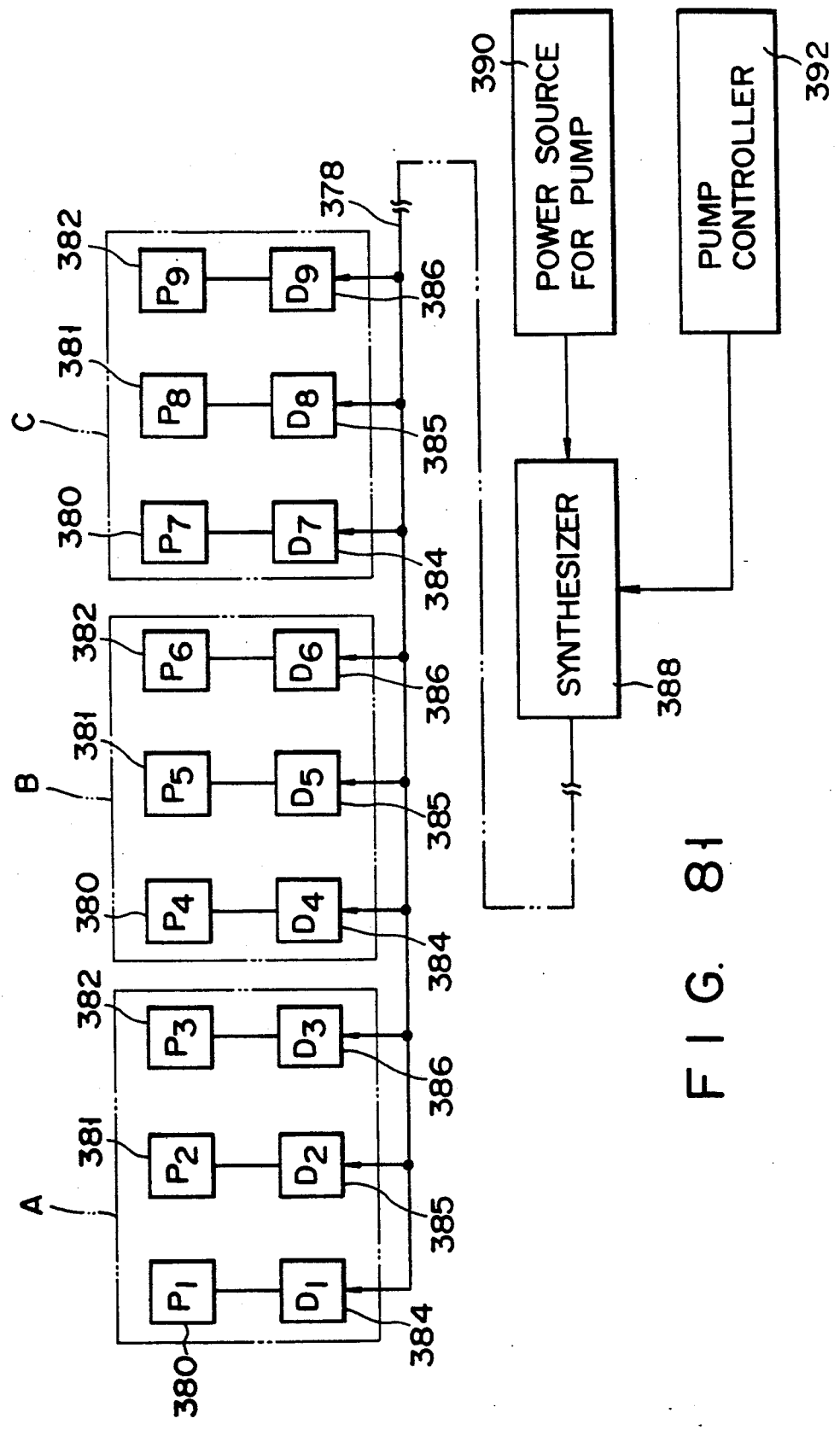
FIG. 81 is a block diagram illustrating the control circuit incorporated in the ninth embodiment.

As is clearly shown in FIG. 81, the proximal end of signal line 378 is connected to synthesizer 388 arranged outside cable 1. Power source for pumps, e.g., a 50 Hz AC power source, is coupled to synthesizer 388. Also, pump controller 392 is connected to synthesizer 388. Pump controller 392 outputs pump control signals having a frequency of several KHz to several MHz, whereas power source 390 supplies a current to synthesizer 388. Synthesizer 388 combines each pump control signal and the current supplied from power source 390, producing a drive signal of a specific frequency. Synthesizer 388 supplies the drive signal to drive circuits 384, 385, and 386 incorporated in each self-propelled unit. In accordance with this drive signal, drive circuits 384, 385, and 386 drive pumps 380, 381, and 382. As a result, air is supplied and discharged into and from actuator 30 and balloons 31 and 32 of each self-propelled unit.

More specifically, synthesizer 388 can generate nine drive signals of different frequencies f1 to f9 for driving nine drive circuits D1 to D9 which are connected to pumps nine pumps P1 to P9. Drive circuits D1 to D3 and pumps P1 to P3 are incorporated in self-propelled unit A. Drive circuits D4 to D6 and pumps P4 to P6 are provided in self-propelled unit B. Drive circuits D7 to D9 and pumps P7 to P9 are arranged in self-propelled unit C. Pumps P1 to P9 can be operated independently of one another, to supply and discharge air into and from actuators 20 and balloons 31 and 32 of self-propelled units A, B, and C. Drive circuits D1 to D9 (FIG. 81) are identical in structure. Hence, only drive circuit 384 (D1) will be described with reference to FIG. 82.

Figure 82:
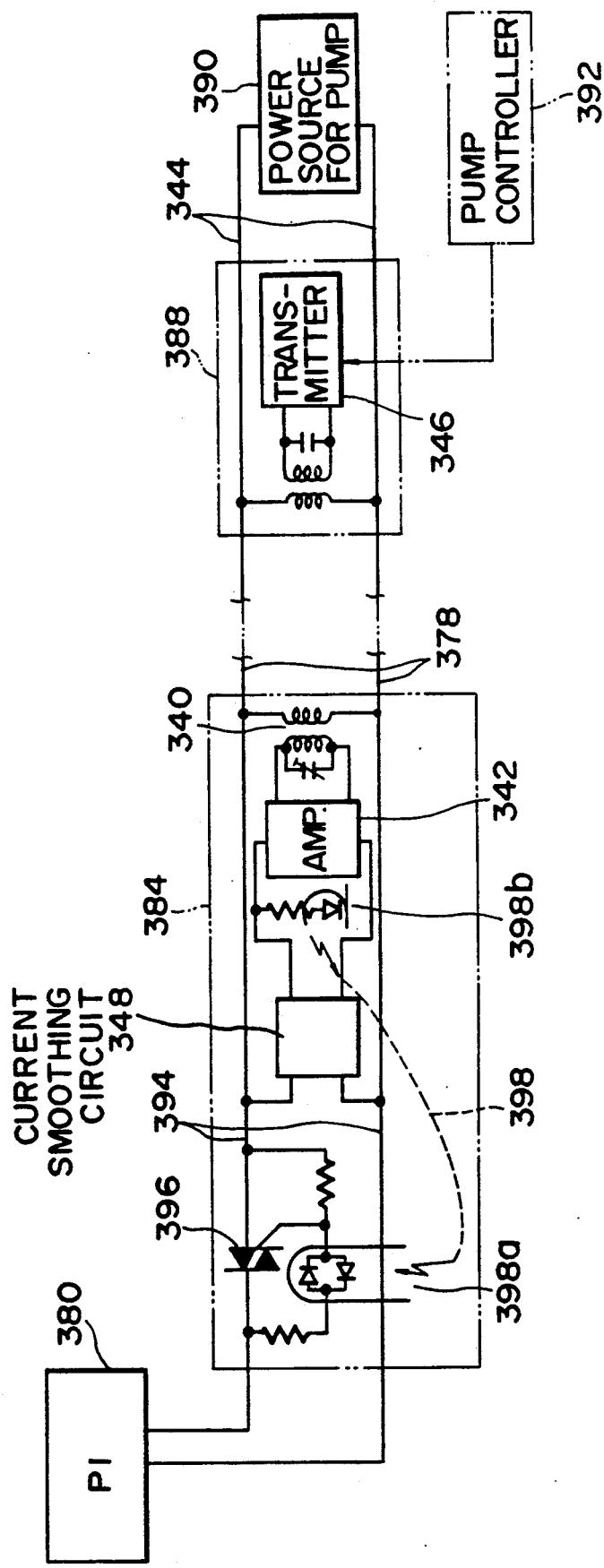
FIG. 82 is a block diagram showing, in detail, part of the control circuit shown in FIG. 81.

As is clearly illustrated in FIG. 82, drive circuit 384 comprises triac 396, photocoupler 398, resonator 340, amplifier 342. Triac 396 is connected in one of power-supply lines 394 which are coupled, at one end, to pump 380 (P1). Photocoupler 398 is used to drive triac 396; it has light-receiving element 398a and light-emitting element 398b, which oppose each other. Light-receiving element 398a is connected in parallel to triac 396. Resonator 340, which defines frequency f1, is coupled in parallel to power-supply lines 394. The output of resonator 340 is connected to the input of amplifier 342. The output of amplifier 342 is coupled to light-emitting element 398b of photocoupler 398.

All other drive circuits D2 to D9 are also connected in parallel to power-supply lines 384, though not illustrated in FIG. 82.

As is shown in FIG. 82, synthesizer 388 includes transmitter 346. Transmitter 346 is connected in parallel to power-supply lines 344 coupled to power source 390 for pumps P1 to P9. Transmitter 346 is also coupled to pump controller 392. Power-supply lines 344 are connected in parallel to drive circuits D1 to D9 by power-supply lines 378. Synthesizer 388 combines each pump control signal supplied from pump controller 392 and the current supplied from power source 390, thereby generating a drive signal of a specific frequency. This drive signal drives resonator 340 which is turned with its frequency. Photocoupler 398 coupled to this resonator 340 operated. Triac 396 coupled to photocoupler 398 drives the pump, which supplies air into, or discharges air from, actuator 20 or balloon 31 or 32.

Each drive circuit further comprises current-smoothing circuit 348 connected to amplifier 342. This circuit 348 supplies a DC current to amplifier 342.

Pumps 380, 381, and 382 of each self-propelled unit supply and discharge air into and from balloon 31, actuator 20, and balloon 32, respectively, under the control of drive signals which synthesizer 388 has generated in accordance with the pump control signals supplied from pump controller 392. As a result, actuator 20 and balloons 31 and 32 are inflated and deflated, whereby the self-propelled unit moves in a tubular member, forward or backward.

The operation of the ninth embodiment described above will now be explained. First, self-propelled units A, B, and C are inserted into a tubular member which is to be inspected. Then, the operation section (not shown) connected cable 1 is operated to move units A, B, and C. Since units A, B, and C move in the same way, only will it is explained how self-propelled unit A moves in the tubular member.

When the operation section (not shown) is operated so as to move self-propelled units A, B, and C forward in the tubular member, pump controller 392 supplies pump control signals to synthesizer 388. Synthesizer 388 superposes these pump control signals on the current supplied from power source 390, thereby producing pump drive signals having frequencies f1 to f9. Resonators 340a, 340b, and 340c, which are built in pumps 380, 381, 382 incorporated in unit A, operate in response to pump drive signals having frequencies f1, f2, and f3, respectively. First, pump 380 is driven, supplying air into front balloon 31. Balloon 31 is forthwith inflated until it contacts the inner surface of the tubular member. The distal end of unit A is thereby held in the tubular member. Next, pump 381 is driven, supplying air into actuator 20. Actuator 20 expands in its radial direction and, at the same time, contracts in its axial direction. As a result of this, the rear end of self-propelled unit A moves forward. Then, pump 382 is driven, thus supplying air into rear balloon 32. Balloon 32 is inflated until it contracts the inner surface of the tubular member, whereby the rear end of unit A is held in the tubular member. Hence, unit A as a whole takes an advanced position. Thereafter, pump 380 is driven, this time, discharging air from front balloon 31. Balloon 32 is deflated, thus releasing the distal end of unit A from the inner surface of the tubular member. At the same time, pump 381 is driven, discharging air from actuator 20. Actuator 20 therefore contracts in its radial direction and expands in its axial direction. As a result, front balloon 31 moves forward in the tubular member. Again, the same sequence of steps, i.e., the step of driving pump 380 to inflate balloon 31, the step of driving pump 381 to inflate actuator 20, the step of driving pump 382 to inflate balloon 32, and the step of driving pumps 380 and 381 to deflate balloon 31 and actuator 20, is repeated, whereby unit A further moves forward in the tubular member.

Other self-propelled units B and C move forward, substantially at the same time in the same way as unit A has moved forward. Units A, B, and C cooperate to pull cable 1 forward.

In order to move self-propelled units A, B, and C backward in the tubular member, the operation section is operated, thus performing the above-mentioned sequence of steps the other way around.

Since pumps 380, 381, and 382 are built in each self-propelled unit, less components are required to move units A, B, and C. Owing to this reduction in the necessary number of components, cable 1 can be made more slender.

Figure 83:
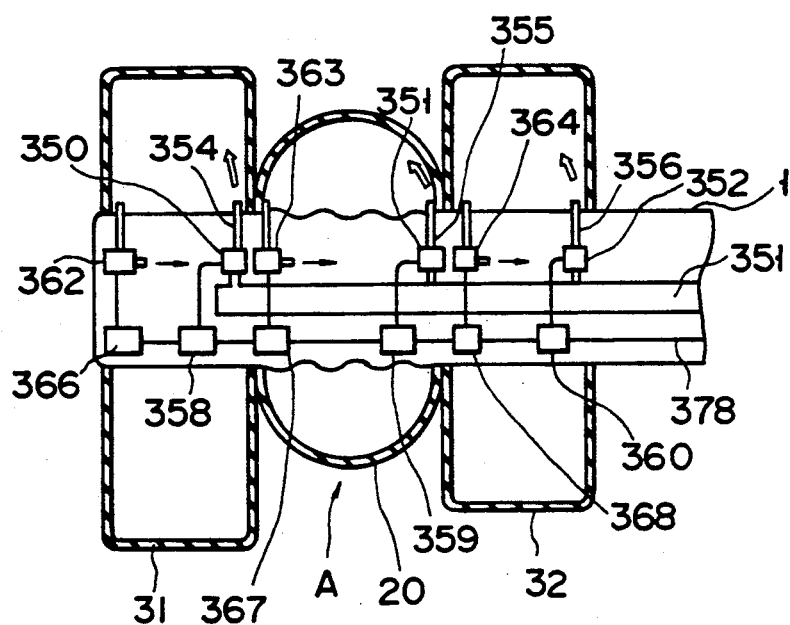
FIG. 83 is a longitudinal sectional view of the self-propelled unit used in a modification of the ninth embodiment.

FIG. 83 illustrates a modification of the ninth embodiment. This modification is different from the ninth embodiment in that valves (e.g., servo valves) are used in place of pumps 380 to 382 in each of the self-propelled unit, to supply pressurized fluid into actuator 20 and balloons 31 and 32. More specifically, air-supplying tube 351 extends through cable 1, for supplying compressed air. This tube 351 is forked into three branch tubes 354, 355, and 356. Branch tubes 354, 355, and 356 are connected to front balloon 31, actuator 20, and rear balloon 32, respectively. Valves 350, 351, and 352 are connected in branch tubes 354, 355, and 356, and also coupled to drive circuits 358, 359 and 360 of the same type as used in the ninth embodiment. Drive circuits 358, 359, and 360 drive valves 350, 351, and 352 in accordance with the drive control signals supplied through signal line 378. That is, drive circuits 358, 359, and 360 open and close valves 350, 351, and 352, thereby supplying the compressed fluid into actuator 20 and balloons 31 and 32. Each self-propelled unit further comprises valves 362, 363, and 364 for discharging the fluid from front balloon 31, actuator 20, and rear balloon 32, and also drive circuits 366, 367, and 368 for opening and closing valves 362, 363, and 364.

In the above modifications, the compression spring is omitted from the figures.

Figure 84:
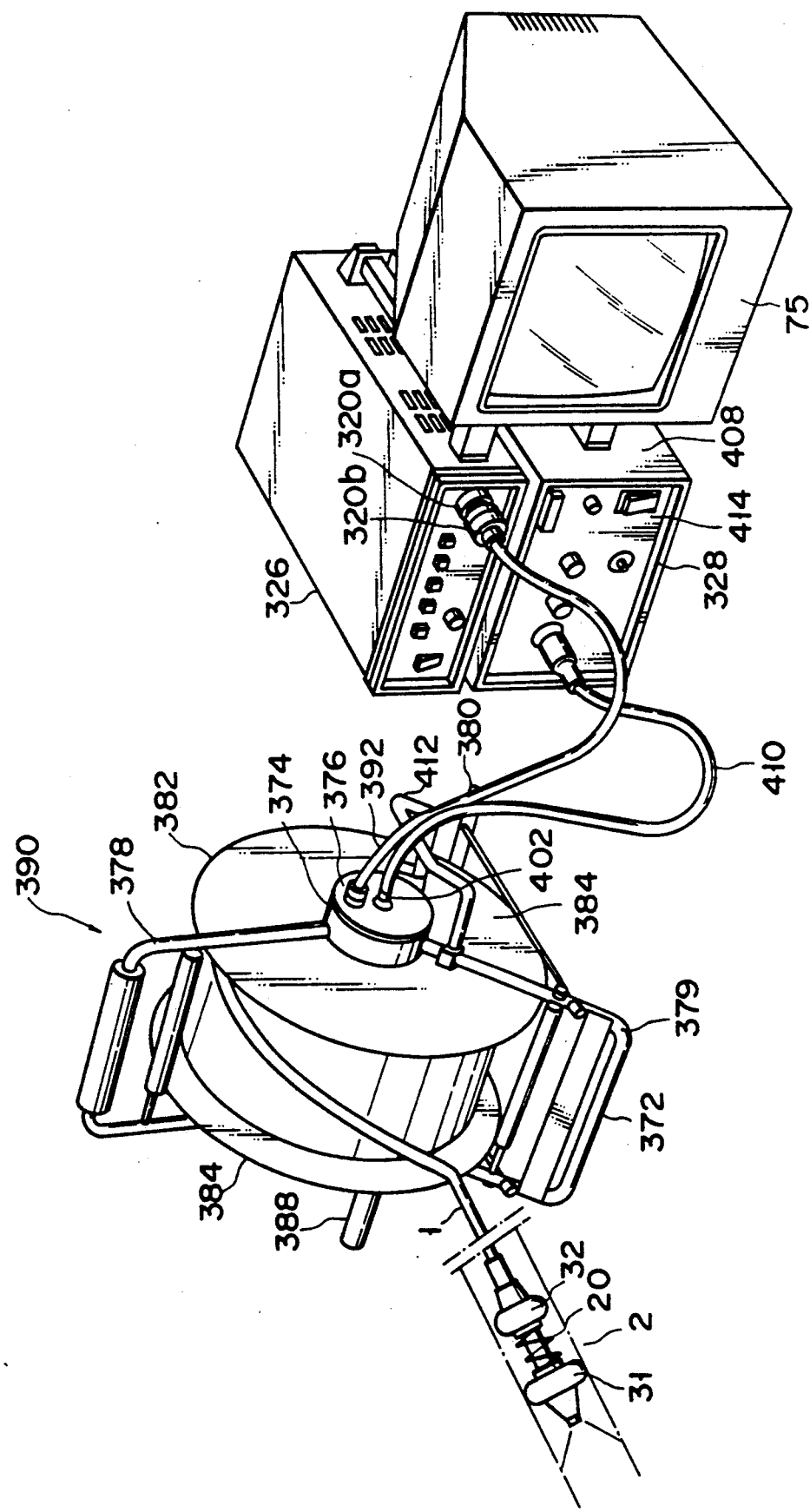
FIG. 84 is a perspective view showing a pipe-inspection apparatus according to a tenth embodiment of the invention.
Figure 85:
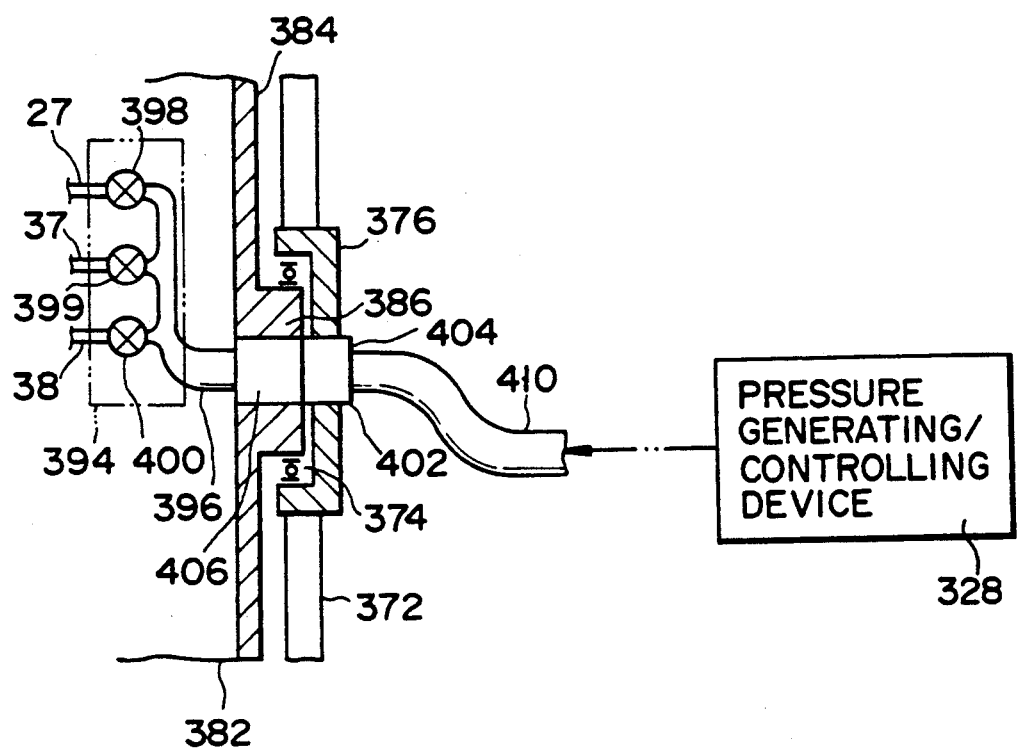
FIG. 85 is a longitudinal sectional view of the rotary coupler which is mounted on the drum unit incorporated in the tenth embodiment.

Now, the pipe-inspecting apparatus according to a tenth embodiment of this invention will be described, with reference to FIGS. 84 to 86. FIG. 84 is a perspective view of the tenth embodiment. As this figure shows, the apparatus has drum unit 390. Unit 390 comprises drum 382, frame 372, and two ball bearings 474 supporting drum 382 to frame 372. Frame 372 is made of three U-shaped pipe members 378, 379, and 380 which are fastened to the circumferential surfaces of the cases 376 of ball bearings 374. Of these pipe members lower members 379 and 380 are used as legs. Upper pipe member 378 has a handle.

Drum 382 is rotatably supported between ball bearings 374. Two disks 384 are connected to the ends of drum 382. As is shown in FIG. 85, each disk 384 has hollow shaft 386. Shaft 386 is rotatably inserted in ball bearing 374, so that drum 382 can rotate around the axis of shafts 386. As is illustrated in FIG. 84, lever 388 is attached to the left side of drum 382. When lever 388 is operated, drum 382 is rotated. The proximal end of long cable 1 is connected to the circumferential surface of drum 382 and communicates with the interior of drum 382. Cable 1 can therefore be wound around drum 382.

Various components of a bore scope, such as an illumination means comprising a lamp, a light-applying lens, and an optical fiber, an observation means comprising a solid-state image pickup element (CCD) and an objective lens, and the like, are incorporated in the distal end portion of cable 1. The signal line connected to the solid-state image pickup element extends through cable 1. It is connected electrically to video processor 326 by the brush assembly provided within drum 382 and signal cable 392 attached to case 376. Video processor 326 is connected to TV monitor 75. The electrical signal generated by the solid-state image pickup element is thus supplied to video processor 326. Video processor 326 converts this signal into video signal, which is supplied to TV monitor 75. TV monitor 75 displays the image scanned by the solid-state image pickup element. The lamp of the illumination means is connected to a power-supply device. Video processor 326 has connector 320a on its front. Signal cable 392 has connector 320b at its tip. When connector 320b is inserted into connector 320a, cable 392 is connected to video processor 326.

The self-propelled unit of self-propelled section 2 is mounted on the distal end portion of cable 1. The self-propelled unit comprises elastic tube 20 and two balloons 31 and 32 fixed to the ends of tube 20. Tube 20 is made of elastic material and loosely mounted on cable 1. Both balloons 31 and 32 are also made of elastic material such as rubber. Three air-supplying tubes 27, 37, and 38 are connected, at the distal end, to tube 20, front balloon 31, and rear balloon 32, respectively, and at the proximal end, to control valve device 384 provided in drum 382 as is shown in FIG. 85. Control valve device 384 comprises header 396 and three valves 398, 399, and 400. Valves 398, 399, and 400, which are, for example, servo valves, are connected at one end to header 396 and at the other end to air-supplying tubes 27, 37, and 38, respectively.

Header 396 of control valve device 394 is connected to pressure generating/controlling device 328 by rotary coupler 402. Video processor 326 is also connected to device 328. As is shown in FIG. 85, rotary coupler 402 consists of rotatable, cylindrical input port 404 and fixed cylindrical output port 406. It includes a seal (not shown) interposed between the opposing ends of ports 404 and 406. Hence, air can flow through ports 404 and 406, without leaking through between these ports. Rotary coupler 402 is inserted in shaft 386 and case 376. Outlet port 406 is connected to header 396 of control valve device 394.

Pressure generating/controlling device 328 comprises case 408, a pressurizing means provided in case 408, and a sequence controller also provided in case 408. The pressurizing means is, for example, an air-pressurizing pump for supplying a pressurized air. The sequence controller is designed for controlling the pressurizing means. Tube 410 for supplying the air from device 328 to section 2 extends from case 408 and is connected to input port 404 of rotary coupler 402. Therefore, the pressurized air can be supplied from device 328 into air-supplying tubes 27, 37, and 38 through rotary coupler 402 and through control valve device 394. Valves 398, 399, and 400 of device 394 are opened or closed, thereby to inflate and deflate tube 20, front balloon 31, and rear balloon 32 of self-propelled section 2. Hence, self-propelled section 2 can move forward or backward in a tubular member which is being inspected.

Guard 412 is attached to pipe members 379 and 380, for preventing signal cable 392 and air-supplying tube 410, both connected to case 376, from being taken up around drum 382.

The operation of the tenth embodiment will be explained. First, self-propelled section 2 is inserted into a tubular member to inspect the interior of this member. Operation switch 414 mounted on the front of pressure generating/controlling device 328 is then moved to the first position, thereby to cause section 2 to move forward in the tubular member. When switch 414 is moved to the first position, control valve device 394 opens valve 399, thus supplying the pressurized air into front balloon 31 via air-supplying tube 37. As a result, balloon 31 is inflated, contacting the inner surface of the tubular member. Next, device 394 opens valve 398, whereby air supplied into elastic tube 20 via air-supplying tube 27. Tube 20 contracts in its axial direction, thereby pulling rear balloon 32 toward front balloon 31, and thus causing self-propelled section 2 to move forward. Thereafter, device 394 opens valve 400, thus supplying the pressurized air into rear balloon 32 through air-supplying tube 38. As a result, balloon 32 is inflated and contacts the inner surface of the tubular member, and section 2 is held in an advanced position. Then, front balloon 31 is deflated, and elastic tube 20 is simultaneously deflated. Tube 20 expands in its axial direction due to the force of compression spring 28, whereby front balloon 31 is moved forward. The sequence of the steps of inflating balloon 31, inflating tube 20, inflating balloon 32, and deflating balloon 31 and tube 20, is repeated, and self-propelled section 2 automatically moves forward in tubular member 101, so that the interior of member 101 is inspected.

After the interior of the tubular member has been inspected, section 2 must be moved backward to pull cable 1 out of the tubular member. To move section 2 backward in the tubular member, it suffices to move switch 414 to the second position. When switch 414 is so moved, control valve device 384 operates such that the steps of the above-mentioned sequence are performed in the opposite order. As cable 1 is pulled from the tubular member, drum 382 is rotated to take up cable 1. After cable 1 has been taken up around drum 382, signal cable 392 and tube 410 are disconnected from video processor 326 and pressure generating/controlling device 328. Then, drum unit 390, video processor 326, and device 328 can be independently transported. In particular, drum 382 can be more easily transported than in the case where it remains connected to both video processor 326 and pressure generating/controlling device 328.

Figure 86:
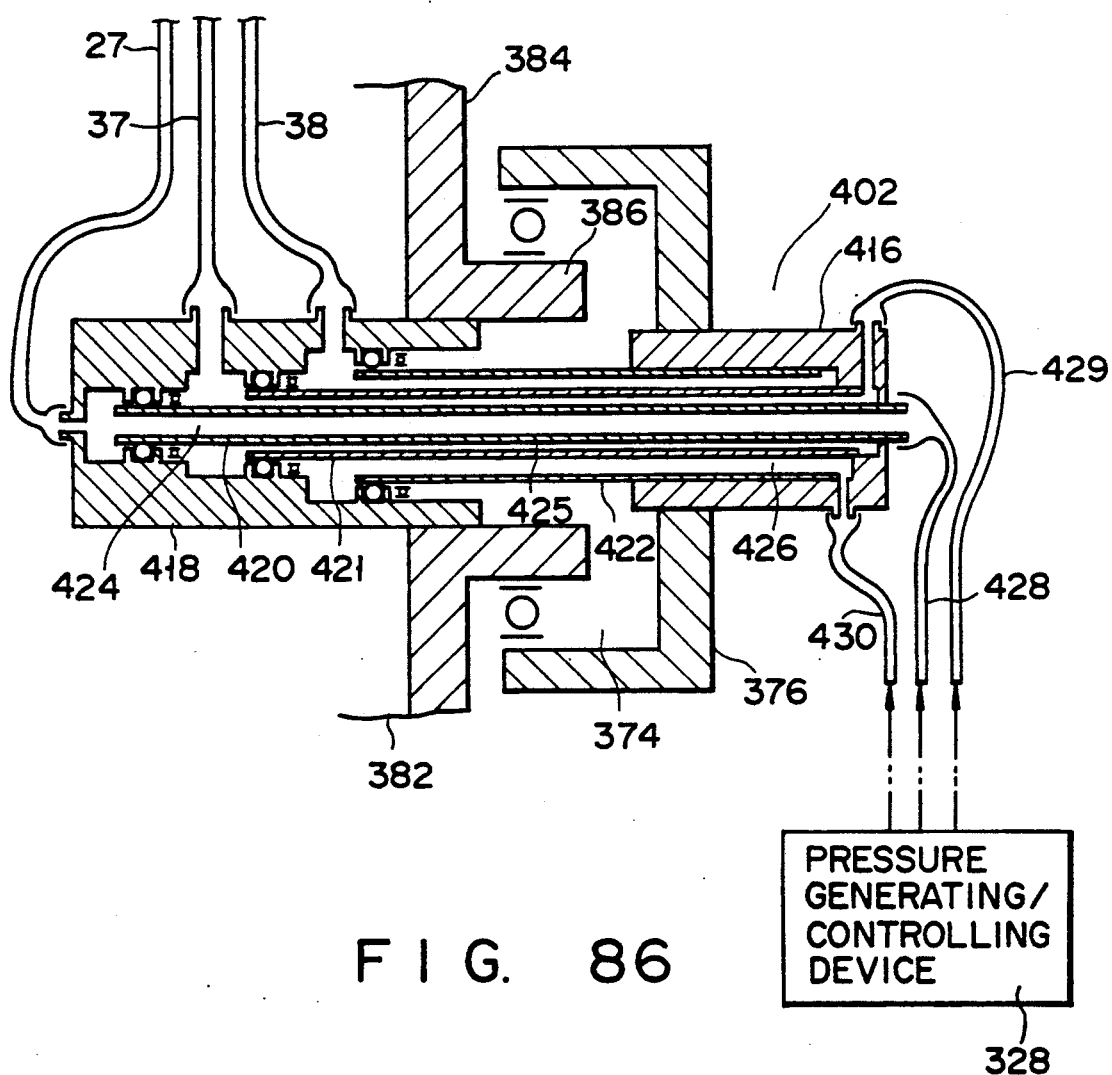
FIG. 86 is a longitudinal sectional view of a modification of the rotary coupler.

FIG. 86 is a sectional view showing a modification of rotary coupler 402. Unlike rotary coupler 402 having one air passage, the modified rotary coupler has three air passages 424, 425, and 426 which are defined by three pipes 420, 421, and 422 which connect inlet-port cylinder 416 and outlet-port cylinder 418. Pipes 420, 421, and 422 are coaxially arranged, pipe 422 surrounding pipe 421, and pipe 421 surrounding pipe 420. Air-passages 424, 425, and 426 are connected, at one end, to air-supplying tubes 27, 37, and 38, and, at the other end, to three air-supplying tubes 428, 429, and 430 which are connected to pressure generating/controlling device 328. Due to the use of the three tubes connecting inlet port of rotary coupler 402 and device 328, the modified rotary coupler does not require control valve device 394, rendering drum unit 390 lighter and easier to transport. In this instance, control valve device 394 is incorporated in pressure generating/controlling device 328. Air-supplying tubes 428, 429, and 430 can be replaced by three tubes having different diameters and arranged coaxially as pipes 420, 421, and 422 which define three air-passages 424, 425, and 426. If this is the case, device 328 can be more easily connected to rotary coupler 402.

A pipe-inspecting apparatus according to an eleventh embodiment of the invention will now be described with reference to FIGS. 87 to 91.

FIG. 87 is a perspective view of the apparatus according to the eleventh embodiment. Drum unit 390 has base 434 having U-shaped frame 436 projecting upward. Drum 382 is rotatably supported by two bearings 438 fastened to the upper ends of U-shaped frame 436. Drum 382 is formed of hollow cylinder 440, and two disks 442 fixed to the ends of hollow cylinder 440. It is the center portions of these disks 442 which are supported by bearings 438. The proximal end of long cable 1 is connected to the circumferential surface of drum 382. Thus, cable 1 can be taken up around drum 382.

Various components of a bore scope, such as an illumination means comprising a lamp and a light guide fiber 5, an observation means comprising solid-state image pickup element 8 and objective lens 7, and the like, are incorporated in the distal end portion of cable 1. Light guide fiber 5 extends through cable 1, and its input end is coupled to the output of light-source device 444 located within hollow cylinder 440 of drum 382. Device 444 comprises case 448, cooling fan 446 attached to case 448, and lamp 450 accommodated in case 448. Light-source device 444 further comprises light-applying lens 452 and prism 454. Lens 452 and prism 454 cooperate to apply the emitted by lamp 450 to the output end of fiber 5. Fan 456 is provided for cooling lamp 450.

A signal line extends through cable 4. One end of this line is connected to image pickup element 8 (hereinafter called "CCD"). The other end of the signal line connected to TV camera controller 458 which is arranged hollow cylinder 440 and designed to drive CCD 8. TV camera controller 458 is connected to operation section 3 by means of rotary transformer 460 which is coaxial with drum 382. Operation section 3 is coupled to TV monitor 75. Hence, TV monitor 75 can display the image of the interior of the tubular member, which CCD 8 has scanned.

Figure 89:
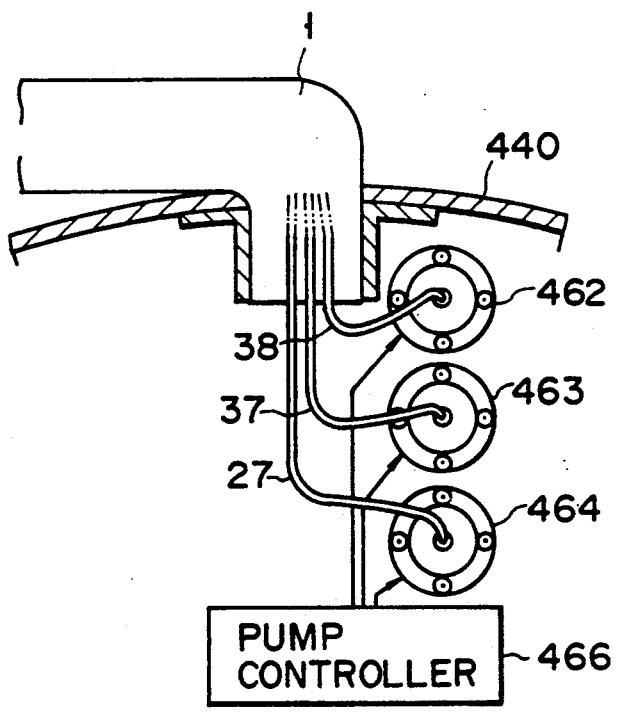
FIG. 89 schematically shows the fluid-pressurizing device incorporated in the eleventh embodiment.
Figure 90:
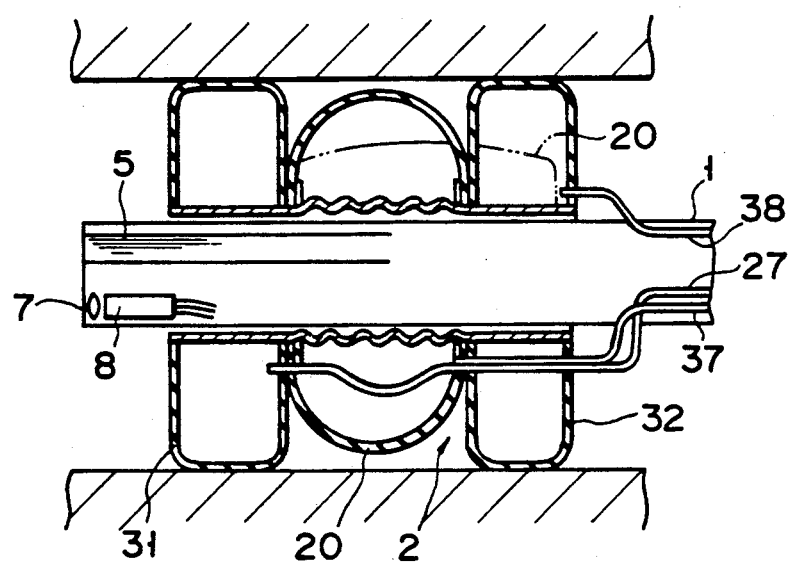
FIG. 90 is a longitudinal of the self-propelled unit used in the eleventh embodiment.

Self-propelled section 2 is loosely mounted on the distal end portion of cable 1. Self-propelled section 2 has elastic tube 20 and two balloons 31 and 32 fixed to the ends of tube 20. Tube 20 is made of elastic material and loosely mounted on cable 1. Both balloons 31 and 32 are also made of elastic material such as rubber. Three air-supplying tubes 27, 37, and 38 are connected, at the distal end, to tube 20, front balloon 31, and rear balloon 32, respectively, and at the proximal end, to three pumps 462, 463, and 464 which are provided in hollow cylinder 440 of drum 382, along with light-source device 444 and TV camera controller 458, as is illustrated in FIG. 89. Pumps 462, 463, and 464 are connected to pump controller 466 by three signal lines. These signal lines are connected to operation section 3 by means of rotary transformer 460.

Figure 88:
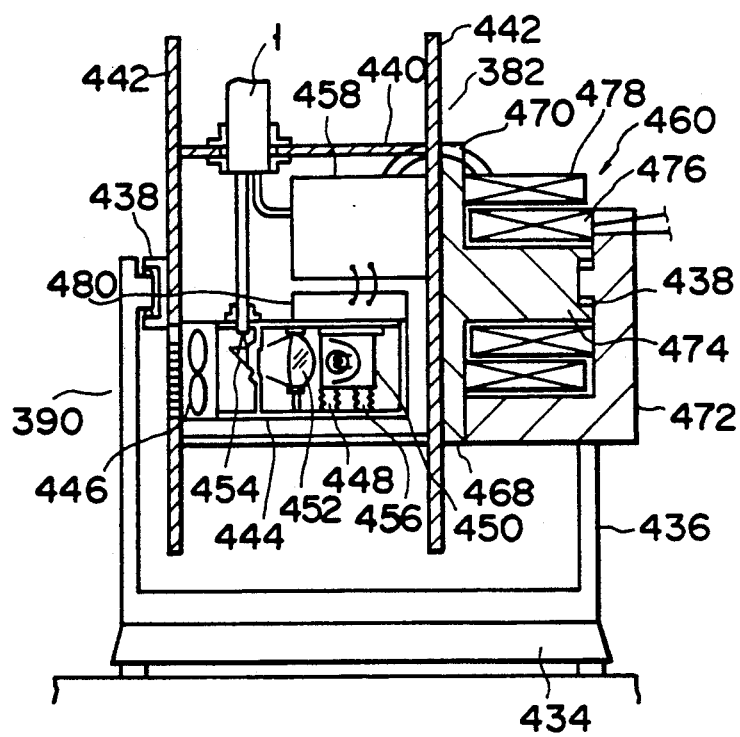
FIG. 88 is a partially sectional view illustrating the drum unit incorporated in the eleventh embodiment.

As is shown in FIG. 88, rotary transformer 460 has a core which also functions as a bearing. More precisely, transformer 460 has disk 468 coaxially fastened to right disk 442 of drum 382, and shaft 474 coaxially projecting from this disk 386. L-shaped core 472 is attached to right arm of frame 436 and located in front of shaft 474. Shaft 474 has a hole, and bearing 438 is fitted in this hole. Core 472 has a projection inserted in bearing 438. Hence, drum 382 can be rotated around shaft 474. Cylindrical primary coil 476 is fastened to L-shaped core 472 and positioned coaxially with shaft 474 and surrounding shaft 474. Cylindrical secondary coil 487 is fixed to disk 468 and positioned coaxially with primary coil 476 and surrounding coil 476. Therefore, electrical signals (high-frequency ones, and low-frequency ones) can be transmitted between primary coil 476 and secondary coil 478 even while drum 382 is rotating. Rotary core 470 and fixed core 472 constitute a closed magnetic loop which achieves an electric coupling between the primary and secondary units of rotary transformer 460.

Figure 91:
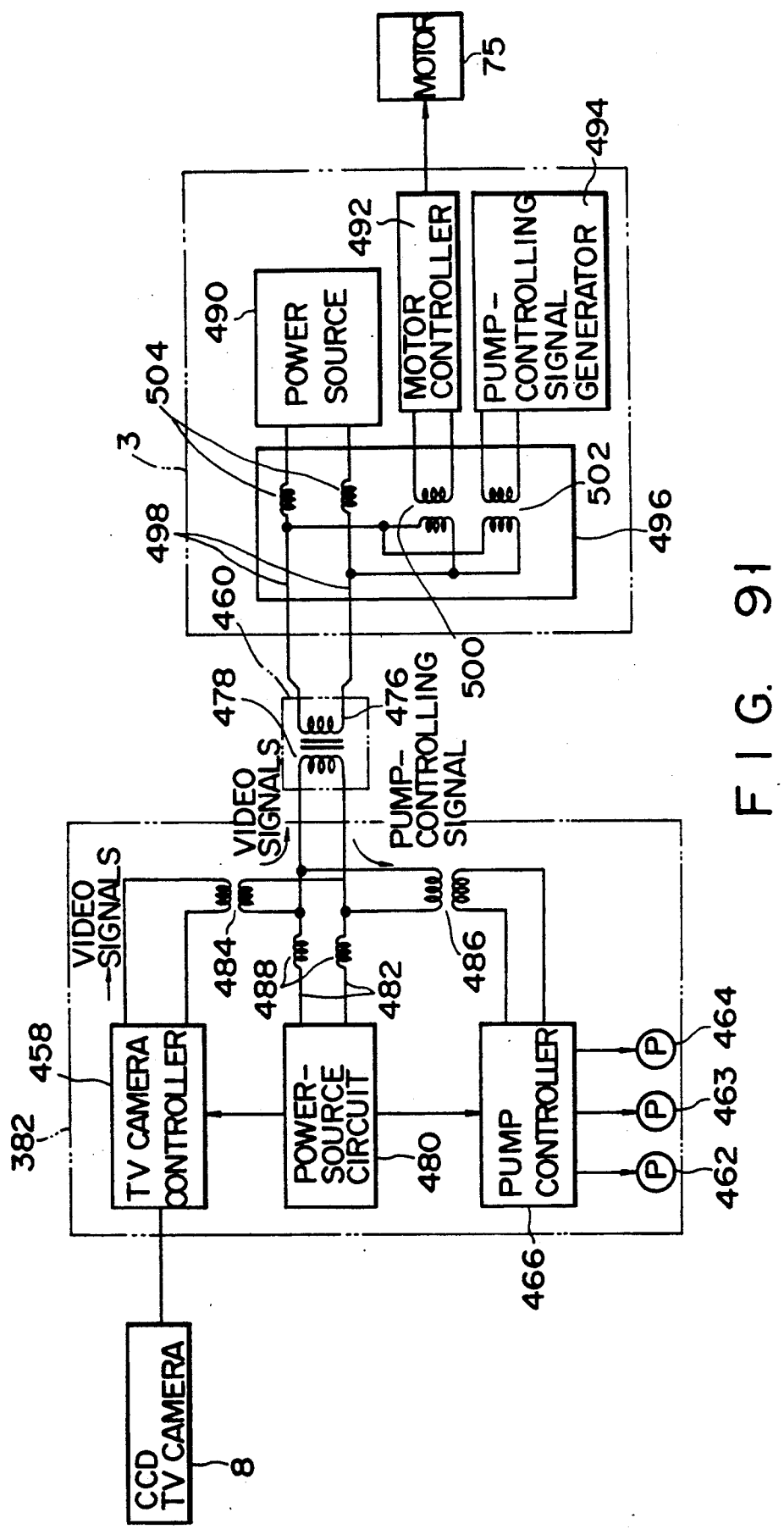
FIG. 91 is a block diagram showing the control circuit incorporated in the eleventh embodiment.

As is shown in FIG. 91, power-source circuit 480, which comprises a rectifier and a current-smoothing unit, is incorporated in drum 382. The input of circuit 480 is coupled to secondary coil 478 of rotary transformer 460. The output of circuit 480 is connected to TV camera controller 458 and also to pump controller 466, to supply power to these controllers 458 and 466. Fan 466 and light-source device 444 are connected to power-supply circuit 480, as is illustrated in FIG. 88. Power-supply circuit 480 is connected to secondary coil 478 by means of signal lines 482. The output of TV camera controller 458 is connected in parallel to this signal lines 482 by transformer 484. Similarly, the input of pump controller 466 is connected in parallel to this signal lines 482 by transformer 484. Hence, signal lines 482 can perform three functions: (i) to supply power to power-source circuit 480; (ii) to transfer video signals from TV camera controller 458; and (iii) to supply pump-controlling signals to pump controller 466. Further, as is shown in FIG. 91, two choke coils 488 are connected on signal lines 482 to select input signals to power-source circuit 480.

As is illustrated in FIG. 91, operation section 3 comprises power source 490, monitor controller 492, and pump-controlling signal generator 494. Power source 490 outputs a power signal having a frequency of, for example, of 20 KHz. Generator 494 generates a pump-controlling signal having a frequency, for example, 1 MHz. (The power signal output by power source 490 may be a 50 Hz signal which is commercially available.)

Power source 490, monitor controller 492, and pump-controlling signal generator 494 are connected to synthesizer 496 also incorporated in operation section 3. The output signal of synthesizer 496 is supplied to primary coil 476 of rotary transformer 460.

Synthesizer 496 comprises two transformers 500 and 502 connected in parallel to each other. Transformer 500 is connected between the input of monitor controller 492, on the one hand, and signal lines 498 connecting primary coil 476 and power source 490. Transformer 502 is connected between the output of pump-controlling signal generator 494, on the one hand, and signal lines 498, on the other hand. Therefore, synthesizer can combine electrical signals on signal lines 498, which have different frequencies. Choke coils 504 are provided on the signal lines of power source 490.

Transformer 486 and choke coils 488—all incorporated in drum 382—separate the output signal of synthesizer 496, to supply power to power-supply circuit 480 and pump-controlling signals to pump controller 466. TV camera controller 458 modulates the signals output by CCD 8 into video signals having a frequency different from that of the pump-controlling signals. These video signals are supplied to monitor controller 458 via transformer 500.

The operation of the pipe-inspecting apparatus according to the eleventh embodiment will now be explained. First, self-propelled section 2 is inserted into the tubular member which is to be inspected. Then, monitor controller 492 is operated to make section 2 move forward in the tubular member. Synthesizer 496 combines the power signal (20 KHz) supplied from power source 490 with the pump-controlling signal (1 MHz) supplied from pump-controlling signal generator 494, thereby generating an output signal. The output signal of synthesizer 496 is supplied to the electric circuit located in drum 382 through transformer 460. Choke coils 488 sample a drive current from the signal output by synthesizer 496. Power-source circuit 480 rectifies and smoothes the drive current. The current is then supplied to TV camera controller 458 and pump controller 466.

Transformer 486 extracts the pump-controlling signal from the output signal of synthesizer 496. The pump-controlling signal is supplied to pumps 462, 463, and 464 to control these pumps. In accordance with the signal, pumps 462, 463, and 464 supply and discharge air into and from elastic tube 20, front balloon 31, and rear balloon 32 of self-propelled section 2—all shown in FIG. 90. As a result, section 2 moves forward in the tubular member. More specifically, only front balloon 31 is inflated, whereby the distal end of section 2 is held in the tubular member. Next, air is supplied into tube 20, causing the tube to contract in its axial direction against the force of compression spring 28, whereby the rear end of section 2 moves forward, pulling cable 1 from drum 382 into the tubular member. Then, rear balloon 32 inflate is inflated, whereby the rear end of section 2 is held in the tubular member. Section 2 therefore takes an advanced position. Thereafter, front balloons 31 and tube 20 are deflated, whereupon the distal end of section 2 moves forward.

In the meantime, TV camera controller 458 drives CCD 8, and CCD 8 generates signals. TV camera controller 458 converts the signals into video signals which have a frequency higher than that of the pump-controlling signal. The video signals are supplied via transformer 484 to secondary coil 478 of rotary transformer 460. They are transferred to primary coil 476 and further to operation section 3. Transformer 500 separates the video signals from the other signals supplied through signal lines 498, and are input to monitor controller 492. Monitor controller 492 processes the video signals. The processed signals are supplied to TV monitor. TV monitor 75 displays an image of the interior of the tubular member, which is represented by the video signals.

After the tubular member has been inspected, operation section 3 is operated so as to make self-propelled section 2 move backward in the tubular member, thus pushing cable 1 out of the tubular member As cable 1 is pushed from the tubular member, drum 382 is rotated to take up cable 1.

As can be understood from the above, rotary transformer 460 is employed to transfer various signals between operation section 3 and the electric circuit located in drum 382. It has no pushes used as contracts, unlike the conventional rotary transformers. Hence, transformer 460 reliably transfers signals from section 3 to the electric circuit, or vice versa, whereas the conventional rotary transfer may fail to do so due to the wear of the contacts. Due to the use of rotary transformer 460, the pipe-inspecting apparatus according to the eleventh embodiment is sufficiently reliable. Also due to the use of rotary transformer 460, only two signal lines suffice to connect operation section 3 with the circuit arranged within drum 382.

Figure 92:
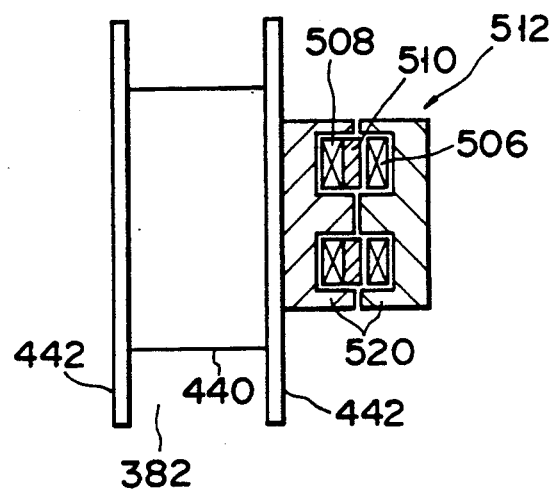
FIG. 92 is a vertical sectional view illustrating the rotary transformer incorporated in a first modification of the eleventh embodiment.

FIG. 92 shows a first modification of the eleventh embodiment. This modification is identical with the eleventh embodiment, except that rotary transformer 512 of a different type is used. As evident from FIG. 92, primary coil 506 and secondary coil 508 of transformer 512 are opposed, with insulator 510 interposed between them, whereas primary coil 476 and secondary coil 478 of transformer 460 are coaxial, one surrounding the other as is shown in FIG. 88.

Figure 93:
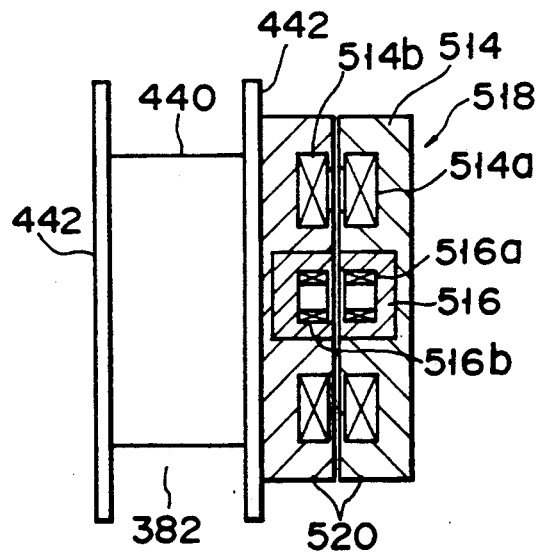
FIG. 93 is a vertical sectional view illustrating the rotary transformer incorporated in a second modification of the eleventh embodiment.

FIG. 93 illustrates a second modification of the eleventh embodiment. The second modification is identical with the eleventh embodiment, except that rotary transformer 518 of a different type is used. This transformer 518 comprises two cores 520 and two coil sections 514 and 516. Coil section 514 is designed to supply power, and coil section 516 is to transfer signals. More specifically, coil section 514 consists of primary coil 514a and secondary coil 514a both wound around first core 520, and coil section 514 is formed of primary coil 516b and secondary coil 516b both wound around second core 520. Since rotary transformer 518 has two coil sections, one for supplying power and the other for transferring signals, the power-supply line and the signal-supply line can be set apart from each other. Therefore, rotary transformer 518 has but a little switching noise.

Now, a twelfth embodiment of the present invention will be described, with reference to FIGS. 94, 95, and 96.

Figure 94:
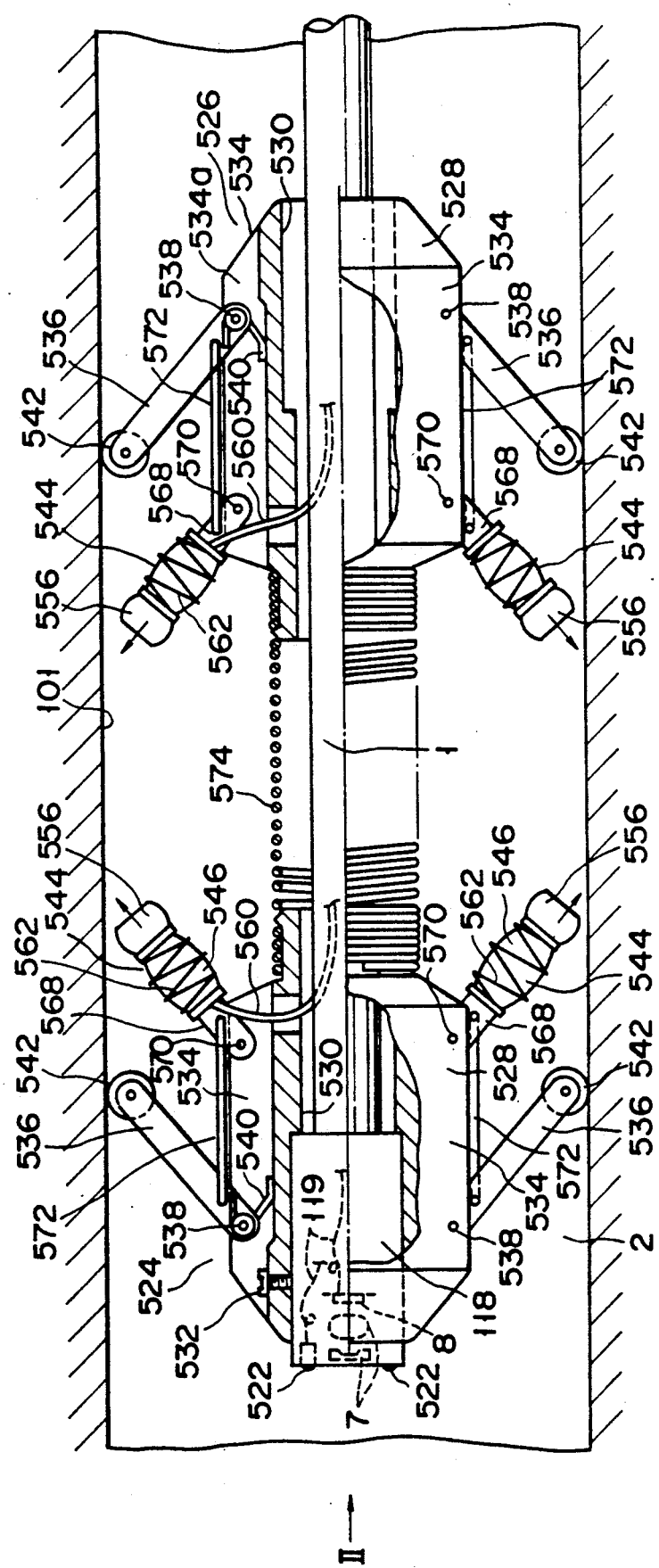
FIGS. 94 and 95 are a partially sectional side view and a front view, respectively, of the self-propelled unit incorporated in a pipe-inspecting apparatus according to a twelfth embodiment of the invention.
Figure 95:
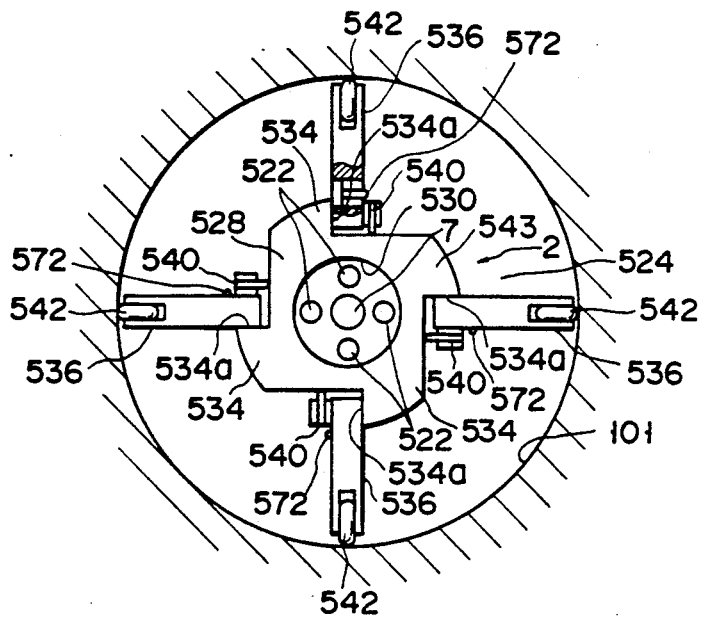

As is shown in FIG. 94, the pipe-inspecting apparatus according to the twelfth embodiment has flexible cable 1 and self-propelled section 2. Cable 1 is to be inserted into a tubular member to inspect the interior of the member. Section 2 is loosely mounted on the distal end portion of cable 1. Direct-view type TV camera 118 is attached to the distal end of cable 1. Lens 7, image-pickup element 8, illumination lamps 522, and the like are incorporated in the distal end of TV camera 118. Lens 7 is used to collect the light reflected from the inner surface of the tubular member.

Lines 119 connected to illumination lamps 522, image-pickup element 8, and the like extend through cable 1 and are coupled to a light-source device and a video processor (either not shown).

Self-propelled section 2 comprises front self-propelled mechanism 524 and rear self-propelled mechanism 536 which are spaced apart in the axial direction of cable 1. Mechanism 534 and 536 are identical in structure. The identical components of these mechanisms are denoted in FIG. 94 at the same reference numerals. Only front self-propelled mechanism 524 will now be described.

Front self-propelled mechanism 534 has cylindrical main body 528 which has through hole 530 coaxial with main body 528. Cable 1 passes through this hole 530. TV camera 118 is fitted in the front half of hole 530. Camera 118 is fastened to main body 528 by means of screw 532. Four supports 534 protrude from the circumferential surface of main body 528. These supports 534 extend parallel to the axis of main body 528. As is shown in FIG. 95, supports 534 are spaced at regular intervals along the circumference of body 58, as illustrated in FIG. 95. Four arms 536 are pivotally coupled to the sides 534a of supports 534 by means of pivots 538. As is shown in FIG. 95, arms extend in radial directions from main body 528. They are biased by means of torsion springs 540 to rotate toward the inner surface of tubular member 101. Four wheels 542 are rotatably connected to the tips of arms 536. These wheels 542 are in roll contact with the inner surface of tubular member 101, whereby main body 528 and cable 1 are positioned coaxially with tubular member 101.

Four actuators 544 are fastened to the sides 534a of supports 534 and located behind arms 536. These actuators 544 are designed to push the inner surface of tubular member 101, to apply a thrust to self-propelled mechanism 524. They are of the same structure, and only one of them will be described with reference to FIG. 96.

Figure 96:
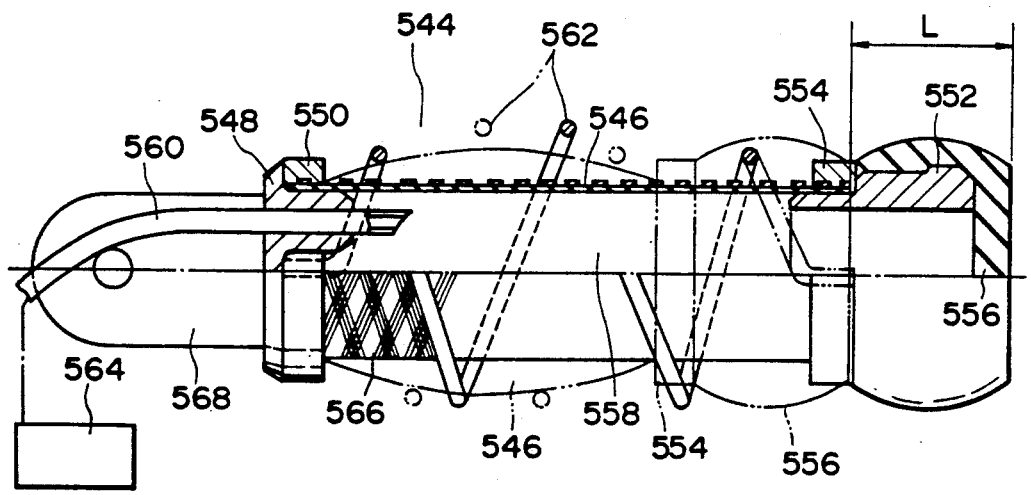
FIG. 96 is a partially sectional side view showing an actuator made of rubber, which is used in the twelfth embodiment.

As is illustrated in FIG. 96, each actuator 544 comprises rubber tube 546 which can expand in its axial direction. One end of tube 546 is mounted on the circumferential surface of end member 548, and is fastened thereto by fastening ring 550. Similarly, the other end of tube 546 is mounted on the circumferential surface of one end portion of cylindrical member 552, and is fastened thereto by fastening ring 554. Hence, both ends of rubber tube 546 are closed in airtight fashion. The other end portion of cylindrical member 552 is covered with rubber cap 556. Cap 556 also covers the open end of cylindrical member 552. Hence, both ends of rubber tube 546 are closed in airtight fashion, and closed chamber 558 is defined by rubber tube 546, end member 548, cylindrical member 552, and rubber cap 556. Air-supporting tube 560 extends into this chamber 558 through the hole made in end member 548. This tube 564 (e.g., an air pump). Compressed air can be supplied into chamber 558 and is charged therefrom, through air-supplying tube 560.

Barrel-shaped coil spring 562 is wound around rubber tube 546. This spring is held between fastening rings 550 and 554, and is hence compressed, biasing rubber tube 546 to expand in the axial direction.

Sleeve 566, which is made of a net formed of filaments, is wrapped around rubber tube 546. Sleeve 566 is designed to allow rubber tube 546 to expand in the radial direction and take a barrel shaped (indicated by the two-dot, one-dash lines) when compressed air is supplied from compressor 564 into chamber 558. When tube 546 expands in its radial direction, it contracts by distance L in its axial direction.

Bracket 568 projects from end member 548 in the axial direction of rubber tube 546. Bracket 568 is pivotally coupled to the side 534a of support 534. Connecting rod 572 is connected at one end to arm 536 and at the other end to bracket 568. The bias of torsion spring 540 is applied to rubber actuator 544. Rubber actuator 544 is, therefore, biased to rotate in the same direction as arm 536, and is inclined backward.

As is shown in FIG. 94, arms 536 and rubber actuators 544 of rear self-propelled mechanism 526 are inclined forward. Front self-propelled mechanism 524 and rear self-propelled mechanism 526 are connected by coil spring 574, so that they can moved toward or away from each other.

It will now be explained how self-propelled section 2 moves forward in tubular member 101. First, compressed air is supplied from compressor 564 into rubber actuators 544 of both self-propelled mechanisms 524 and 526, thereby raising the pressure within closed chambers 558 of mechanisms 524 and 526. Rubber tubes 545 expand in their radial direction and shaped like a barrel as is indicated by the two-dot, one-dash lines in FIG. 96. Rubber tubes 546 contract by distance L in their axial direction. As a result of this, caps 556 connected to rubber tubes 546 leave the inner surface of tubular member 101.

Then, the compressed air is discharged from the rubber actuators 544 of front self-propelled mechanism 524 through air-supplying tubes 560. These rubber tubes 546 quickly extend in their axial direction for N distance L due to the force of coil springs 562. Caps 556 of actuators 546 push the inner surface of tubular member 101 backwards. As a result, self-propelled section 2 moves forward for distance L.

Thereafter, compressed air is supplied into actuators 544 of front self-propelled mechanism 254, thereby causing tube 544 to contract in its axial direction. Hence, caps 556 are moved away from the inner surface of tubular member 101. Then, air is discharged from closed chamber 558, thereby elongating tube 546. This time, caps 556 push the inner surface of member 101, whereby self-propelled section 2 moves forward by distance L.

As compressed air is repeatedly supplied into, and discharged from, actuators 544 in the manner described above, actuators 544 repeatedly contract and expand in their axial direction. The force resulting from the repeated expansion of actuators 544 is used as a thrust for moving section 2 forward in tubular member 101.

In order to move self-propelled section 2 backward, it suffices to keep actuators 544 of front self-propelled mechanism 524 inflated at all times, and to inflate and deflate actuators 544 of rear self-propelled mechanism 526 repeatedly. In this case, the force resulting from the repeated expansion of actuators 544 is used as a thrust for moving section 2 backward in tubular member 101.

Whichever self-propelled mechanism, mechanism 524 or 526, is operated as described above to move section 2 either forward or backward in tubular member 101, four actuators 544 repeatedly expand in their axial direction, thus pushing the inner surface of tubular member 101 and repeatedly contract to move away from the inner surface of member 101. The thrust resulting from the expansions of actuators 544 is great enough to move section 2 forward or backward reliably in tubular member 101.

With the twelfth embodiment it suffices to supply compressed air into four actuators 544 simultaneously, and to discharge it from actuators 544 also simultaneously. Hence, no complex control systems are required to control the timing of supplying and discharging air into and from each actuator.

As has been discussed, it is easy to generate the thrust for moving section 2 forward or backward, and the structure of the apparatus according to the twelfth embodiment is simple in structure. The apparatus is, therefore, sufficiently reliable.

Compressed air is used in the twelfth embodiment to operate actuators 544. Instead, a liquid such as oil can be used for the same purpose. Further, actuators 544 can be used in less numbers; one actuator need not be provided for each arm 536. For instance, only one actuator 544 is sufficient for each self-propelled mechanism.

Now, a thirteenth embodiment of the invention will be described with reference to FIGS. 97 and 98.

Figure 97:
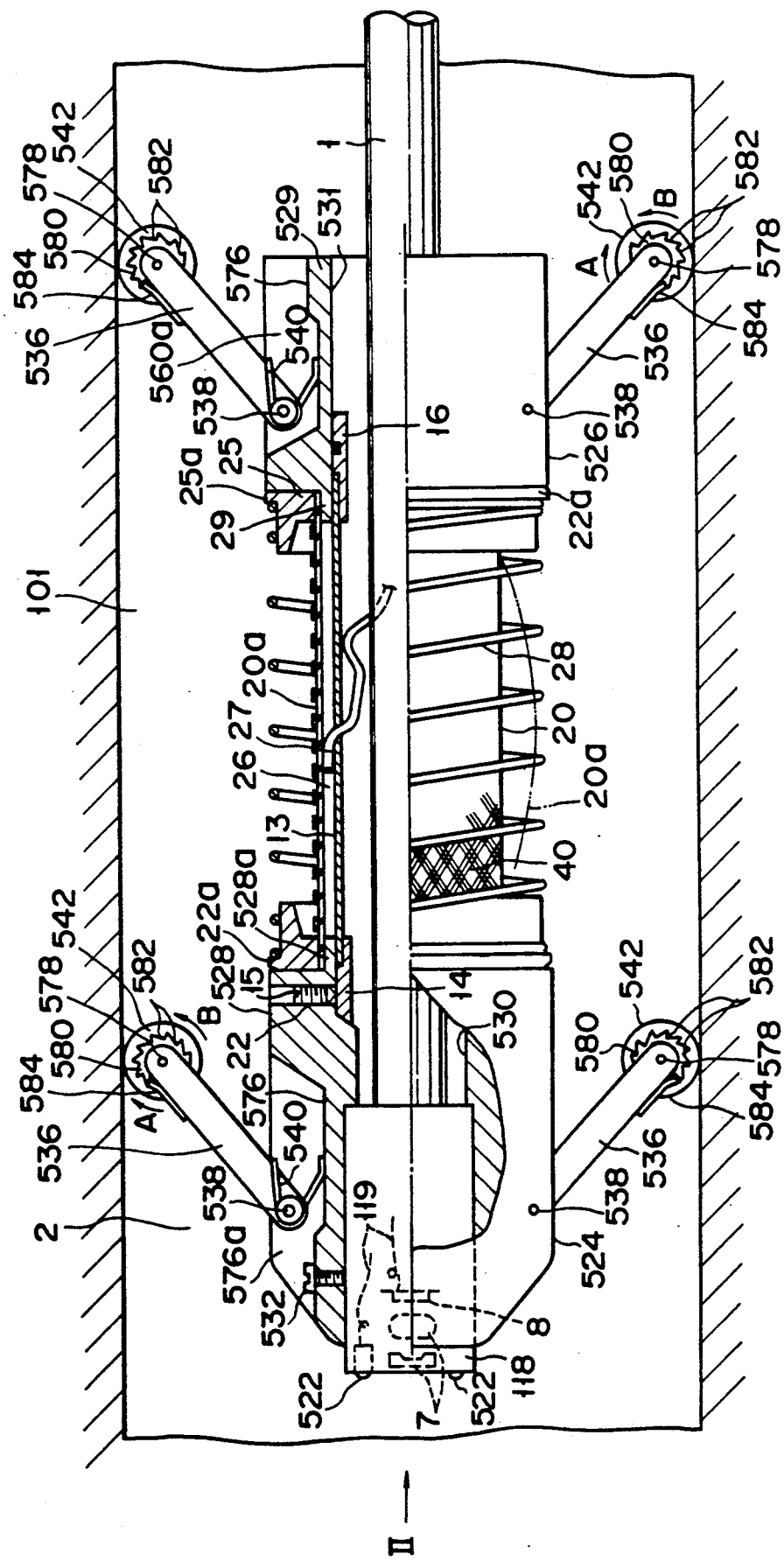
FIGS. 97 and 98 are a partially sectional side view and a front view, respectively, of the self-propelled unit incorporated in a pipe-inspecting apparatus according to a thirteenth embodiment of the invention.
Figure 98:
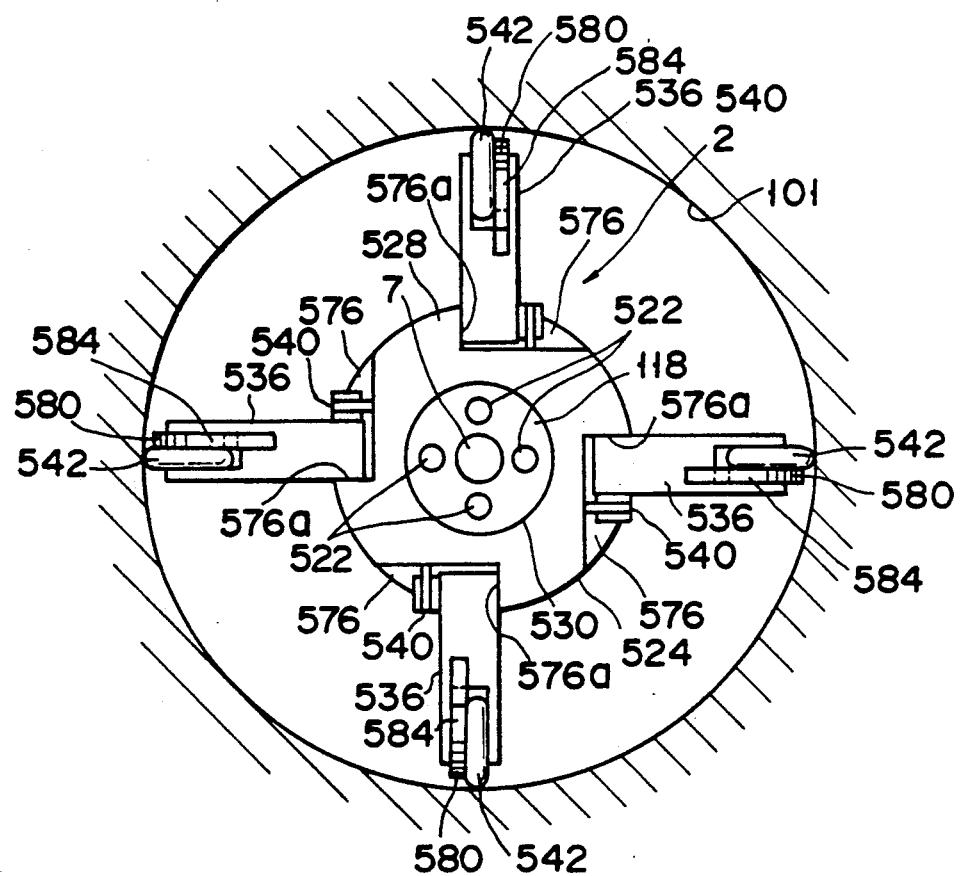

As is shown in FIG. 97, the pipe-inspecting apparatus according to the thirteenth embodiment has flexible cable 1 and self-propelled section 2. Cable 1 is to be inserted into a tubular member to inspect the interior of this member. Unit 2 is loosely mounted on the distal end portion of cable 1 Direct-view type TV camera 118 is attached to the distal end of cable 1. Lens 7, image-pickup element 8, illumination lamps 522, and the like are incorporated in the distal end of TV camera 118. Lens 7 is used to collect the light reflected from the inner surface of the tubular member.

Self-propelled section 2 comprises front self-propelled guide unit 524 and rear self-propelled guide unit 256 which are spaced apart in the axial direction of cable 1. Units 524 and 526 have cylindrical main bodies 528 and 529, respectively. Main bodies 528 and 529 have through holes 530 and 531 in which the distal end portion of cable 1 inserted TV camera 118 is fitted in the front half of hole 530 of main body 528. Camera 118 is fastened to main body 528 by means of screw 532.

Front guide unit 524 and rear guide unit 526 are connected by inner tube 13. More specifically, connector tube 14 is attached to front end of tube 13. Connector tube 14 fitted in the hole 530, together with the front end portion of inner tube 13. Both tube 14 and the front end portion of tube 13 are fastened to main body 528 by means of screw 15, so that they are not slipped out of main body 628. Sliding tube 16 is attached to the rear end of inner tube 13. This tube 16 is slidably inserted in the hole 531 of main body 529, along with the rear end portion of inner tube 13. Hence, front self-propelled unit 524 and rear self-propelled unit 526 can move toward and away from each other, in the axial direction of inner tube 13. Cable 1 extends through inner tube 13.

Actuator 20, which is a hollow cylinder, is mounted on inner tube 13 and interposed between front guide unit 524 and rear guide unit 526. Actuator 20 is used to generate force to propel both guide units 524 and 526. Actuator 20 comprises rubber tube 20a having a circular cross section. The front end of tube 20a is mounted on cylinder 528a projecting from the rear end of main body 528, and the rear end of tube 20a is mounted on cylinder 529a projecting from the rear end of main body 529. Fastening rings 22 and 25 is wrapped around the ends of rubber tube 20a, thus fastening these ends to cylinders 528a and 529a. Rubber tube 20a is arranged coaxial with inner tube 13, surrounding tube 13. Closed chamber 26 is formed between inner tube 13 and rubber tube 20a. Air-supplying tube 27 is connected to closed chamber 26 at one end. Air-supplying tube 27 extends through inner tube 13 and cable 1 is connected, at the other end, to an air compressor (not shown) such as an air pump. Compressed air can therefore be supplied into chamber 26 and discharged therefrom, through air-supplying tube 27.

Coil spring 28 is wound around rubber tube 20a. Coil spring 28 is interposed between spring seats 22a and 25a which are integrally formed with fastening rings 22 and 25, respectively. Therefore, spring 28 causes rubber tube 20a to elongate. Sleeve 40, which is made of net formed of filaments, is wrapped around rubber tube 20a. Sleeve 40 is designed to allow tube 20a to expand in the radial direction and take a barrel shape (indicated by the two-dot, one-dash lines) when compressed air is from the compressor into chamber 26. When tube 20a expands in its radial direction, it contracts in its axial direction.

Four recesses 576 are made in the circumferential surface of either main body. As is shown in FIG. 98, these recesses 576 are spaced at regular intervals along the circumference of the main body. Four arms 536 are pivotally coupled, at one end, to sides 576a of recesses 576 by means of pivots 538. These arms 536 extend in radial directions from the main body. Arms 536 can rotate about pivots 538, to contact the inner surface of tubular member 101 and move away therefrom. Arms 536 are biased by torsion springs 540 to rotated toward the inner surface tubular member. Four wheels 542 are rotatably connected to the tips of arms 536. Wheels 542 are in roll contact with the inner surface of member 101, whereby the main body and cable 1 are positioned coaxially with tubular member 101. A ratchet mechanism is attached to each wheel 542, respectively, to allow the wheel to rotate in one direction only.

As actuator 20 repeatedly expands and contracts in its axial direction, it exerts a force moving self-propelled section 2 forward in tubular member 101. As section 2 moves forward, wheels 542, which, contact the inner surface of member 101, rotate. Hence, the friction between section 2 and the inner surface of member 101 is small. When a backward force is applied to section 2, the ratchet mechanisms prevent wheels 542 from rotating, thus increasing the friction between self-propelled section 2 and the inner surface of tubular member 101. As a result, section 2 can move forward more easily than backward in tubular member 101, as actuator 20 repeatedly expands and contracts in its axial direction.

The operation of the thirteenth embodiment will now be explained.

In order to move self-propelled section 2 forward in tubular member 101, compressed air is supplied from the air compressor into closed chamber 26 defined by actuator 20, thus raising the pressure within chamber 26. Rubber tube 20a expands in its radial direction and contracts in its axial direction. Coil spring 28 is therefore compressed, and rear self-propelled guide unit 526 is pulled toward front self-propelled guide unit 524 by the distance the tube 20a contracts in the axial direction. On the other hand, front guide unit 524 scarcely moves forward or backward. This is because the ratchet mechanisms of rear guide unit 526 allow wheels 542 to rotate clockwise, whereas unit 524 scarcely moves backward though a backward pull is applied to it. Front self-propelled guide unit 524 moves little since its ratchet mechanisms prevent wheels 542 from rotating, that is, pawls 584 of the ratchet mechanisms lock ratchet wheels 580 the moment wheels 542 begin to rotate counterclockwise (FIG. 97).

Thereafter, the air is discharged from closed chamber 26, whereby coil spring 28 expands to its original length. Rubber tube 20a expands forthwith, in its axial direction, thus exerting a forward pull on front self-propelled guide unit 524, and exerting a backward pull on rear self-propelled guide unit 526. In this case, front guide unit 524 moves forward by the distance tube 20a has expanded in the axial direction, since its ratchet mechanisms allow wheel 542 to rotate clockwise, that is, no pawls 584 lock ratchet wheels 580. On the other hand, rear self-propelled guide unit 526 moves backward only a little despite the backward pull, since its ratchet mechanisms prevent wheels 542 from rotating, that is, pawls 584 of the ratchet mechanisms lock ratchet wheels 580 the moment wheels 542 begin to rotate counterclockwise (FIG. 97).

Hence, as compressed air is repeatedly supplied into, and discharged from, actuator 20, self-propelled section 2 intermittently moves forward in tubular member 101.

In the case of the thirteenth embodiment, it is only actuator 20 which must be repeatedly inflated and deflated, in order to move self-propelled section 2 in tubular member 101, and actuator 20 is quickly inflated and deflated. Therefore, section 2 can move in member 101 at a comparatively high speed.

In addition, it suffices to supply compressed air into and discharge it from only one component, i.e., actuator 20, no complex control systems are required to control the timing of supplying or discharging air into and from actuator 20. The apparatus according to the thirteenth embodiment is simple in structure and can be made at low cost.

As is evident from the above, the apparatus of the thirteenth embodiment has a simple structure, and can easily generate a force for moving section 2 forward. Hence, the apparatus is sufficiently reliable.

Further, since arms 536, which hold section 2 in tubular member 101, are biased by torsion springs 540 to contact the inner surface of member 101, they more readily contact the inner surface of member 101 than the balloons used in the other embodiments described above. In other words, arms 536 can rotate very fast in either direction as section 2 moves forward in tubular member 101 which has a varying inside diameter. Since arms 536 can quickly rotate in either direction, self-propelled section 2 can be inserted into tubular members having various inside diameters, and can move forward in these members.

Figure 99:
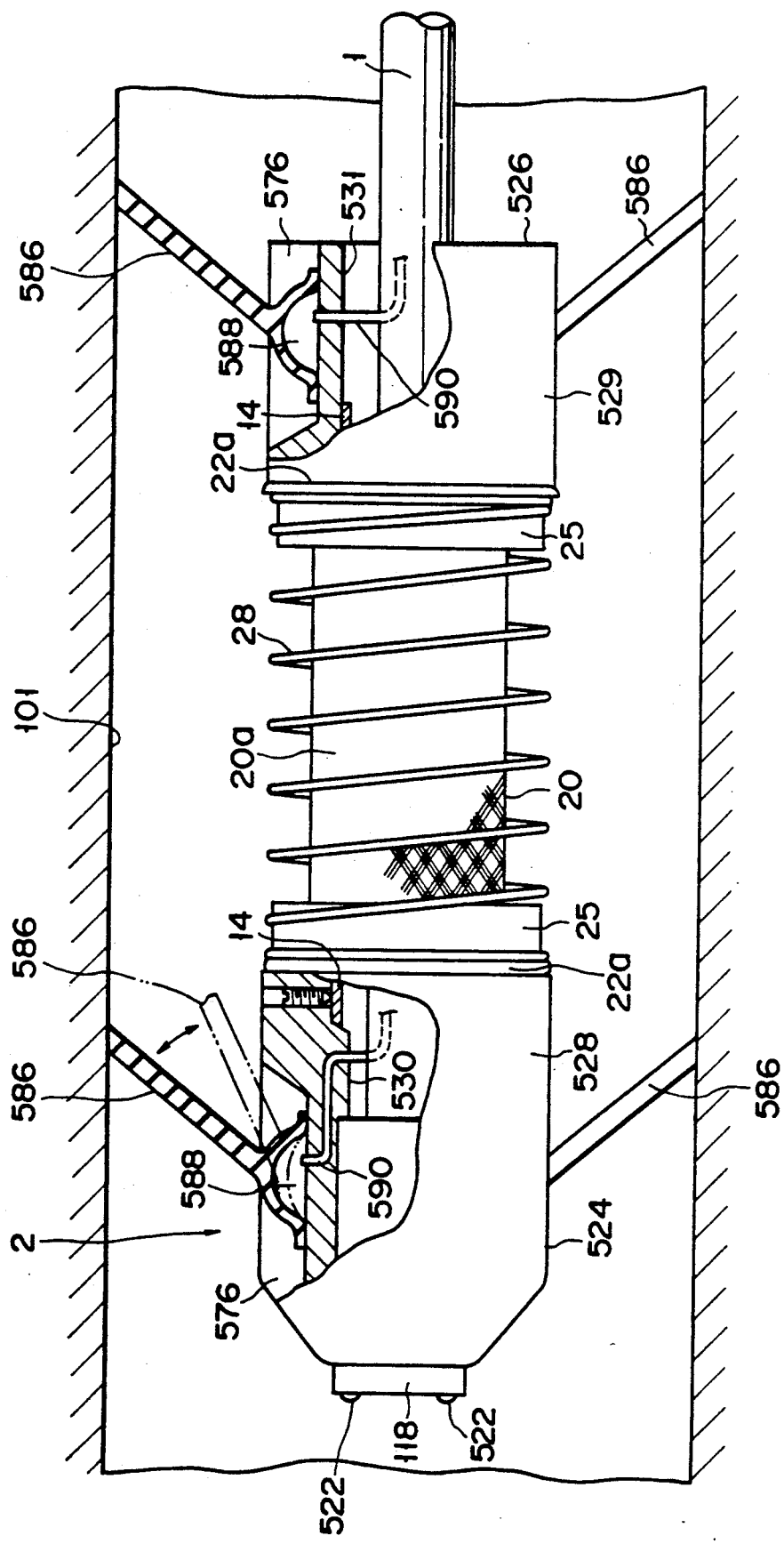
FIG. 99 is a partially sectional side view showing the self-propelled unit incorporated in a modification of the thirteenth embodiment.

FIG. 99 illustrates a modification of the thirteenth embodiment of the present invention. As is shown in this figure, arms 586 of either self-propelled guide unit (524 or 526) are made of elastic material such as rubber or a synthetic resin. Each arm 586 is pivotally connected, at one end, to recess 576 made in the circumferential surface of the main body (528 or 529) of the guide unit. The proximal end of each arm 586 is shaped like a cup and defines pressure chamber 588. Air-supplying tube 590 is connected to this chamber 588. Tubes 590 connected to chambers 588 extend through main bodies 528 and 529 and also through cable 1, and communicate with an air compressor (not shown). Hence, compressed air can be supplied and discharged through tubes 590, into and from pressure chambers 588.

When no compressed air is supplied into pressure chambers 588, arms 586 are tilted downward and rearward, with their tips out of contact with the inner surface of tubular member 101, as is shown by the two-dot, one-dash lines. When compressed air is supplied into chambers 588, arms 586 are held upward until their tips contact the inner surface of tubular member 101, while remaining inclined rearwards. Thus, pressure chambers 588 function as means for biasing arms 586.

As has been described, arms 586 remain inclined rearward when they are in their held-up positions, as well as when they are in their lower positions. Hence, when either guide unit is pushed forward in tubular member 101, its arms 586 incline rearward a little, whereby the friction between the tips of arms 586 and the inner surface of member 101 decreases. As a result, the guide unit can move forward smoothly in tubular member 101. On the other hand, when either guide unit is pushed backward in member 101, its arms 586 are held up a little, pushing the inner surface of member 101, whereby the friction between the tips of arms 586 and the inner surface of member 101 increases. Consequently, the guide unit cannot move backward in tubular member 101.

Therefore, as compressed air is repeatedly supplied into and discharged from actuator 20, thus repeatedly expanding and contracting tube 20 in its axial direction, self-propelled section 2 intermittently move forward in tubular member 101.

When air is discharged from all pressure chambers 588, arms 586 of both guide units 524 and 526 are tilted down away from the inner surface of tubular member 101, self-propelled section 2 can be smoothly pulled backward through tubular member 101.

Compressed air is used in the thirteenth embodiment to operate actuator 20 and also to tilt arms 586 upward and downward. Instead, a liquid such as oil can be used for the same purpose.

What is claimed is:

1. A pipe-inspecting apparatus comprising:
   (a) a self-propelled unit including:
   an elastic driving unit having an elastic tube, and restriction means mounted on the outer surface of said elastic tube for restricting a longitudinal expansion of said elastic tube, and
   balloons, located at front and rear ends of said elastic driving unit, which are capable of expanding and contracting in a radial direction of said elastic tube; and
   (b) an observation means having an elongated insertion portion which is moved in and through a pipe by said self-propelled unit;
   wherein said self-propelled unit has a through hole elongated along the central axis thereof, into which the insertion portion of said observation means is inserted, and the insertion portion is connected to the self propelled unit.

2. The pipe-inspecting apparatus according to claim 1, wherein said balloon is detachably coupled to said elastic tube.

3. The pipe-inspecting apparatus according to claim 1, wherein said first and second holding means have a plurality of balloons each, which have different outside diameters.

4. The pipe-inspecting apparatus according to claim 1, wherein at least one of said holding means has a plurality of balloons spaced apart in a circumferential direction of said elastic tube.

5. The pipe-inspecting apparatus according to claim 1, wherein said self-propelled unit further includes a connector detachably connected to the apparatus.

6. The pipe-inspecting apparatus according to claim 1, further comprising inclination-restricting means located near at least said first holding means, for restricting the inclination of a distal end portion of said self-propelled unit.

7. The pipe-inspecting apparatus according to claim 1, wherein said fluid control means has fluid passage means communicating with said elastic tube and said first and second holding means, and a fluid supplying-/discharging unit for supplying the fluid into, and discharging the fluid from, said elastic tube and said first and second holding means.

8. The pipe-inspecting apparatus according to claim 7, wherein said fluid passage means comprises a main tube extending from said fluid supplying/discharging unit and three branch tubes branching from the main tube and communicating with said elastic tube, said first holding means, and said second holding means, respectively.

9. The pipe-inspecting apparatus according to claim 1, wherein said observation means has a flaw detecting sensor by eddy-current.

10. The pipe-inspecting apparatus according to claim 1, wherein said observation means has an ultrasonic sensor.

11. The pipe-inspecting apparatus according to claim 1, wherein said restriction means has a plurality of wires arranged in parallel to one another.

12. A pipe-inspecting apparatus according to claim 1, wherein a tip end of the insertion portion of said observation means is fixed in a distal portion of said self-propelled unit.

13. A pipe-inspecting apparatus according to claim 1, wherein said self-propelled unit has a main body, for holding the front balloon and said elastic driving unit, and a fixing ring, one end of said front balloon being sandwiched between the fixing ring and the main body.

14. A pipe-inspecting apparatus according to claim 13, wherein said self-propelled unit has a screw means for fixing a distal end portion of the insertion portion of said observation means, said screw means being engaged with a front of said fixing ring in said main body and having a head projecting from an outer surface of the main body.

15. A pipe-inspecting apparatus according to claim 1, wherein said self-propelled unit has a main body, for holding the front balloon, another hollow main body for holding the rear balloon, and an electric tube provided between both main bodies, said elastic driving unit is arranged on the outer surface of said elastic tube, and an air-tight space where a fluid is selectively supplied to or discharged from is defined by said driving unit, elastic tube, and both main bodies.

16. A pipe-inspecting apparatus according to claim 15, further comprising:
   a fluid path tube connected to said front balloon, wherein the fluid path and the insertion portion of said observation means are inserted in said elastic tube.

17. A pipe-inspecting apparatus according to claim 16, wherein said fluid path tube is loosely arranged in said elastic tube.

18. A pipe-inspecting apparatus according to claim 1, wherein said self-propelled unit includes a main body for holding a balloon, and fixing means for fixing the held balloon, said fixing means having an O-ring and a fixing ring, and said fixing ring is fixed to an end of said main body so as to fasten the outer periphery of the insertion portion of the observation means, with pressing and deforming said O-ring.

19. A pipe-inspecting apparatus according to claim 1, wherein the insertion portion of said observation means is arranged approximately coaxially with said self-propelled unit.

20. A pipe-inspecting apparatus according to claim 1, further comprising urging means for urging said elastic tube to expand in the longitudinal direction thereof.

21. A pipe-inspecting apparatus according to claim 20, wherein said bias means comprises a spring.

22. A pipe-inspecting apparatus according to claim 1, further comprising:
display means for displaying an image;
and wherein said observation means comprises:
imaging means for converting an image into an electrical signal;
signal transmitting means for transmitting a signal from said imaging means to said display means; and
connector means for electrically connecting said observation means to said display means.

23. The pipe-inspecting apparatus according to claim 22, wherein said observation means has a signal-transmitting means connected to said display means by an electrical connector, for transmitting signals representing the image of the interior of the pipe to said display means, said fluid passage means is connected to said fluid control means by a fluid connector, and said electrical connector and said fluid connector are formed integrally with each other.

24. A pipe-inspecting apparatus according to claim 1, wherein said observation means includes a bore scope.

25. A pipe-inspecting apparatus according to claim 1, further comprising:
display means for displaying an image of the interior of the pipe, which has been scanned by said observation means;
fluid control means for supplying fluid into said elastic tube and said balloons, and for discharging the fluid from said elastic tube and said balloons;
a cable connecting said observation means with said display means, and connecting said elastic tube and said balloons with said fluid control means; and
a drum unit provided at a proximal portion of said cable and around which said cable is rolled.

26. A pipe-inspecting apparatus according to claim 25, wherein:
said cable comprises a first portion having a first fluid passage communicating with said elastic tube and said balloons, and a second portion having a second fluid passage communicating with said fluid control means; and
said drum unit comprises drum means including a shaft, for taking up said first portion of said cable, and a rotary connector mounted on the shaft of the drum means, and connecting said first and second passages, while allowing said first and second fluid passages to rotate relative to each other.

27. A pipe-inspecting apparatus according to claim 25, wherein:
said cable comprises a first portion having a first signal-transmitting member connected to said self-propelled unit, and a second portion having a second signal-transmitting member connected to said fluid control means; and
said drum unit comprises drum means including a shaft for taking up the first portion of said cable, and a rotary transformer arranged coaxially with the shaft of said drum means, and connecting said first and second signal-transmitting members, while allowing said first and second signal-transmitting members to rotate relative to each other.

28. A pipe-inspecting apparatus according to claim 1, further comprising:
another self-propelled unit connected to said first-mentioned self-propelled unit in series.

29. A pipe-inspecting apparatus according to claim 28, further comprising:
control apparatus for individually controlling said self-propelled units.

30. A pipe-inspecting apparatus according to claim 29, wherein:
said control means includes fluid control means for supplying fluid into said self-propelled units and for exhausting the fluid out of said self-propelled units, thereby moving said self-propelled units; and
said fluid control means includes a fluid control section for contracting at least balloons of one of said self-propelled units, and for supplying fluid into the other of said self-propelled units and exhausting the fluid out of the other of said self-propelled units.

31. A pipe-inspecting apparatus comprising:
(a) a self-propelled unit including:
an elastic driving unit having an elastic tube, and a restriction means mounted on the outer surface of said elastic tube for restricting a longitudinal expansion of said elastic tube, and
balloons, located at front and rear ends of said elastic driving unit, which are capable of expanding and contracting in a radial direction of said elastic tube; and
(b) observation means having an elongated insertion portion which is moved in and through a pipe by said self-propelled unit;
wherein a tip end of the insertion portion of said observation means is connected to said self-propelled unit by connecting means with a predetermined distance provided between said tip end of the insertion portion and said self-propelled unit.

32. A pipe-inspecting apparatus according to claim 31, further comprising:
fluid path tubes for supplying fluid to each of said elastic driving unit and the front and rear balloons, wherein said fluid path tubes are bundled.

33. A pipe-inspecting apparatus according to claim 31, wherein said connecting means has at least one wire connecting said self-propelled unit and observation means.

34. A pipe-inspecting apparatus according to claim 33, further comprising:
a removable adapter mounted on the tip of the insertion portion of said observation means, wherein one end of said wire is connected to the adapter.

35. A pipe-inspecting apparatus according to claim 33, wherein one end of said wire is connected to a rear end of said self-propelled unit.

36. A pipe-inspecting apparatus according to claim 31, wherein said connecting means has a plurality of wires connecting said self-propelled unit observation means, the wires being arranged so as to be inclined with respect to the longitudinal axis of said self-propelled unit.

37. A pipe-inspecting apparatus according to claim 31, further comprising:

display means for displaying an image of the interior of the pipe, which has been scanned by said observation means;

fluid control means for supplying fluid into said elastic tube and said balloons, and for discharging the fluid from said elastic tube and said balloons;

a cable connecting said observation means with said display means, and connecting said elastic tube and said balloons with said fluid control means; and a drum unit provided at a proximal portion of said cable and around which said cable is rolled.

38. A pipe-inspecting apparatus according to claim 37, wherein:

said cable comprises a first portion having a first fluid passage communicating with said elastic tube and said balloons, and a second portion having a second fluid passage communicating with said fluid control means; and said drum unit comprises drum means including a shaft for taking up said first portion of said cable, and a rotary connector mounted on the shaft of the drum means, and connecting said first and second passages, while allowing said first and second fluid passages to rotate relative to each other.

39. A pipe-inspecting apparatus according to claim 37, wherein:

said cable comprises a first portion having a first signal-transmitting member connected to said self-propelled unit, and a second portion having a second signal-transmitting member connecting to said fluid control means; and said drum unit comprises drum means including a shaft for taking up the first portion of said cable, and a rotary transformer arranged coaxially with the shaft of said drum means, and connecting said first and second signal-transmitting members, while allowing said first and second signal-transmitting members to rotate relative to each other.

40. A pipe-inspecting apparatus according to claim 31, further comprising:

another self-propelled unit connected to said first-mentioned self-propelled unit in series.

41. A pipe-inspecting apparatus according to claim 40, further comprising:

control means for individually controlling said self-propelled units.

42. A pipe-inspecting apparatus according to claim 41, wherein:

said control means includes fluid control means for supplying fluid into said self-propelled units and for exhausting the fluid out of said self-propelled units, thereby moving said self-propelled units; and said fluid control means includes a fluid control section for contracting at least balloons of one of said self-propelled units, and for supplying fluid into the other of said self-propelled units and exhausting the fluid out of the other of said self-propelled units.

43. A pipe-inspecting apparatus comprising:

an observation means having an elongated insertion portion and a self-propelled unit including a pair of annular bodies into which the insertion portion of said observation means is inserted, said insertion portion being fixed to one of said annular bodies, and being slidably connected to the other one of said annular bodies;

a plurality of elastic driving units, located around said insertion portion of said observation means, and arranged between said pair of annular units; and fixing means provided on said pair of annular bodies, saif fixing means having a balloon capable of selectively expanding or contracting in a radial direction of said insertion portion.

44. A pipe-inspecting apparatus according to claim 43, further comprising:

control means for individually controlling said plurality of elastic driving units.

45. A pipe-inspecting apparatus according to claim 44, wherein the section of said insertion portion located between said pair of annular bodies has flexibility.

46. A pipe-inspecting apparatus according to claim 43, further comprising:

fluid path tubes connected to said balloons and to said elastic driving unit, at least one of said fluid path tubes arranged in the insertion portion of said observation means via a fixing portion of one annular unit and said observation means.

47. A pipe-inspecting apparatus according to claim 43, further comprising:

urging means, arranged between said pair of annular units, for urging said elastic driving unit in an elongating direction.

48. A pipe-inspecting apparatus according to claim 47, wherein said urging means is provided on the outer periphery of the insertion portion of said observation means.

49. A pipe-inspecting apparatus according to claim 47, wherein said urging means is provided coaxially with the insertion portion of said observation means.

50. A pipe-inspecting apparatus according to claim 43, further comprising:

display means for displaying an image of the interior of the pipe, which has been scanned by said observation means;

fluid control means for supplying fluid into said elastic driving units and said balloons, and for discharging the fluid from said elastic driving units and said balloons;

a cable connecting said observation means with said display means, and connecting said elastic driving units and said balloons with said fluid control means; and a drum unit provided at a proximal portion of said cable and around which said cable is rolled.

51. A pipe-inspecting apparatus according to claim 50, wherein:

said cable comprises a first portion having a first fluid passage communicating with said elastic driving units and said balloons, and a second portion having a second fluid passage communicating with said fluid control means; and said drum unit comprises drum means including a shaft for taking up said first portion of said cable, and a rotary connector mounted on the shaft of the drum means, and connecting said first and second passages, while allowing said first and second fluid passages to rotate relative to each other.

52. A pipe-inspecting apparatus according to claim 50, wherein:

said cable comprises a first portion having a first signal-transmitting member connected to said self-propelled unit, and a second portion having a second signal-transmitting member connected to said fluid control means; and said drum unit comprises drum means including a shaft for taking up the first portion of said cable, and a rotary transformer arranged coaxially with the shaft of said drum means, and connecting said first and second signal-transmitting members, while allowing said first and second signal-transmitting members to rotate relative to each other.

53. A pipe-inspecting apparatus according to claim 43, further comprising:

another self-propelled unit connected to said first-mentioned self-propelled unit in series.

54. A pipe-inspecting apparatus according to claim 53, further comprising:

control means for individually controlling said self-propelled units.

55. A pipe-inspecting apparatus according to claim 54, wherein:

said control means includes fluid control means for supplying into said self-propelled units and for exhausting the fluid out of said self-propelled units, thereby moving said self-propelled units; and said fluid control means includes a fluid control section for contracting at least balloons of one of said self-propelled units, and for supplying fluid into the other of said self-propelled units and exhausting the fluid out of the other of said self-propelled units.

56. A pipe-inspecting apparatus comprising:

(a) a plurality of self-propelled units, each unit including:

an elastic driving unit including an elastic tube, and restricting means mounted on the outer surface of said elastic tube for restricting a longitudinal expansion of said elastic tube, and balloons located on opposite ends of said elastic driving unit and being expandable and contractible in a radial direction thereof;

(b) a driven unit connected to one of said self-propelled units and driven by the same;

(c) fluid control means for supplying fluid into said self-propelled units and for exhausting the fluid out of said self-propelled units, thereby moving said self-propelled units, said fluid control means including a fluid control section for contracting at least said balloons of one of said self-propelled units, and for supplying fluid into the others of said self-propelled units and for exhausting the fluid out of said others of said self-propelled units; and (d) detecting means for detecting an insertion amount of said driven unit;

and wherein said fluid control section contracts at least said balloons of said one of said self-propelled units, and supplies fluid into the others of said self-propelled units and exhausts the fluid out of them, when said detecting means detects a predetermined insertion amount.

* * * * *

UNITED STATES PATENT AND TRADEMARK OFFICE
CERTIFICATE OF CORRECTION

PATENT NO. : 5,090,259
DATED : February 25, 1992
INVENTOR(S) : SHISHIDO et al

It is certified that error appears in the above-identified patent and that said Letters Patent is hereby corrected as shown below:

TITLE PAGE:

Section [30] Foreign Application Priority Data:

Change Japanese application "6-29283" to --63-29283--.

Under Section [56] References Cited, right column:

Change the issue date of USP 4,807,484 from "2,1987" to --2/1989--.

Change the classification of USP 4,485,668 from "73/405 A" to --73/40.5A--.

Under "OTHER PUBLICATIONS":

After "Patent Abstracts of Japan", insert --Grp. P.959--.

At the end of the reference after "November 14, 1989", insert --(1-204015)--.

Signed and Sealed this

Twentieth Day of July, 1993

Attest:

MICHAEL K. KIRK

Attesting Officer     Acting Commissioner of Patents and Trademarks